(12) United States Patent
Schwede et al.

(10) Patent No.: US 9,109,004 B2
(45) Date of Patent: Aug. 18, 2015

(54) PROGESTERONE RECEPTOR ANTAGONISTS

(75) Inventors: Wolfgang Schwede, Glienicke (DE); Ulrich Klar, Berlin (DE); Carsten Möller, Berlin (DE); Andrea Rotgeri, Berlin (DE); Wilhelm Bone, Berlin (DE); Christoph Huwe, Berlin (DE)

(73) Assignee: Bayer Intellectual Property GmbH, Monheim (DE)

(*) Notice: Subject to any disclaimer, the term of this patent is extended or adjusted under 35 U.S.C. 154(b) by 285 days.

(21) Appl. No.: 13/578,500

(22) PCT Filed: Feb. 8, 2011

(86) PCT No.: PCT/EP2011/051780
§ 371 (c)(1), (2), (4) Date: Oct. 1, 2012

(87) PCT Pub. No.: WO2011/098436
PCT Pub. Date: Aug. 18, 2011

(65) Prior Publication Data
US 2013/0072464 A1    Mar. 21, 2013

(30) Foreign Application Priority Data
Feb. 10, 2010  (DE) .................. 10 2010 007 719

(51) Int. Cl.
| | | |
|---|---|---|
| A61K 31/567 | (2006.01) | |
| A61K 31/58 | (2006.01) | |
| C07J 1/00 | (2006.01) | |
| C07J 43/00 | (2006.01) | |
| C07J 41/00 | (2006.01) | |
| A61K 31/57 | (2006.01) | |

(52) U.S. Cl.
CPC ............ *C07J 43/003* (2013.01); *C07J 41/0083* (2013.01); *A61K 31/57* (2013.01); *A61K 31/58* (2013.01)
USPC ............ 514/179; 514/176; 540/113; 552/648

(58) Field of Classification Search
CPC .......................... C07J 41/0083; C07J 43/003
USPC .................... 552/648; 540/113; 514/176, 179
See application file for complete search history.

(56) References Cited

U.S. PATENT DOCUMENTS

| | | | |
|---|---|---|---|
| 4,386,085 A | 5/1983 | Teutsch et al. | |
| 4,519,946 A | 5/1985 | Teutsch et al. | |
| 4,609,651 A | 9/1986 | Rohde et al. | |
| 4,634,695 A | 1/1987 | Torelli et al. | |
| 4,900,725 A | 2/1990 | Nioue et al. | |
| 4,921,846 A | 5/1990 | Nedelec et al. | |
| 4,954,490 A | 9/1990 | Cook et al. | |
| 5,073,548 A | 12/1991 | Cook et al. | |
| 5,108,996 A | 4/1992 | Claussner et al. | |
| 5,272,140 A | 12/1993 | Loozen | |
| 5,407,928 A | 4/1995 | Kasch et al. | |
| 5,576,310 A | 11/1996 | Schubert et al. | |
| 5,693,628 A | 12/1997 | Schubert et al. | |
| 5,712,264 A | 1/1998 | Hamersma et al. | |
| 5,739,125 A | 4/1998 | Kasch et al. | |
| 5,986,115 A | 11/1999 | Bohlmann et al. | |
| 6,020,328 A | 2/2000 | Cook et al. | |
| 6,043,234 A | 3/2000 | Stöckemann et al. | |
| 6,225,298 B1 | 5/2001 | Spicer et al. | |
| 6,316,432 B1 | 11/2001 | Schwede et al. | |
| 6,476,079 B1 | 11/2002 | Jukarainen et al. | |
| 6,503,895 B2 | 1/2003 | Schwede et al. | |
| 6,806,263 B2 | 10/2004 | Schwede et al. | |
| 6,825,182 B2 | 11/2004 | Ring et al. | |
| 6,861,415 B2 | 3/2005 | Kim et al. | |
| 7,087,591 B2 | 8/2006 | Kim et al. | |
| 7,148,213 B2 | 12/2006 | Schwede et al. | |
| 7,192,942 B2 | 3/2007 | Grawe et al. | |
| 7,550,451 B2 | 6/2009 | Hillisch et al. | |
| 7,799,770 B2 | 9/2010 | Grawe et al. | |
| 7,910,573 B2 | 3/2011 | Beckmann et al. | |
| 8,053,426 B2 | 11/2011 | Fuhrmann et al. | |
| 2001/0016578 A1 | 8/2001 | Spicer et al. | |

(Continued)

FOREIGN PATENT DOCUMENTS

| | | |
|---|---|---|
| CA | 2280041 C | 8/1998 |
| EP | 0057115 A2 | 4/1982 |

(Continued)

OTHER PUBLICATIONS

Fuhrmann et al, "Synthesis and Biological Activity of a Novel, highly Potent Progesterone Receptor Antiagonist," J. Med. Chem., vol. 43, pp. 5010-5016 (2000).

Steinauer et al., "Systematic review of mifepristone for the treatment of uterine leiomyomata," Obstet Gynecol, vol. 103, No. 6, pp. 1331-1336 (Jun. 2004).

Chwalisz et al., "A randomized, controlled trial of asoprisnil, a novel selective progesterone receptor modulator, in women with uterine leiomyomata," Fertil Steril, vol. 87, No. 6, pp. 1399-1412 (Jun. 2007).

Kettel et al., "Endocrine responses to long-term administration of the antiprogesterone RU486 in patients with pelvic endometriosis," Fertil Steril, vol. 56, No. 3, pp. 402-407 (Sep. 1991).

Kettel et al., "Treatment of endometriosis with the antiprogesterone mifepristone (RU486)," Fertil Steril, vol. 65, No. 1, pp. 23-28 (Jan. 1996).

Kettel et al., "Preliminary report on the treatment of endometriosis with low-dose mifepristone (RU 486),". Am J Obstet Gynecol, vol. 178, No. 6, pp. 1151-1156 (Jun. 1998).

(Continued)

*Primary Examiner* — Barbara P Badio
(74) *Attorney, Agent, or Firm* — Karen B. King; Thomas C. Blankinship

(57) ABSTRACT

The invention relates to 17-hydroxy-17-pentafluoroethyl-estra-4,9(10)-dien-11-aryl derivatives of formula I with progesterone-antagonizing action and methods of production thereof, use thereof for the treatment and/or prevention of diseases and use thereof for producing medicinal products for the treatment and/or prevention of diseases, in particular uterine fibroids (myomata, uterine leiomyomata), endometriosis, heavy menstrual bleeding, meningiomata, hormone-dependent breast cancers and menopause-associated complaints or for fertility control and emergency contraception.

10 Claims, No Drawings

(56) References Cited

U.S. PATENT DOCUMENTS

| | | | |
|---|---|---|---|
| 2002/0045774 A1 | 4/2002 | Schwede et al. | |
| 2002/0143000 A1 | 10/2002 | Hegele-Hartung et al. | |
| 2003/0069434 A1 | 4/2003 | Bohlmann et al. | |
| 2003/0191099 A1 | 10/2003 | Bohlmann et al. | |
| 2004/0006241 A1 | 1/2004 | Grawe et al. | |
| 2004/0048841 A1 | 3/2004 | Hoffmann et al. | |
| 2004/0157811 A1 | 8/2004 | Lichtner et al. | |
| 2005/0080060 A1 | 4/2005 | Schwede et al. | |
| 2005/0277769 A1 | 12/2005 | Burton et al. | |
| 2007/0105828 A1 | 5/2007 | Joshi et al. | |
| 2009/0075989 A1 | 3/2009 | Schwede et al. | |
| 2011/0112057 A1 | 5/2011 | Fuhrmann et al. | |
| 2012/0149670 A1 | 6/2012 | Schwede et al. | |
| 2012/0184515 A1 | 7/2012 | Klar et al. | |
| 2012/0190660 A1 | 7/2012 | Klar et al. | |
| 2012/0232042 A1 | 9/2012 | Klar et al. | |
| 2012/0258941 A1 | 10/2012 | Klar et al. | |
| 2012/0316145 A1 | 12/2012 | Klar et al. | |
| 2013/0005697 A1 | 1/2013 | Schwede et al. | |
| 2013/0072464 A1 | 3/2013 | Schwede et al. | |

FOREIGN PATENT DOCUMENTS

| | | |
|---|---|---|
| EP | 0411733 B1 | 2/1991 |
| EP | 0676203 A1 | 10/1995 |
| EP | 909764 A1 | 4/1999 |
| EP | 0970103 B1 | 4/2002 |
| EP | 1862468 | 12/2007 |
| IN | 978/MUM/2005 | 8/2005 |
| JP | H11171774 A | 6/1999 |
| WO | 9603130 A1 | 2/1996 |
| WO | 9615794 | 5/1996 |
| WO | 9623503 A1 | 8/1996 |
| WO | 98/05679 A2 | 2/1998 |
| WO | 9807740 | 2/1998 |
| WO | 98/26783 A1 | 6/1998 |
| WO | 98/34947 A1 | 8/1998 |
| WO | 9933855 | 7/1999 |
| WO | 99/53924 A1 | 10/1999 |
| WO | 0147490 A1 | 7/2001 |
| WO | 02/32429 A2 | 4/2002 |
| WO | 03045972 A1 | 6/2003 |
| WO | 03/093292 | 11/2003 |
| WO | 2004014935 A1 | 2/2004 |
| WO | 2006/010097 A2 | 1/2006 |
| WO | 2008/058767 A1 | 5/2008 |
| WO | 2009138186 A2 | 11/2009 |
| ZA | 97/7482 | 2/1998 |

OTHER PUBLICATIONS

Möller et a., "Investigational developments for the treatment of progesterone-dependent diseases," Expert Opin. Investig. Drugs., vol. 17, No. 4, pp. 469-479 (2008).

Bagaria et al., Low-dose mifepristone in treatment of uterine leiomyoma: A randomised double-blind placebo-controlled clinical trial, The Royal Australian and New Zealand College of Obstetricians and Gynaecologists, vol. 49, pp. 77-83 (2009).

Murphy et al., "Regression of Uterine Leiomyomata in Response to the Antiprogesterone RU 486," J. Clin. Endocrinol. Metab., vol. 76, No. 2, pp. 513-517 (1993).

Bohl et al, "Molecular mechanics and X-ray crystal structure investigations on conformations of 11β substituted 4,9-dien-3-one steroids," J. Mol. Graphics, vol. 7, pp. 122-153 (Sep. 1989).

Braga et al., "3.3 Crystal Polymorphism: Challenges at the Crossroads of Science and Technology," Making Crystals by Design (Dario Braga and Fabrizia Grepioni eds., Wiley-VCH Verlag GmbH & Co. KgaA, Weinheim, Germany), pp. 293-314 (2007).

Cabri et al., "Polymorphisms and Patent, Market, and Legal Battles: Cefdinir Case Study," Organic Process Research & Devel., vol. 11, No. 1, pp. 64-72 (2007).

Caira, "Crystalline Polymorphism of Organic Compounds," Topics in Current Chemistry, vol. 198, pp. 164-208. (1998).

Davey, "Solvent Effects in Crystallization Processes," Current Topics in Material Science, vol. 8, pp. 429-479.

English Translation of Office Action for European Application No. 06090095.8 dated Jan. 16, 2007.

Braja, "Mifepristone (RU-486), the recently developed antiprogesterone drug and tis analogues," J. Indian Inst. Sci., vol. 81, pp. 287-298 (May-Jun. 2001).

English Language Abstract of WO 2003/093292.

Maibauer et al., "First human data for ZK 230211 (ZK-PRA), a new progesterone receptor antagonist: a phase I clinical analysis of safety and pharmacokinetics in healthy postmenopausal women," Abstracts-Poster Session IV, 29th Annual San Antonio Breast Cancer Symposium, Dec. 14-17, 2006.

Tellekson et al., "Strategies for Attacking and Defending Pharmaceutical Patents: A Modern Take on 'The Art of War,'" Int. Property & Techn. Law Journal, vol. 17, No. 12, pp. 5-14 (Dec. 2005).

English Language Translation of EP0411733, 1991.

English Language Translation of EP0676203, 1995.

English Language Translation of WO1998/026783, 1998.

English Language Abstract of WO1999/053924, 1998.

English Language Abstract of JP H11171774, 1999.

Vippagunta et al., "Crystalline Solids," Adv. Drug Delivery Reviews, vol. 48, pp. 3-26 (2001).

Patani et al., "Bioisosterism: A Rational Approach in Drug Design," Chem. Rev., vol. 96, pp. 3147-3176 (1996).

Hazra, et al.,"Mifepristone (RU-486), the Recently Developed Antiprogesterone Drug and its Analogues," J. Indian Inst. Sci, May-Jun. 2001, 81:287-298.

Van Geerstein et al., "Structure of the n-Butyl Acetate Solvate of 11β-[4-(Dimethylamino)phenyl]-17β-hydroxy-17α-(1-propynyl)estra-4,9-dien-3-one," Acta Cryst., C42, pp. 1521-1523 (1986).

U.S. Appl. No. 13/384,332, 371(c) date Jun. 4, 2012, published as US 2012-0232042.

U.S. Appl. No. 13/384,765, 371(c) date Apr. 5, 2012, published as US 2012-0184515.

U.S. Appl. No. 13/386,420 371(c) date Apr. 5, 2012, published as US 2012-0190660.

U.S. Appl. No. 13/386,031 371(c) Aug. 28, 2012, published as US 2012-0316145.

U.S. Appl. No. 13/386,421 371(c) date Jun. 25, 2012, published as US 2012-0258941.

U.S. Appl. No. 13/376,512, 371(c) date Feb. 27, 2012, published as US 2012-0149670.

U.S. Appl. No. 13/577,799, 371(c) date Sep. 21, 2012, published as US 2013-0005697.

PROGESTERONE RECEPTOR ANTAGONISTS

The invention relates to 17-hydroxy-17-pentafluoroethyl-estra-4,9(10)-dien-11-aryl derivatives of formula I with progesterone-antagonizing action and methods of production thereof, use thereof for the treatment and/or prevention of diseases and use thereof for the production of medicinal products for the treatment and/or prevention of diseases, in particular uterine fibroids (myomata, uterine leiomyomata), endometriosis, heavy menstrual bleeding, meningiomata, hormone-dependent breast cancers and menopause-associated complaints or for fertility control and emergency contraception.

These compounds are valuable active pharmaceutical ingredients. Among other things they can be used for the production of pharmaceutical preparations for treating uterine fibroids or endometriosis, heavy menstrual bleeding, meningiomata, hormone-dependent breast cancers and menopause-associated complaints or for fertility control and emergency contraception. For the treatment of uterine fibroids and endometriosis the compounds according to the invention can also be administered sequentially in combination with gestagens. In such a treatment regimen the compounds according to the invention could be administered over a period of 1-6 months, followed by a pause in treatment or sequential treatment with a gestagen for a period of 2-6 weeks or followed by treatment with an oral contraceptive (OC combinations) over the same period.

The efficacy of the compounds according to the invention as progesterone receptor antagonist was demonstrated in vitro in transactivation tests and in vivo in the rat (termination of early pregnancy).

Compounds with antagonistic action on the progesterone receptor (competitive progesterone receptor antagonists) have been known since 1982 (RU 486; EP57115) and since then have been described extensively. Progesterone receptor antagonists with a fluorinated 17α side chain were published in WO 98/34947 and Fuhrmann et al., J. Med. Chem. 43, 5010-5016 (2000).

The compounds with a fluorinated 17α side chain described in WO 98/34947 generally have a very strong antagonistic activity on the progesterone receptor. Compounds that are very potent and are therefore preferred in WO 98/34947 are 11β-(4-acetylphenyl)-20,20,21,21,21-pentafluoro-17-hydroxy-19-nor-17α-pregna-4,9-dien-3-one, 11β-(4-acetylphenyl)-20,20,21,21,21-pentafluoro-17-hydroxy-19-nor-17α-pregna-4-en-3-one and 6'-acetyl-9,11β-dihydro-17β-hydroxy-17α-(1,1,2,2,2-pentafluoroethyl)-4'H-naphth[3',2',1':10,9,11]ester-4-en-3-one. These compounds are converted in vivo to various metabolites to a considerable extent, which sometimes have strong, and sometimes lower pharmacological activity. Metabolism occurs mainly on the 4-substituent of the 11-phenyl residue. Compounds are described in WO 2008/058767 that are at least partly metabolites of the compounds described in WO 98/34947.

The problem to be solved by the present invention is to provide highly potent competitive progesterone receptor antagonists and thus create alternative treatment possibilities for gynaecological diseases.

The present invention relates to 17-hydroxy-17-pentafluoroethyl-estra-4,9(10)-dien-11-aryl derivatives with the general chemical formula I:

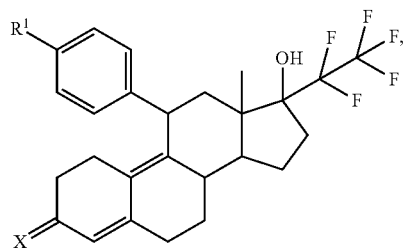

in which
$R^1$ stands either for a residue Y or for a phenyl ring substituted with Y,
Y stands for a group

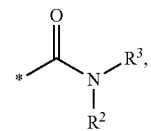

$R^2$ and $R^3$
may be identical or different and stand for hydrogen, an optionally —N(CH$_3$)$_2$,

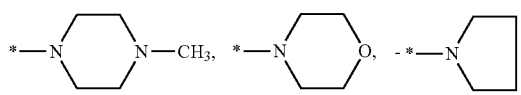

or —NHC(O)CH$_3$ substituted C$_1$-C$_6$-alkyl residue, a

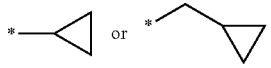

residue
a 6-10-membered aryl residue optionally substituted one, two or more times with halogen (—F, —Cl, —Br, —I), —OH, —O-alkyl, —C(O)OH, —C(O)O-alkyl, —C(O)NH$_2$, —C(O)NH-alkyl, —C(O)N-dialkyl, —C(O)NH-aryl, —C(O)NH-heteroaryl, —NH$_2$, —NH(C$_1$-C$_6$-alkyl), —N(C$_1$-C$_6$-alkyl)$_2$, in particular —N(CH$_3$)$_2$, —NHC(O)alkyl, —NO$_2$, —N$_3$, —CN, C$_1$-C$_6$-alkyl, —C$_1$-C$_6$-perfluoro-alkyl, —C$_1$-C$_6$-acyl, —C$_1$-C$_6$-acyloxy, —SO$_2$NH$_2$, —SO$_2$NH-alkyl or —SO$_2$N-dialkyl,
a 5-10-membered heteroaryl residue optionally substituted one, two or more times with the aforementioned substituents of the 6-10-membered aryl residue,
a C$_1$-C$_6$-aralkyl residue substituted on the aryl ring optionally one, two or more times with the aforementioned substituents of the 6-10-membered aryl residue or
a C$_1$-C$_6$-heteroarylalkyl residue substituted on the heteroaryl ring optionally one, two or more times with the aforementioned substituents of the 6-10-membered aryl residue
or else
$R^2$ and $R^3$
are together a constituent of a 3-10-membered ring optionally alkyl-, carboxyl-, alkylcarboxyl-, alkylcarbonyl-, aminocarbonyl-, aryl-, in particular phenyl-, aralkyl-, heteroaryl-, heteroarylalkyl-, aminoalkyl- or dimethylaminoalkyl-substituted on the carbon or alkyl-, alkanoyl-, alkylcarboxyl-, carboxyl-, aryl, in particular phenyl-, pyridinyl-, pyrimidinyl-, pyrazinyl-, sulphonyl-, benzoyl-, alkylsulphonyl-, arylsulphonyl-, aminocarbonyl-, dimethylaminocarbonyl-, aminocarbonylalkyl-, alkylaminocarbonylalkyl-, aralkyl-, in particular phenylalkyl-, heterocyclylalkyl-heteroarylalkyl-, aminoalkyl- or

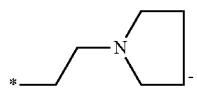

substituted on the nitrogen, which optionally contains nitrogen, oxygen or sulphur atoms, which can optionally be oxidized to the sulphoxide or sulphone, wherein optionally an aromatic can be condensed onto the 3-10-membered ring, X denotes an oxygen atom, $NOR^4$ or $NNHSO_2R^4$ and $R^4$ is selected from the group comprising hydrogen, $C_1$-$C_6$-alkyl and aryl and their salts, solvates or solvates of the salts, including all crystal modifications (* denotes the site of attachment on the parent substance).

The compounds according to the invention of general formula I can exist in stereoisomeric forms (enantiomers, diastereomers), depending on their structure. The invention therefore comprises the enantiomers or diastereomers and mixtures thereof including the racemates. The stereoisomerically homogeneous constituents can be isolated in a known way from said mixtures of enantiomers and/or diastereomers.

Each of the stated substituents on the steroid skeleton structure can be both in an α and in a β position.

If the compounds according to the invention can occur in tautomeric forms, the present invention comprises all tautomeric forms.

Physiologically harmless salts of the compounds according to the invention are preferred as salts in the context of the present invention. However, salts that themselves are not suitable for pharmaceutical applications, but for example can be used for the isolation or purification of the compounds according to the invention, are also comprised.

Physiologically harmless salts of the compounds according to the invention comprise—if a basic function is contained—salts with inorganic or organic acids, in particular mineral acids, carboxylic acids and sulphonic acids, e.g. salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically harmless salts of the compounds according to the invention comprise—if an acid function is contained—alkali metal salts, alkaline-earth metal salts or ammonium salts, such as can be obtained by reaction with corresponding inorganic or organic bases. For example and preferably, we may mention alkali metal salts (e.g. sodium and potassium salts), alkaline-earth salts (e.g. calcium and magnesium salts) and ammonium salts, derived from ammonia or organic amines with 1 to 16 carbon atoms, such as for example and preferably ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine, N-methylpiperidine, N-methyl-glucamine, D-methyl-glucamine, ethyl-glucamine, 1,6-hexadiamine, glucosamine, N-methylglycine, 2-amino-1,3-propanediol, tris-hydroxymethylaminomethane and 1-amino-2,3,4-butanetriol.

Those forms of the compounds according to the invention that display adduct formation with solvent molecules in the solid or liquid state are termed solvates in the context of the invention. The solvent can be present in a stoichiometric or in a non-stoichiometric ratio. In the case of stoichiometric solvates, they are also called hemi-, (semi-), mono-, sesqui-, di-, tri-, tetra-, penta-, etc. solvates. Hydrates are a special form of solvates, where coordination takes place with water.

Moreover, the present invention also comprises prodrugs of the compounds according to the invention. The term "prodrugs" comprises compounds that are converted, during their residence time in the body, to compounds according to the invention, for example by enzymatic or hydrolytic processes.

In the context of the present invention, unless specified otherwise, the substituents have the following meanings:

Alkyl stands for a linear or branched alkyl group with 1-6 carbon atoms, for example methyl, ethyl, propyl, isopropyl, n-butyl, sec-butyl, isobutyl, tert-butyl, n-pentyl, isopentyl, neopentyl, hexyl but also for cyclopropyl or cyclopropylmethyl.

Aryl stands for a mono- to tricyclic aromatic, substituted or unsubstituted carbocyclic residue, for example phenyl or naphthyl.

The aryl residue can be substituted one, two or more times with halogen (—F, —Cl, —Br, —I), —OH, —O-alkyl, —$CO_2H$, —$CO_2$-alkyl, —C(O)$NH_2$, —C(O)NH-alkyl, —C(O)N-dialkyl, —C(O)NH-aryl, —C(O)NH-heteroaryl, —$NH_2$, —NH($C_1$-$C_6$-alkyl), —N($C_1$-$C_6$-alkyl)$_2$, in particular —N(CH$_3$)$_2$, —NHC(O)alkyl, —$NO_2$, —$N_3$, —CN, —$C_1$-$C_6$-alkyl, —$C_1$-$C_6$-perfluoro-alkyl, —$C_1$-$C_6$-acyl, —$C_1$-$C_6$-acyloxy, —$SO_2NH_2$, —$SO_2$NH-alkyl or —$SO_2$N-dialkyl.

Heteroaryl stands for an aromatic, mono- or bicyclic residue with as a rule 5 to 10, preferably 5 to 6 ring atoms and up to 5, preferably up to 4 heteroatoms from the series S, O and N, for example and preferably for benzofuranyl, benzothiophenyl, quinolinyl, furyl, imidazolyl, indazolyl, indolyl, isoquinolinyl, oxazolyl, pyridazinyl, pyridyl, pyrimidyl, pyrrolyl, thiazolyl, thienyl, pyrazolyl, isoxazolyl, pyrazinyl, quinolyl or tetrazolyl.

The heteroaryl residue can be substituted one, two or more times with halogen (—F, —Cl, —Br, —I), —OH, —O-alkyl, —$CO_2H$, —$CO_2$-alkyl, —C(O)$NH_2$, —C(O)NH-alkyl, —C(O)N-dialkyl, —C(O)NH-aryl, —C(O)NH-heteroaryl, —$NH_2$, —NH($C_1$-$C_6$-alkyl), —N($C_1$-$C_6$-alkyl)$_2$, in particular —N(CH$_3$)$_2$, —NHC(O)alkyl, —$NO_2$, —$N_3$, —CN, —$C_1$-$C_6$-alkyl, —$C_1$-$C_6$-perfluoro-alkyl, —$C_1$-$C_6$-acyl, —$C_1$-$C_6$-acyloxy, —$SO_2NH_2$, —$SO_2$NH-alkyl or —$SO_2$N-dialkyl.

Aralkyl stands for aralkyl groups, which can contain up to 14 carbon atoms, preferably 6-10 carbon atoms in the ring, and 1-8, preferably 1-4, carbon atoms in the alkyl chain. For example benzyl, phenylethyl, naphthylmethyl, naphthylethyl may come into consideration as aralkyl residues.

The aryl moiety of the aralkyl residue can be substituted one, two or more times with halogen (—F, —Cl, —Br, —I), —OH, —O-alkyl, —$CO_2H$, —$CO_2$-alkyl, —C(O)$NH_2$, —C(O)NH-alkyl, —C(O)N-dialkyl, —C(O)NH-aryl, —C(O)NH-heteroaryl, —$NH_2$, —NH($C_1$-$C_6$-alkyl), —N($C_1$-$C_6$-alkyl)$_2$, in particular —N(CH$_3$)$_2$, —NHC(O)alkyl, —$NO_2$, —$N_3$, —CN, —$C_1$-$C_6$-alkyl, $C_1$-$C_6$-perfluoro-alkyl, —$C_1$-$C_6$-acyl, —$C_1$-$C_6$-acyloxy, —$SO_2NH_2$, —$SO_2$NH-alkyl or —$SO_2$N-dialkyl.

Heteroarylalkyl stands for heteroaryl-alkyl groups, wherein heteroaryl has the meaning defined above, and which can contain 1-6, preferably 1-4, carbon atoms in the alkyl chain. For example furylmethyl, thienylethyl or pyridylpropyl may come into consideration as heteroarylalkyl residues.

The heteroaryl moiety of the heteroarylalkyl residue can be substituted one, two or more times with halogen (—F, —Cl, —Br, —I), —OH, —O-alkyl, —CO$_2$H, —CO$_2$-alkyl, —C(O)NH$_2$, —C(O)NH-alkyl, —C(O)N-dialkyl, —C(O)NH-aryl, —C(O)NH-heteroaryl, —NH$_2$, —NH(C$_1$-C$_6$-alkyl), —N(C$_1$-C$_6$-alkyl)$_2$, in particular —N(CH$_3$)$_2$, —NHC(O)alkyl, —NO$_2$, —N$_3$, —CN, —C$_1$-C$_6$-alkyl, —C$_1$-C$_6$-perfluoro-alkyl, —C$_1$-C$_6$-acyl, —C$_1$-C$_6$-acyloxy, —SO$_2$NH$_2$ or —SO$_2$NH-alkyl, —SO$_2$N-dialkyl.

If residues in the compounds according to the invention are substituted, unless specified otherwise, the residues can be substituted singly or multiply. In the context of the present invention, for all residues that occur multiply, their meaning is independent of one another. Substitution with one, two or three identical or different substituents is preferable. Substitution with one substituent is quite especially preferred.

For compounds in which R$^2$ and R$^3$ are together a constituent of an optionally substituted ring, this ring can be 3-10-membered and can bear, apart from the nitrogen atom that is present, only carbon atoms or else up to 2 further heteroatoms. We may mention, as further heteroatoms, in particular, optionally substituted nitrogen, oxygen and optionally oxidized sulphur. Alkyl, carboxyl, alkylcarboxyl, alkylcarbonyl, aminocarbonyl, aryl, in particular phenyl, aralkyl, heteroaryl, heteroarylalkyl, aminoalkyl or dimethylaminocarbonyl groups may come into consideration as substituents on the carbon. Alkyl, alkanoyl, alkylcarboxyl, carboxyl, aryl, in particular phenyl, pyridinyl, pyrimidinyl, pyrazinyl, sulphonyl, benzoyl, alkylsulphonyl, arylsulphonyl, aminocarbonyl, dimethylaminocarbonyl, aminocarbonylalkyl, alkylaminocarbonylalkyl, aralkyl, in particular phenylalkyl, heterocyclylalkyl, heteroarylalkyl, aminoalkyl or

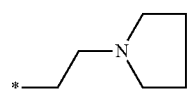 [SMILES: *CCN1CCCC1]

groups may in particular come into consideration as substituents on the nitrogen. Sulphur atoms in the ring can be oxidized to the sulphoxide or sulphone. Optionally an aromatic can be condensed onto the 3-10-membered ring.

As rings that are formed by R$^2$ and R$^3$ together, we may mention in particular piperidines, piperazines, morpholines, diazepanes, thiomorpholines, dioxidothiomorpholines, tetrahydropyrroles.

Heterocyclyl in the sense of the invention is a non-aromatic mono- or bicyclic ring system with at least one heteroatom or a hetero group. Nitrogen atoms, oxygen atoms and/or sulphur atoms can be present as heteroatoms. —S(O)—, —S(O)$_2$— can be present as hetero groups.

Heterocyclylalkyl stands for heterocyclylalkyl groups, wherein heterocyclyl has the meaning defined above, and which can contain 1-6, preferably 1-4, carbon atoms in the alkyl chain. For example pyrrolidinoethyl may come into consideration as heterocyclylalkyl residues.

A monocyclic heterocyclyl ring according to the present invention can have 3 to 8, preferably 5 to 8, especially preferably 5 or 6 ring atoms. As examples of monocyclic heterocyclyl residues with 5 ring atoms we may mention: pyrrolidinyl, imidazolidinyl, pyrazolidinyl, pyrrolinyl and tetrahydrofuranyl. As examples of monocyclic heterocyclyl residues with 6 ring atoms we may mention: piperidinyl, piperazinyl, morpholinyl, tetrahydropyranyl and thiomorpholinyl.

A bicyclic heterocyclyl residue according to the present invention can have 5 to 12, preferably 8 to 10 ring atoms. 5- to 8-membered, monocyclic saturated heterocyclyl residues with up to two heteroatoms from the series O, N and S are preferred. Morpholinyl, piperidinyl and pyrrolidinyl are especially preferred.

The definitions of residues stated in detail in the respective combinations or preferred combinations of residues are also replaced with any definitions of residues of another combination independently of the particular stated combinations of the residues.

Combinations of two or more of the aforementioned preferred ranges are quite especially preferred.

The following compounds of general formula V, which are included under general formula I, are also especially preferred:

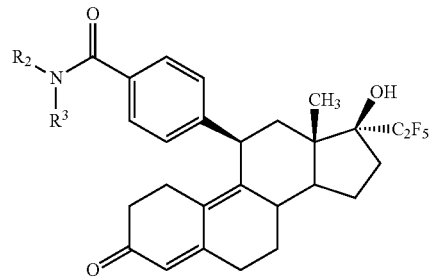

Formula V in which
R$^2$ denotes hydrogen, C$_1$-C$_4$-alkyl (in particular methyl, ethyl, cyclopropyl or cyclopropylmethyl), —(CH$_2$)$_k$—N(CH$_3$)$_2$ with k=2 or 3, —CH$_2$—CH$_2$—NH—CO—CH$_3$ and —(CH$_2$)$_k$—R$^5$ with k=2 or 3 and R$^5$=

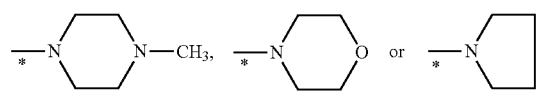

and
R$^3$ denotes hydrogen or C$_1$-C$_4$-alkyl (in particular methyl or ethyl)
and their salts, solvates or solvates of the salts, including all crystal modifications, in particular the compounds:
4-[(11β,17β)-17-hydroxy-3-oxo-17-(pentafluoroethyl)estra-4,9-dien-11-yl]benzamide (Ex. 1),
4-[(11β,17β)-17-hydroxy-3-oxo-17-(pentafluoroethyl)estra-4,9-dien-11-yl]-N,N-dimethylbenzamide (Ex. 2),
N-[2-(dimethylamino)ethyl]-4-[(11β,17β)-17-hydroxy-3-oxo-17-(pentafluoroethyl)estra-4,9-dien-11-yl]benzamide (Ex. 7),
N-[3-(dimethylamino)propyl]-4-[(11β,17β)-17-hydroxy-3-oxo-17-(pentafluoroethyl)estra-4,9-dien-11-yl]benzamide (Ex. 8),
N-[2-(dimethylamino)ethyl]-4-[(11β,17β)-17-hydroxy-3-oxo-17-(pentafluoroethyl)estra-4,9-dien-11-yl]-N-methylbenzamide (Ex. 9),
4-[(11β,17β)-17-hydroxy-3-oxo-17-(pentafluoroethyl)estra-4,9-dien-11-yl]-N-[3-(morpholin-4-yl)propyl]benzamide (Ex. 13), N-ethyl-4-[(11β,17β)-17-hydroxy-3-oxo-17-(pentafluoroethyl)estra-4,9-dien-11-yl]benzamide (Ex. 19), N,N-diethyl-4-[(11β,17β)-17-hydroxy-3-oxo-17-(pentafluoroethyl)estra-4,9-dien-11-yl]benzamide (Ex. 27), N-(2-acetamidoethyl)-4-[(11β,17β-17-hydroxy-3-oxo-17-(pentafluoroethyl)estra-4,9-dien-11-yl]benzamide (Ex. 37), N-cyclopropyl-4-[(11β,17β)-17-hydroxy-3-oxo-17-(pentafluoroethyl)estra-4,9-dien-11-yl]benzamide (Ex. 42), 4-[(11β,17β)-17-hydroxy-3-oxo-17-(pentafluoroethyl)estra-4,9-dien-11-yl]-N-[2-(pyrrolidin-1-yl)ethyl]benzamide (Ex. 54), N-(cyclopropylmethyl)-4-[(11β,17β)-17-hydroxy-3-oxo-17-(pentafluoroethyl)estra-4,9-dien-11-yl]benzamide (Ex. 59) or 4-[(11β,17β)-17-hydroxy-3-oxo-17-(pentafluoroethyl)estra-4,9-dien-11-yl]-N-[2-(4-methylpiperazin-1-yl)ethyl]benzamide (Ex. 62).

The following compounds of general formula VI, which are included under general formula I, are also especially preferred:

Formula VI

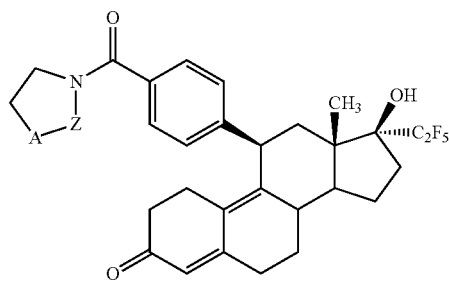

in which

Z denotes —CH$_2$— or —CH$_2$—CH$_2$—,

A denotes oxygen, —CHR$^6$— or —NR$^7$— and

R$^6$, R$^7$ denote hydrogen,

C$_1$-C$_4$-alkyl, a —(CH$_2$)$_l$-aryl residue with I=0, 1 or 2, optionally substituted one, two or more times with halogen (—F, —Cl, —Br, —I), —OH, —O-alkyl, —CO$_2$H, —CO$_2$-alkyl, —C(O)NH$_2$, —C(O)NH-alkyl, —C(O)N-dialkyl, —C(O)NH-aryl, —C(O)NH-heteroaryl, —NH$_2$, —NH(C$_1$-C$_6$-alkyl), —N(C$_1$-C$_6$-alkyl)$_2$, in particular —N(CH$_3$)$_2$, —NHC(O)alkyl, —NO$_2$, —N$_3$, —CN, —C$_1$-C$_6$-alkyl, —C$_1$-C$_6$-perfluoro-alkyl, —C$_1$-C$_6$-acyl, —C$_1$-C$_6$-acyloxy, —SO$_2$NH$_2$, —SO$_2$NH-alkyl or —SO$_2$N-dialkyl, a —(CH$_2$)$_l$-heteroaryl residue with up to two heteroatoms and I=0, 1 or 2, optionally substituted one, two or more times with halogen (—F, —Cl, —Br, —I), —OH, —O-alkyl, —CO$_2$H, —CO$_2$-alkyl, —C(O)NH$_2$, —C(O)NH-alkyl, —C(O)N-dialkyl, —C(O)NH-aryl, —C(O)NH-heteroaryl, —NH$_2$, —NH(C$_1$-C$_6$-alkyl), —N(C$_1$-C$_6$-alkyl)$_2$, in particular —N(CH$_3$)$_2$, —NHC(O)alkyl, —NO$_2$, —N$^3$, —CN, —C$_1$-C$_6$-alkyl, —C$_1$-C$_6$-perfluoro-alkyl, —C$_1$-C$_6$-acyl, —C$_1$-C$_6$-acyloxy, —SO$_2$NH$_2$, —SO$_2$NH-alkyl or —SO$_2$N-dialkyl or —COR$^8$ and R$^8$ denotes —OH, —(C$_1$-C$_4$-alkyl), -aryl, —O—C$_1$-C$_4$-alkyl, —NH—(C$_1$-C$_4$-alkyl), —N(CH$_3$)$_2$, —SO$_2$—(C$_1$-C$_4$-alkyl), and their salts, solvates or solvates of the salts, including all crystal modifications.

The compounds that come under formula VI are also especially preferred wherein:

R$^6$ denotes hydrogen, phenyl, —CO$_2$H, —CO$_2$H$_3$ and

R$^7$ denotes hydrogen, —CH$_3$, —(CH$_2$)$_l$-phenyl with I=0, 1 or 2,

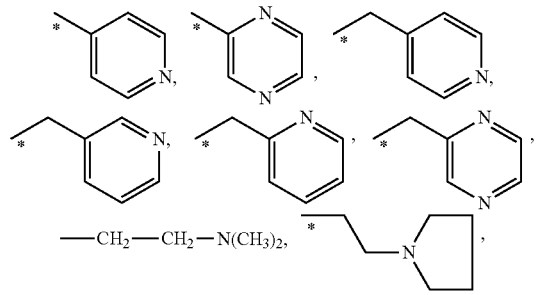

—CO—CH$_3$, —CO-phenyl, —CO$_2$CH$_3$, —CH$_2$C(CH$_3$)$_3$, —CO—NH—CH$_3$, —CO—N(CH$_3$)$_2$; —SO$_2$—CH$_3$, —CH$_2$CO—NH—CH$_3$, in particular the compounds:

(11β,17β)-17-hydroxy-11-{4-[(4-methylpiperazin-1-yl)carbonyl]phenyl}-17-(pentafluoroethyl)estra-4,9-dien-3-one (Ex. 3), tert-butyl-4-{4-[(11β,17β)-17-hydroxy-3-oxo-17-(pentafluoroethyl)estra-4,9-dien-11-yl]benzoyl}piperazine-1-carboxylate (Ex. 4), (11β,17β)-17-hydroxy-17-(pentafluoroethyl)-11-[4-(piperidin-1-ylcarbonyl)phenyl]estra-4,9-dien-3-one (Ex. 5), methyl-1-{4-[(11β,17β)-17-hydroxy-3-oxo-17-(pentafluoroethyl)estra-4,9-dien-11-yl]benzoyl}piperidine-4-carboxylate (Ex. 6), (11β,17β)-17-hydroxy-17-(pentafluoroethyl)-11-[4-(pyrrolidin-1-ylcarbonyl)phenyl]estra-4,9-dien-3-one (Ex. 15)

(11β,17β)-17-hydroxy-11-[4-(morpholin-4-ylcarbonyl)phenyl]-17-(pentafluoroethyl)estra-4,9-dien-3-one (Ex. 29), (11β,17β)-17-hydroxy-17-(pentafluoroethyl)-11-{4-[(4-phenylpiperazin-1-yl)carbonyl]phenyl}estra-4,9-dien-3-one (Ex. 30), (11β,17β)-11-{4-[(4-benzylpiperazin-1-yl)carbonyl]phenyl}-17-hydroxy-17-(pentafluoroethyl)estra-4,9-dien-3-one (Ex. 40), (11β,17β)-17-hydroxy-17-(pentafluoroethyl)-11-(4-{[4-(2-phenylethyl)piperazin-1-yl]carbonyl}phenyl)estra-4,9-dien-3-one (Ex. 44), (11β,17β)-17-hydroxy-17-(pentafluoroethyl)-11-(4-{[4-(pyridin-4-yl)piperazin-1-yl]carbonyl}phenyl)estra-4,9-dien-3-one (Ex. 45), (11β,17β)-17-hydroxy-17-(pentafluoroethyl)-11-(4-{[4-(pyrazin-2-yl)piperazin-1-yl]carbonyl}phenyl)estra-4,9-dien-3-one (Ex. 46), (11β,17β)-11-[4-({4-[2-(dimethylamino)ethyl]piperazin-1-yl}carbonyl)phenyl]-17-hydroxy-17-(pentafluoroethyl)estra-4,9-dien-3-one (Ex. 47), (11β,17β)-17-hydroxy-17-(pentafluoroethyl)-11-[4-({4-[2-(pyrrolidin-1-yl)ethyl]piperazin-1-yl}carbonyl)phenyl]estra-4,9-dien-3-one (Ex. 48), (11β,17β)-17-hydroxy-17-(pentafluoroethyl)-11-(4-{[4-(pyridin-4-ylmethyl)piperazin-1-yl]carbonyl}phenyl)estra-4,9-dien-3-one (Ex. 49), (11β,17β)-17-hydroxy-17-(pentafluoroethyl)-11-{4-[(4-phenylpiperidin-1-yl)carbonyl]phenyl}estra-4,9-dien-3-one (Ex. 63), (11β,17β)-11-{4-[(4-benzoylpiperazin-1-yl)carbonyl]phenyl}-17-hydroxy-17-(pentafluoroethyl)estra-4,9-dien-3-one (Ex. 65), 4-{4-[(11β,17β)-17-hydroxy-3-oxo-17-(pentafluoroethyl)estra-4,9-dien-11-yl]benzoyl}-N,N-dimethylpiperazine-1-carboxamide (Ex. 66), (11β,17β)-17-hydroxy-11-(4-{[4-(methylsulphonyl)piperazin-1-yl]carbonyl}phenyl)-17-(pentafluoroethyl)estra-4,9-dien-3-one (Ex. 67), (11β,17β)-17-hydroxy-17-(pentafluoroethyl)-11-(4-{[4-(pyridin-2-ylmethyl)piperazin-1-yl]carbonyl}phenyl)estra-4,9-dien-3-one (Ex. 68), (11β,17β)-17-hydroxy-17-(pentafluoroethyl)-11-(4-{[4-(pyridin-3-ylmethyl)piperazin-1-yl]carbonyl}phenyl)estra-4,9-dien-3-one (Ex. 69), methyl-4-{4-[(11β,17β)-17-hydroxy-3-oxo-17-(pentafluoroethyl)estra-4,9-dien-11-yl]benzoyl}piperazine-1-carboxylate (Ex. 70), 2-(4-{4-[(11β,17β)-17-hydroxy-3-oxo-17-(pentafluoroethyl)estra-4,9-dien-11-yl]benzoyl}piperazin-1-yl)-N-methylacetamide (Ex. 71), (11β,17β)-17-hydroxy-17-(pentafluoroethyl)-11-[4-(piperazin-1-ylcarbonyl)phenyl]estra-4,9-dien-3-one (Ex. 73) and (11β,17β)-11-{4-[(4-acetylpiperazin-1-yl)carbonyl]phenyl}-17-hydroxy-17-(pentafluoroethyl)estra-4,9-dien-3-one (Ex. 74).

1-{4-[(11β,17β)-17-hydroxy-3-oxo-17-(pentafluoroethyl)estra-4,9-dien-11-yl]benzoyl}piperidine-4-carboxylic acid (Ex. 75).

The following compounds of general formula VII, which are included under general formula I, are also especially preferred:

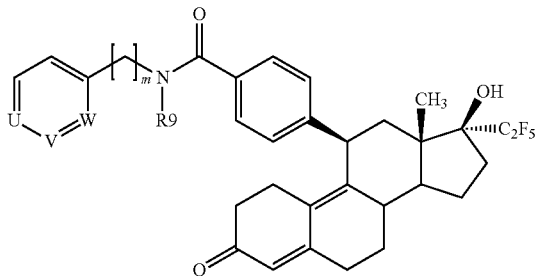

Formula VII in which m denotes 0, 1 or 2, $R^9$ denotes hydrogen or —$C_1$-$C_4$-alkyl, in particular methyl or ethyl, U, V and W independently of one another denote —CH═, —$CR^{10}$═ or —N═, and —$CR^{10}$═ or —N═ regardless of the position in the aromatic ring are present at most once and $R^{10}$ denotes —O—($C_1$-$C_4$-alkyl), halogen, —$COR^{11}$ with $R^{11}$═—OH, —$NH_2$ or —O—($C_1$-$C_4$-alkyl), —$SO_2$—$NH_2$; —NH—CO—($C_1$-$C_4$-alkyl), or —CO—NH-aryl.

The compounds that come under formula VI are also especially preferred wherein:

$R^9$ denotes hydrogen, methyl or ethyl and $R^{10}$ denotes —O—$CH_3$, —Cl, —$CO_2H$, —$CO_2CH_3$, —CO—$NH_2$, —$SO_2$—$NH_2$; —NH—CO—$CH_3$ or —CO—NH-phenyl and their salts, solvates or solvates of the salts, including all crystal modifications, in particular the compounds:

methyl-2-({4-[(11β,17β)-17-hydroxy-3-oxo-17-(pentafluoroethyl)estra-4,9-dien-11-yl]benzoyl}amino)benzoate (Ex. 10)

4-[(11β,17β)-17-hydroxy-3-oxo-17-(pentafluoroethyl)estra-4,9-dien-11-yl]-N-(pyridin-2-yl)benzamide (Ex. 11)

4-[(11β,17β)-17-hydroxy-3-oxo-17-(pentafluoroethyl)estra-4,9-dien-11-yl]-N-(pyridin-3-yl)benzamide (Ex. 12)

4-[(11β,17β)-17-hydroxy-3-oxo-17-(pentafluoroethyl)estra-4,9-dien-11-yl]-N-(pyridin-4-yl)benzamide (Ex. 14)

4-[(11β,17β)-17-hydroxy-3-oxo-17-(pentafluoroethyl)estra-4,9-dien-11-yl]-N-(2-phenylethyl)benzamide (Ex. 16)

4-[(11β,17β)-17-hydroxy-3-oxo-17-(pentafluoroethyl)estra-4,9-dien-11-yl]-N-(4-sulphamoylbenzyl)benzamide (Ex. 18)

4-[(11β,17β)-17-hydroxy-3-oxo-17-(pentafluoroethyl)estra-4,9-dien-11-yl]-N-(pyridin-2-ylmethyl)benzamide (Ex. 20)

4-[(11β,17β)-17-hydroxy-3-oxo-17-(pentafluoroethyl)estra-4,9-dien-11-yl]-N-(pyridin-4-ylmethyl)benzamide (Ex. 21)

4-[(11β,17β)-17-hydroxy-3-oxo-17-(pentafluoroethyl)estra-4,9-dien-11-yl]-N-phenylbenzamide (Ex. 22)

4-[(11β,17β)-17-hydroxy-3-oxo-17-(pentafluoroethyl)estra-4,9-dien-11-yl]-N-(2-methoxyphenyl)benzamide (Ex. 23)

4-[(11β,17β)-17-hydroxy-3-oxo-17-(pentafluoroethyl)estra-4,9-dien-11-yl]-N-(3-methoxyphenyl)benzamide (Ex. 24)

4-[(11β,17β)-17-hydroxy-3-oxo-17-(pentafluoroethyl)estra-4,9-dien-11-yl]-N-(4-methoxyphenyl)benzamide (Ex. 25)

N-(4-chlorophenyl)-4-[(11β,17β)-17-hydroxy-3-oxo-17-(pentafluoroethyl)estra-4,9-dien-11-yl]benzamide (Ex. 26)

4-[(11β,17β)-17-hydroxy-3-oxo-17-(pentafluoroethyl)estra-4,9-dien-11-yl]-N-methyl-N-phenylbenzamide (Ex. 28)

4-[(11β,17β)-17-hydroxy-3-oxo-17-(pentafluoroethyl)estra-4,9-dien-11-yl]-N-methyl-N-(pyridin-2-ylmethyl)benzamide (Ex. 31)

4-[(11β,17β)-17-hydroxy-3-oxo-17-(pentafluoroethyl)estra-4,9-dien-11-yl]-N-methyl-N-(pyridin-3-ylmethyl)benzamide (Ex. 32)

4-[(11β,17β)-17-hydroxy-3-oxo-17-(pentafluoroethyl)estra-4,9-dien-11-yl]-N-methyl-N-(pyridin-4-ylmethyl)benzamide (Ex. 33)

N-benzyl-4-[(11β,17β)-17-hydroxy-3-oxo-17-(pentafluoroethyl)estra-4,9-dien-11-yl]benzamide (Ex. 34)

4-[(11β,17β)-17-hydroxy-3-oxo-17-(pentafluoroethyl)estra-4,9-dien-11-yl]-N-(4-methoxybenzyl)benzamide (Ex. 35)

N-(4-chlorobenzyl)-4-[(11β,17β-17-hydroxy-3-oxo-17-(pentafluoroethyl)estra-4,9-dien-11-yl]benzamide (Ex. 36)

methyl-4-({4-[(11β,17β)-17-hydroxy-3-oxo-17-(pentafluoroethyl)estra-4,9-dien-11-yl]benzoyl}amino)benzoate (Ex. 38)

N-(4-carbamoylphenyl)-4-[(11β,17β)-17-hydroxy-3-oxo-17-(pentafluoroethyl)estra-4,9-dien-11-yl]benzamide (Ex. 41)

4-[(11β,17β)-17-hydroxy-3-oxo-17-(pentafluoroethyl)estra-4,9-dien-11-yl]-N-methyl-N-(2-phenylethyl)benzamide (Ex. 43)

4-[(11β,17β)-17-hydroxy-3-oxo-17-(pentafluoroethyl)estra-4,9-dien-11-yl]-N-methyl-N-[2-(pyridin-2-yl)ethyl]benzamide (Ex. 50)

N-benzyl-4-[(11β,17β)-17-hydroxy-3-oxo-17-(pentafluoroethyl)estra-4,9-dien-11-yl]-N-methylbenzamide (Ex. 51)

N-(4-acetamidophenyl)-4-[(11β,17β)-17-hydroxy-3-oxo-17-(pentafluoroethyl)estra-4,9-dien-11-yl]benzamide (Ex. 52)

4-[(11β,17β)-17-hydroxy-3-oxo-17-(pentafluoroethyl)estra-4,9-dien-11-yl]-N-(3-methoxybenzyl)benzamide (Ex. 53)

4-[(11β,17β)-17-hydroxy-3-oxo-17-(pentafluoroethyl)estra-4,9-dien-11-yl]-N-[2-(pyridin-3-yl)ethyl]benzamide (Ex. 55)

N-(3-chlorobenzyl)-4-[(11β,17β-17-hydroxy-3-oxo-17-(pentafluoroethyl)estra-4,9-dien-11-yl]benzamide (Ex. 56)

methyl-3-({4-[(11β,17β)-17-hydroxy-3-oxo-17-(pentafluoroethyl)estra-4,9-dien-11-yl]benzoyl}amino)benzoate (Ex. 57)

4-[(11β,17β)-17-hydroxy-3-oxo-17-(pentafluoroethyl)estra-4,9-dien-11-yl]-N-methyl-N-[2-(pyridin-4-yl)ethyl]benzamide (Ex. 58)

4-[(11β,17β)-17-hydroxy-3-oxo-17-(pentafluoroethyl)estra-4,9-dien-11-yl]-N-[4-(phenylcarbamoyl)phenyl]benzamide (Ex. 60)

4-[(11β,17β)-17-hydroxy-3-oxo-17-(pentafluoroethyl)estra-4,9-dien-11-yl]-N-[2-(pyridin-2-yl)ethyl]benzamide (Ex. 61)

4-[(11β,17β)-17-hydroxy-3-oxo-17-(pentafluoroethyl)estra-4,9-dien-11-yl]-N-[2-(pyridin-4-yl)ethyl]benzamide (Ex. 64)

4-[(11β,17β)-17-hydroxy-3-oxo-17-(pentafluoroethyl)estra-4,9-dien-11-yl]-N-methyl-N-[2-(pyridin-3-yl)ethyl]benzamide (Ex. 72)

2-({4-[(11β,17β)-17-hydroxy-3-oxo-17-(pentafluoroethyl)estra-4,9-dien-11-yl]benzoyl}amino)benzoic acid (Ex. 76)

3-({4-[(11β,17β)-17-hydroxy-3-oxo-17-(pentafluoroethyl)estra-4,9-dien-11-yl]benzoyl}amino)benzoic acid (Ex. 77)

4-({4-[(11β,17β)-17-hydroxy-3-oxo-17-(pentafluoroethyl)estra-4,9-dien-11-yl]benzoyl}amino)benzoic acid (Ex. 78)

The following compounds are also especially preferred:

4-[(11β,17β)-17-hydroxy-3-oxo-17-(pentafluoroethyl)estra-4,9-dien-11-yl]-N-(2-phenylpropan-2-yl)benzamide (Ex. 17), (11β,17β)-11-[4-(3,4-dihydroisoquinolin-2(1H)-ylcarbonyl)phenyl]-17-hydroxy-17-(pentafluoroethyl)estra-4,9-dien-3-one (Ex. 39).

It was found that the compounds or derivatives according to the invention have good progesterone-antagonizing action. It was found in several clinical studies that treatment with progesterone receptor antagonists (mifepristone, asoprisnil, Proellex) can lead to a significant shrinking of uterine fibroids and a significant reduction of the symptoms associated with these uterine fibroids. Moreover, it was shown in clinical studies that treatment with the aforementioned progesterone receptor antagonists can also significantly reduce the symptoms (especially pains) caused by endometriosis.

The compounds of general formula I and physiologically compatible and pharmaceutically acceptable salts thereof can be formulated by methods known by a person skilled in the art, wherein oral dosage forms to be administered once daily are preferred.

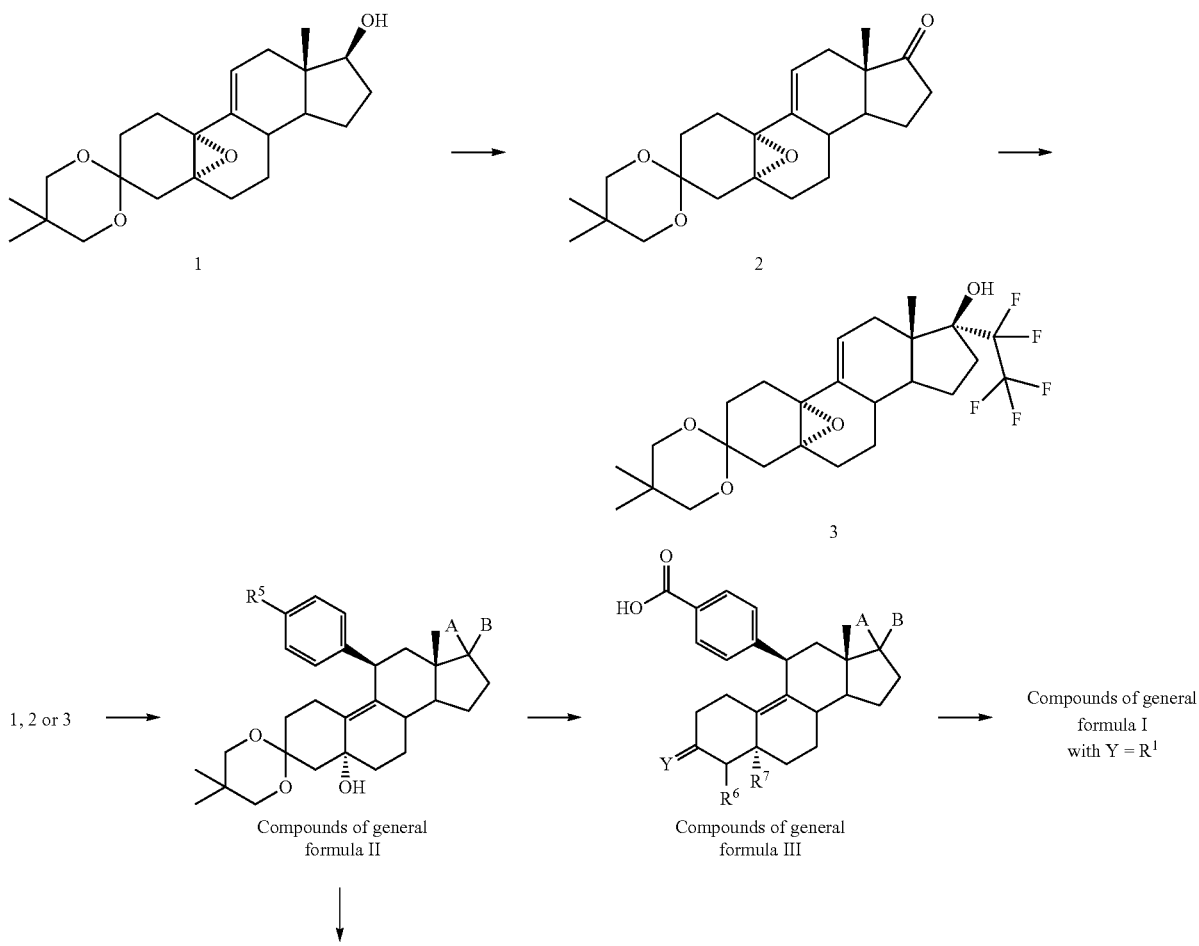

Scheme 1

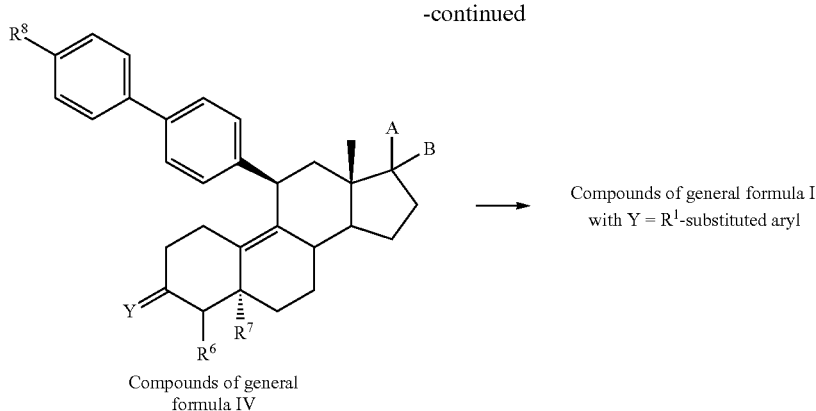

Compounds of general formula IV

→ Compounds of general formula I with Y = R¹-substituted aryl

An overview of the production of compounds of general formula I is shown in Scheme 1. The compounds with the general chemical formula I are prepared starting from (5'R, 8'S,10'R,13'S,14'S,17'S)-5,5,13'-trimethyl-1',2',7',8',12',13', 14',15',16',17'-decahydro-6'H-spiro[1,3-dioxane-2,3'-[5,10] epoxycyclopenta-[a]phenanthren]-17'-ol (compound 1, Scheme 1) (for production see *Tetrahedron Lett.* 26, 2069-2072 (1985)) in analogy to the methods described in WO 98/34947 and in WO 2008/058767. After oxidation of the hydroxyl group in position 17 of the steroid skeleton (compound 2, Scheme 1), the 17β-pentafluoroethyl side chain is introduced onto the corresponding 17-keto compounds according to the methods described in WO 98/34947 and in WO 2008/058767 (compound 3, Scheme 1). The 11β-phenyl substituent is introduced by conjugated addition of aryl-Grignard or aryllithium reagents under copper catalysis. In general, compounds 1, 2 or 3 can be used as starting material for introduction of the 11β-phenyl substituent. Through introduction of the 11β-phenyl substituent, compounds of general formula II are obtained, in which $R^5$ can have all the meanings already given for $R^1$ and additionally can be a protected aldehyde, a carboxy, alkylcarboxy, arylcarboxy, aralkylcarboxy, hydroxymethyl, alkoxymethyl, benzyloxymethyl, alkanoyloxymethyl, silyloxymethyl, hydroxyl, $C_1$-$C_6$-alkoxy, benzyloxy, $C_1$-$C_6$-alkanoyloxy, benzoyloxy, silyloxyl, alkoxyalkyloxy group, a Cl, Br, I or a $C_mF_{m+1}SO_3$ group with m=1-4, and A or B either stands for a carbonyl group or for a 17β—OH/17α-H group or for a 17β-OH/17α-$C_2F_5$ group. The compounds of general formula I can then be obtained from compounds of general formula II in several steps. For this, functional groups are optionally modified further. We may note in particular the production of compounds of general formula I from compounds of general formula III by amidation techniques known by a person skilled in the art. Methods may come into consideration for amidation in which the carboxyl group is converted to an amide directly by reaction with an amine with the aid of known reagents such as 2-(1H-benzotriazol-1-yl)-1,1,3,3-tetramethyluronium tetrafluoroborate (TBTU), 1-hydroxybenzotriazole (HOBt) or 2-propanephosphonic acid anhydride or else first for example an acid chloride is formed from the free carboxylic acid, and is then converted to an amide by reaction with the corresponding amines. Compounds of general formula III are produced from compounds of formula II by oxidation of aldehydes, which are obtained by cleavage of protecting groups that are present, or by single-stage or two-stage oxidation of the hydroxymethyl compounds, which are also released by cleavage of any alcohol protecting groups that are present. Starting from compounds of general formula II, in which $R^5$ stands for a protected aldehyde, for this purpose the aldehyde protecting group is cleaved by methods known by a person skilled in the art. The cleavage of the aldehyde protecting group can take place under reaction conditions in which the ketal protecting group in position 3 of the steroid skeleton is also cleaved to the ketone, but also in mildly acidic conditions in which the protecting group in position 3 is preserved. Starting from compounds of general formula II in which $R^5$ stands for a protected hydroxymethyl group, the alcohol protecting group is cleaved, so that a free hydroxymethyl group is formed. As an alternative, amidation can however also be carried out starting from the alkylcarboxy or arylcarboxy compounds by reaction with the corresponding amines in the presence of trimethylaluminium or comparable Lewis acids. Compounds in which Y has the meaning of an $R^1$-substituted aryl residue (general formula IV), are either produced directly by conjugated addition of the diaryl-Grignard or diaryllithium reagent under copper catalysis or else for example via palladium-catalysed coupling reactions on the corresponding functionalized 11β-phenyl derivatives, e.g. phenyl triflates or phenyl nonaflates. In the introduction of the second aromatic e.g. via palladium-catalysed coupling reactions, $R^8$ can already have the meaning of $R^1$ or else can be produced in the way already described previously, e.g. from carboxyl groups or alkyl- or arylcarboxyl groups. For production of compounds of general formula I, finally any protecting groups still present are cleaved and the residues $R^5$ or $R^8$ are modified further. For these modifications, we may mention oxidations or reductions, esterifications, saponifications, alkylation, acylations of free valences in $R^5$ or $R^8$.

As ketal protecting groups or acetal protecting groups, we may mention for example the ethylenedioxy or the 2,2-dimethylpropylene-1,2-dioxy group. Hydroxyl groups are for example protected in the form of methoxymethyl, methoxyethyl, tetrahydropyranyl, benzyl, or silyl ethers.

During cleavage of the 3-ketal to the 3-keto group of the steroid skeleton, any 5α-hydroxyl group still present is eliminated, so that compounds of general formula I are formed.

If the production of the starting compounds is not described here, these are known by a person skilled in the art or can be produced similarly to known compounds or methods described here. The isomeric mixtures can be separated by usual methods, for example crystallization, chromatography or salt formation, into the individual compounds. Production of the salts takes place in the usual way, by adding the equivalent amount or an excess of a base or acid, which is optionally in solution, to a solution of the compounds with the general chemical formula I, optionally separating the precipitate or working up the solution in the usual way.

The resultant compounds of formula (I) are optionally converted with the corresponding (i) solvents and/or (ii) bases or acids to their solvates, salts and/or solvates of the salts.

The aforementioned general definitions of residues or those given in preferred ranges apply both to the end products of formula (I) and correspondingly also to the starting substances or intermediates required for production in each case.

The compounds according to the invention display an unforeseeable, valuable pharmacological, pharmacokinetic and pharmacodynamic profile of activity.

They are therefore suitable for application as medicinal products for the treatment and/or prevention of diseases in humans and animals.

The pharmaceutical efficacy of the compounds according to the invention can be explained by their action as progesterone receptor antagonists, i.e. their antagonizing action on the progesterone receptor.

The present invention further relates to the use of the compounds according to the invention for the treatment and/or prevention of diseases based on hormone-dependent hyperproliferative processes, preferably gynaecological diseases, in particular uterine fibroids, endometriosis or hormone-dependent breast cancers.

The present invention further relates to the use of the compounds according to the invention for the treatment and/or prevention of diseases, in particular the aforementioned diseases.

The present invention further relates to the compounds according to the invention for use in a method for treating and/or preventing uterine fibroids, endometriosis and hormone-dependent breast cancers.

The present invention further relates to the use of the compounds according to the invention for producing a medicinal product for the treatment and/or prevention of diseases, in particular the aforementioned diseases.

The present invention further relates to a method for treating and/or preventing diseases, in particular the aforementioned diseases, using 0.1-100 mg of the compounds according to the invention per day and per patient in the treatment of uterine fibroids or endometriosis and for contraceptive use or using 0.1-500 mg of the compounds according to the invention per day and per patient in the case of oncoses (e.g. meningioma or hormone-dependent tumours, e.g. breast cancer) and in emergency contraception.

The present invention further relates to medicinal products containing at least one compound according to the invention and at least one or more further active substances, in particular for treating and/or preventing the aforementioned diseases.

For treating oncoses, for example the following active substances/classes of active substances can be administered either simultaneously or sequentially: SERMs, SERDs, anti-oestrogens, aromatase inhibitors, kinase inhibitors, angiogenesis inhibitors and/or cytostatics.

For treating uterine fibroids or endometriosis, the compounds according to the invention can be combined simultaneously or sequentially with gestagens or combinations of oestrogens and gestagens.

Progesterone receptor antagonists/gestagen regimens are disclosed in WO 96/15794 (Spicer et al., Balance Pharm. Inc.), WO 96/03130 (Stöckemann et al., Schering AG) and PCT/EP2009/003249 (Möller et al., Bayer Schering Pharma AG). Regimens—optionally repeated—in which the progesterone receptor antagonist is administered for a period of two to four months, followed by administration of the gestagen for a period of one to four weeks, are very suitable for the treatment of uterine fibroids and endometriosis. Optionally repeated administration of the progesterone receptor antagonist for 84 days followed by administration of the gestagen for 14 days is particularly suitable.

For treating menopause-associated complaints, consideration may be given to simultaneous or sequential administration of the compounds according to the invention e.g. with SERMs, SERDs and oestrogens.

SERMs (selective oestrogen receptor modulators) are compounds that have either an anti-oestrogenic or oestrogenic action that is tissue-selective, for example on the uterus they inhibit the action of oestrogen, but on bone they have a neutral or oestrogen-like action. Examples are clomifene, raloxifene, tamoxifen, toremifene, bazedoxifene, lasofoxifene and ormeloxifene.

Selective oestrogen receptor destabilizers (SERDs) are drugs that completely antagonize the oestrogen receptor ('pure anti-oestrogens' without oestrogenic active components) and lead to degradation of the receptor (for example fulvestrant, ZK-703 and ZK-253 (Hoffmann J et al., J Natl Cancer Inst 2004, 96:210-218) and compounds described in WO 98/007740, WO 99/33855 and WO 03/045972.

Anti-oestrogens are compounds that completely antagonize the oestrogen receptor, for example fulvestrant.

Aromatase inhibitors inhibit the enzyme aromatase and therefore the aromatization of androgens to oestrogens. These include, among others, anastrozole, letrozole, exemestane, vorozole, formestane and fadrozole.

Kinase inhibitors are enzymes that transfer a phosphate residue from ATP to other substrates, there in particular onto hydroxyl groups, e.g. sorafenib (Nexavar) or imatinib (Gleevec).

Angiogenesis inhibitors, e.g. Avastin, reduce or block vascularization and hence blood supply to a tumour.

Cytostatics, e.g. cisplatin, taxol, Taxotere are natural or synthetic substances that inhibit cell growth or cell division.

Gestagens are to be understood, in the sense of the present invention, either as natural progesterone itself, or synthetic derivatives which, like progesterone itself, bind to the progesterone receptor and, at doses that are above the ovulation inhibiting dose, inhibit ovulation. Drospirenone, gestodene, levonorgestrel, cyproterone acetate, desogestrel and 3-ketodesogestrel, norethisterone, norethisterone acetate and dienogest may be mentioned as examples of the synthetic derivatives.

Combinations of gestagens and oestrogens are the combinations of active substances that are contained in the oral contraceptives that are known per se, for example Yasmin, Femovan, Triquilar, Marvelon, YAZ etc.

The compounds according to the invention can act systemically and/or locally. For this purpose, they can be applied by a suitable route, e.g. oral, intrauterine, intravaginal, parenteral, pulmonary, nasal, sublingual, lingual, buccal, rectal, dermal, transdermal, conjunctival, otic or as implant or stent.

Intrauterine means, in particular, application by means of IUS (intrauterine system) or IUD (intrauterine device). Intravaginal application can be effected inter alia by means of IVR/VRS (intravaginal ring/vaginal ring system).

Intrauterine or intravaginal application forms (cf. e.g. WO 01/47490, in particular page 1, line 10 to page 5, line 13 and page 7, line 19 to page 58, line 6, or for vaginal rings: WO 06/010097, in particular page 10, line 22 to page 14, line 28) can contain the compounds according to the invention and non-silicone and/or silicone polymers, in particular also siloxane-based elastomers (cf. WO 01/47490, in particular page 7, line 19-page 15, line 15).

For these routes of application, the compounds according to the invention can be administered in suitable dosage forms.

Dosage forms functioning according to the state of the art, providing rapid and/or modified release of the compounds according to the invention, which contain the compounds according to the invention in crystalline and/or amorphized and/or dissolved form, for example tablets (uncoated or coated tablets, for example with enteric coatings or delayed-release or insoluble coatings, which control the release of the compound according to the invention), tablets that disintegrate quickly in the oral cavity, or films/wafers, films/lyophilizates, capsules (for example hard-gelatin or soft-gelatin capsules), sugar-coated tablets, granules, pellets, powders, emulsions, suspensions, aerosols or solutions, are suitable for oral application.

Parenteral application can take place with avoidance of an absorption step (e.g. by intravenous, intraarterial, intracardiac, intraspinal or intralumbar administration) or with inclusion of absorption (e.g. intramuscular, subcutaneous, intracutaneous, percutaneous or intraperitoneal administration). Dosage forms suitable for parenteral application include injection and infusion preparations in the form of solutions, suspensions, emulsions, lyophilizates or sterile powders.

Pharmaceutical forms suitable for the other routes of application are for example inhalation dosage forms (including powder inhalers, nebulizers), nasal drops, solutions, and sprays; tablets for lingual, sublingual or buccal application, films/wafers or capsules, suppositories, ear or eye preparations, vaginal capsules, aqueous suspensions (lotions, shaking mixtures), lipophilic suspensions, ointments, creams, transdermal therapeutic systems (for example patches), milk, pastes, foams, dusting powder, implants or stents.

The compounds according to the invention can be transformed into the aforementioned dosage forms. This can take place in a manner known per se by mixing with inert, non-toxic, pharmaceutically suitable excipients. These excipients include, among others, carriers (for example microcrystalline cellulose, lactose, mannitol), solvents (e.g. liquid polyethylene glycols), emulsifiers and dispersants or wetting agents (for example sodium dodecyl sulphate, polyoxysorbitan oleate), binders (for example polyvinylpyrrolidone), synthetic and natural polymers (for example albumin), stabilizers (e.g. antioxidants, such as ascorbic acid), colorants (e.g. inorganic pigments, such as iron oxides) and taste and/or odour correctants.

The present invention further relates to medicinal products that contain at least one compound according to the invention, usually together with one or more inert, non-toxic, pharmaceutically suitable excipients, and use thereof for the aforementioned purposes.

Nevertheless, it may optionally be necessary to deviate from the stated amounts, namely depending on body weight, route of administration, individual response to the active substance, type of preparation and time point or interval when application takes place. Thus, in some cases it may be sufficient to use less than the aforementioned minimum amount, whereas in other cases the stated upper limit must be exceeded. In the case of application of larger amounts, it may be advisable to divide these into several individual doses, distributed over the day.

The percentages in the following tests and examples are, unless stated otherwise, percentages by weight; parts are parts by weight. Solvent ratios, dilution ratios and concentration figures for liquid/liquid solutions refer in each case to volume.

The following examples serve for explanation of the invention without limiting it in any way.

EXAMPLE 1

4-[(11β,17β)-17-Hydroxy-3-oxo-17-(pentafluoroethyl)estra-4,9-dien-11-yl]benzamide

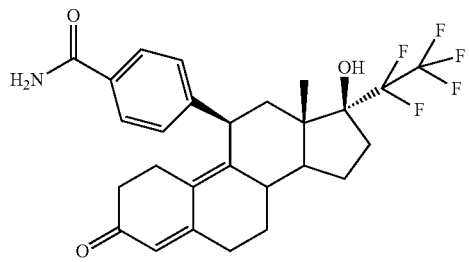 [SMILES: C[C@]12C[C@H](c3ccc(C(N)=O)cc3)C3=C4CCC(=O)C=C4CCC3C1CC[C@@]2(O)C(F)(F)C(F)(F)F]

a) (5'R,8'S,10'R,13'S,14'S,17'S)-5,5,13'-trimethyl-17'-(pentafluoroethyl)-1',2',7',8',12',13',14',15',16',17'-decahydro-6'H-spiro[1,3-dioxane-2,3'-[5,10]epoxycyclopenta[a]phenanthren]-17'-ol

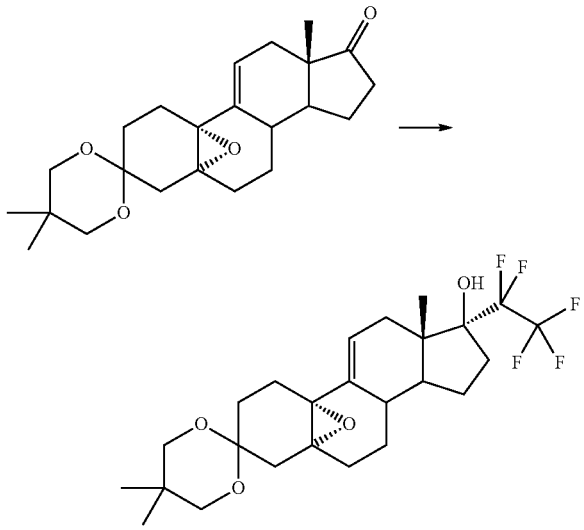

50 g of (5'R,8'S,10'R,13'S,14'S)-5,5,13'-trimethyl-1',2',6',7',8',12',13',14',15',16'-decahydro-17'H-spiro[1,3-dioxane-2,3'-[5,10]epoxycyclopenta[a]phenanthren]-17'-one (for production see Tetrahedron Lett. 26, 2069-2072 (1985)) was added to 116 g of condensed pentafluoroiodoethane in 500 ml absolute toluene at −70° C. At the same temperature, 290 ml of 1.5 molar solution of methyllithium-lithium bromide complex in diethyl ether was added. Then it was stirred for a further hour at 0° C. Then the reaction mixture was added to saturated aqueous ammonium chloride solution and was extracted with ethyl acetate. The organic phase was washed with saturated aqueous sodium chloride solution, dried over sodium sulphate and concentrated under vacuum. The raw product was dissolved in 200 ml acetone and 450 ml water was added. The precipitated product was filtered off and dried in vacuum.

Yield 61.6 g

¹H NMR (400 MHz, CDCl₃): δ=6.04 brd (1H); 3.60 d (1H); 3.35-3.50 m (3H); 2.51 dbr (1H); 1.06 s (3H); 0.93 s (3H); 0.85 s (3H).

1b) (5R,8S,11R,13S,14S,17S)-11-[4-({[tert-butyl(dimethyl)silyl]oxy}methyl)phenyl]-5',5',13-trimethyl-17-(pentafluoroethyl)-1,2,6,7,8,11,12,13,14,15,16,17-dodecahydrospiro[cyclopenta[a]phenanthrene-3,2'-[1,3]dioxane]-5,17(4H)-diol

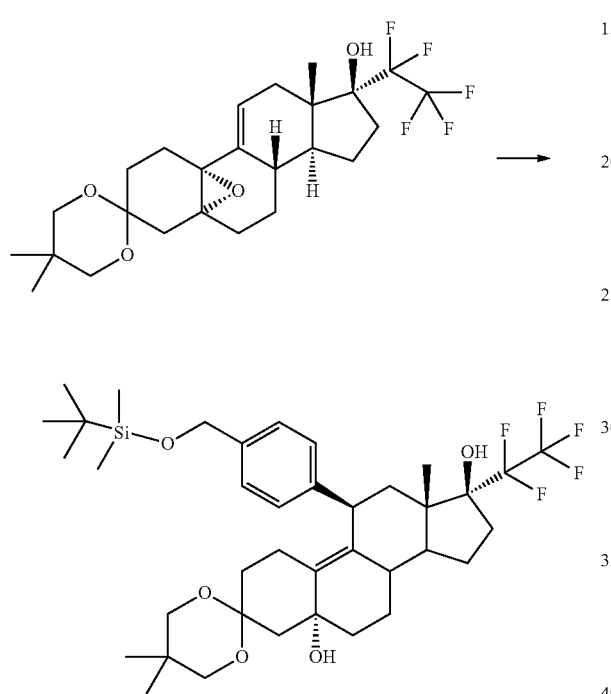

1.23 g of magnesium chips were suspended in 5 ml tetrahydrofuran and 50 μl dibromoethane was added, with stirring. A solution of 15.29 g of [(4-bromobenzyl)oxy]-(tert-butyl)dimethylsilane in 40 ml tetrahydrofuran was added to the suspension at such a rate that the internal temperature did not exceed 60° C. Then it was stirred for one hour at 23° C. Then the resultant solution was cooled to 0° C. 151 mg of copper(I) chloride was added and it was stirred for a further 15 minutes at 0° C. Then a solution of 5 g of the substance described in example 1a) in 50 ml tetrahydrofuran was added. Then the reaction mixture was allowed to reach 23° C. with stirring for approx. 3 hours and then it was stirred at this temperature for a further 10 hours. Then saturated aqueous ammonium chloride solution was added to the reaction mixture with external cooling. It was stirred for a further 30 minutes and was then extracted several times with ethyl acetate. The combined organic phases were washed with saturated sodium chloride solution and dried over sodium sulphate. The raw product was purified by silica gel chromatography. 5.62 g of the title compound was obtained.

¹H NMR (300 MHz, CDCl₃): δ=7.10-7.22 m (4H); 4.70 s (2H); 4.43 s (1H); 4.30 dbr (1H); 3.40-3.56 m (4H); 1.06 s (3H); 0.91 s (9H); 0.86 s (3H); 0.50 s (3H); 0.08 s (6H).

c) (5R,8S,11R,13S,14S,17S)-11-[4-(hydroxymethyl)phenyl]-5',5',13-trimethyl-17-(pentafluoroethyl)-1,2,6,7,8,11,12,13,14,15,16,17-dodecahydrospiro[cyclopenta[a]phenanthrene-3,2'-[1,3]dioxane]-5,17(4H)-diol

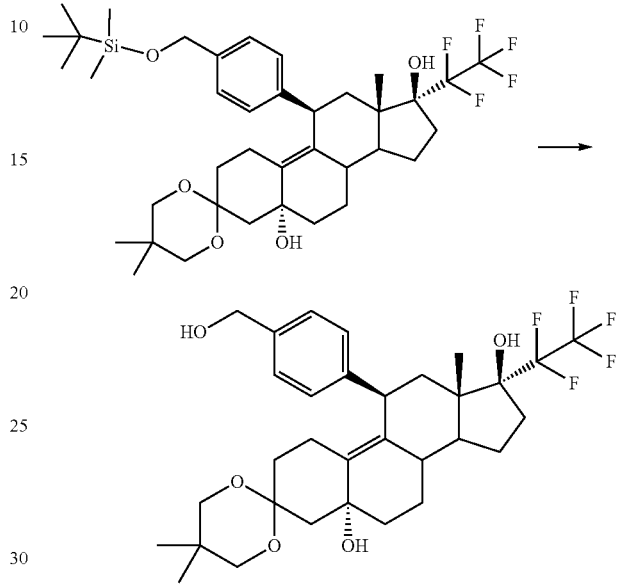

2.99 g of the compound described in example 1b) was dissolved in 25 ml tetrahydrofuran. 6.3 ml of a 1-molar solution of tetrabutylammonium fluoride in tetrahydrofuran was added and it was then stirred for a further 2.5 hours at 23° C. Then the reaction mixture was poured into saturated sodium hydrogen carbonate solution. It was extracted with ethyl acetate several times. The combined organic phases were washed with saturated sodium chloride solution and dried over sodium sulphate. The raw product was purified by silica gel chromatography. 2.5 g of the title compound was obtained.

¹H NMR (400 MHz, CDCl₃): δ=7.18-7.30 m (4H); 4.66 d (2H); 4.42 s (1H); 4.30 dbr (1H); 3.40-3.58 m (4H); 1.03 s (3H); 0.87 s (3H); 0.51 s (3H).

d) 4-[(5R,8S,11R,13S,14S,17S)-5,17-dihydroxy-5,5,13-trimethyl-17-(pentafluoroethyl)-1,2,4,5,6,7,8,11,12,13,14,15,16,17-tetradecahydrospiro[cyclopenta[a]phenanthrene-3,2'-[1,3]dioxan-11-yl]benzaldehyde

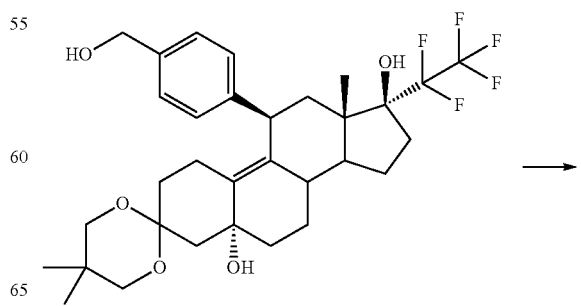

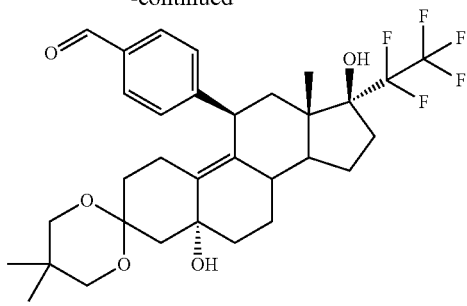

735 mg of N-methylmorpholine-N-oxide, 58 mg of tetrabutylammonium perruthenate and a small amount of molecular sieve (4 Å) were added to a solution of 2.51 g of the compound described in 1c) in 30 ml dichloromethane. It was stirred for 3.5 hours at 23° C. Then the reaction mixture was filtered on a small amount of silica gel and concentrated under vacuum. The raw product obtained was purified by silica gel chromatography. 2.35 g of the title compound was obtained.

$^1$H NMR (400 MHz, CDCl$_3$): δ=9.95 s (1H); 7.79 d (2H); 7.40 d (2H); 4.44 s (1H); 4.39 dbr (1H); 3.40-3.60 m (4H); 1.04 s (3H); 0.87 s (3H); 0.50 s (3H).

e) 4-[(5R,8S,11R,13S,14S,17S)-5,17-dihydroxy-5',5',13-trimethyl-17-(pentafluoroethyl)-1,2,4,5,6,7,8,11,12,13,14,15,16,17-tetradecahydrospiro[cyclopenta[a]phenanthrene-3,2'-[1,3]dioxan]-11-yl] benzoic acid

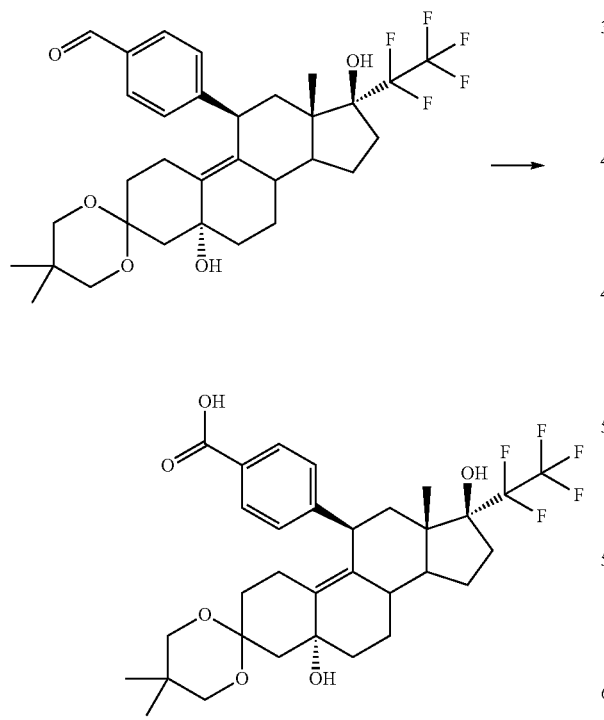

66 ml of tert-butanol and a mixture of 11 ml of 2-methyl-2-butene and 50 ml tetrahydrofuran were added to 1.09 g of the compound described in 1d). It was cooled to 0° C. Then, while stirring vigorously, 13.9 ml water, 1.02 g sodium chlorite and 755 mg sodium hydrogen phosphate monohydrate were added. It was stirred for 3.5 hours at 0° C. Then the reaction mixture was poured carefully into saturated sodium thiosulphate solution. It was extracted with ethyl acetate several times. The combined organic phases were washed with saturated sodium chloride solution and dried over sodium sulphate. The raw product was purified by silica gel chromatography. 839 mg of the title compound was obtained.

$^1$H NMR (300 MHz, CDCl$_3$): δ=8.00 d (2H); 7.32 d (2H); 4.40 dbr (1H); 3.40-3.60 m (4H); 1.05 s (3H); 0.86 s (3H); 0.50 s (3H).

f) methyl-4-[(5R,8S,11R,13S,14S,17S)-5,17-dihydroxy-5',5',13-trimethyl-17-(pentafluoroethyl)-1,2,4,5,6,7,8,11,12,13,14,15,16,17-tetradecahydrospiro[cyclopenta[a]phenanthrene-3,2'-[1,3]dioxan]-11-yl] benzoate 833 mg of the compound described in 1e) was dissolved in a mixture of 17 ml tetrahydrofuran and 3.6 ml methanol. 773 µl of a 2-molar solution of (trimethylsilyl)diazomethane in diethyl ether was added dropwise to this solution. It was stirred for 1.5 hours at 23° C. Then the reaction mixture was concentrated under vacuum. The raw product obtained was purified by silica gel chromatography. 720 mg of the title compound was obtained.

$^1$H NMR (300 MHz, CDCl$_3$): δ=7.93 d (2H); 7.29 d (2H); 4.43 s (1H); 4.36 dbr (1H); 3.90 s (3H); 3.35-3.60 m (4H); 1.06 s (3H); 0.86 s (3H); 0.51 s (3H).

g) 4-[(5R,11R,13S,17S)-5,17-dihydroxy-5,5,13-trimethyl-17-(pentafluoroethyl)-1,2,4,5,6,7,8,11,12,13,14,15,16,17-tetradecahydrospiro[cyclopenta[a]phenanthrene-3,2'-[1,3]dioxan]-11-yl]benzamide

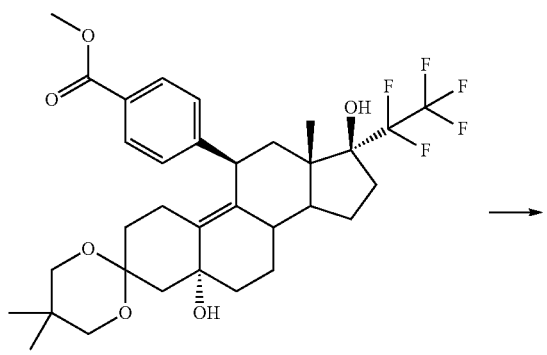

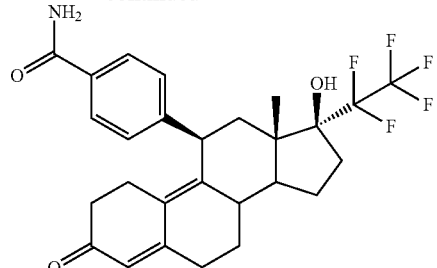

260 mg of the compound described in 1 g) was dissolved in 6 ml methanol. 190 µl of semi-concentrated sulphuric acid was added and it was stirred for 3 hours at 23° C. Then the reaction mixture was poured into saturated aqueous sodium hydrogen carbonate solution. It was extracted with ethyl acetate several times. The combined organic phases were washed with saturated aqueous sodium chloride solution, dried over sodium sulphate and concentrated under vacuum. The raw product was purified by silica gel chromatography. 186 mg of the title compound was obtained.

$^1$H NMR (400 MHz, CDCl$_3$): δ=7.73 d (2H); 7.28 d (2H); 6.10 sbr (1H); 5.80 sbr (1H); 5.64 sbr (1H); 4.48 dbr (1H); 0.56 s (3H).

EXAMPLE 2

4-[(11β,17β)-17-Hydroxy-3-oxo-17-(pentafluoroethyl)estra-4,9-dien-11-yl]-N,N-dimethylbenzamide

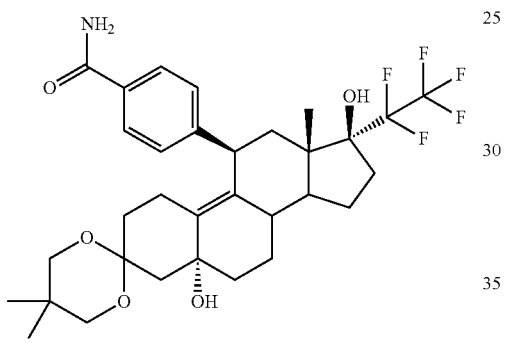

9 ml of a 7-molar methanolic ammonia solution was added to 554 mg of the compound described in 1f). The reaction mixture was stirred in a bomb tube for 4 days at 85° C. After cooling, it was concentrated under vacuum. The raw product obtained was purified by silica gel chromatography. 270 mg of the title compound was obtained.

$^1$H NMR (300 MHz, CDCl$_3$): δ=7.70 d (2H); 7.30 d (2H); 6.02 sbr (1H); 5.61 sbr (1H); 4.43 s (1H); 4.36 dbr (1H); 3.40-3.62 m (4H); 1.03 s (3H); 9.87 s (3H); 0.50 s (3H).

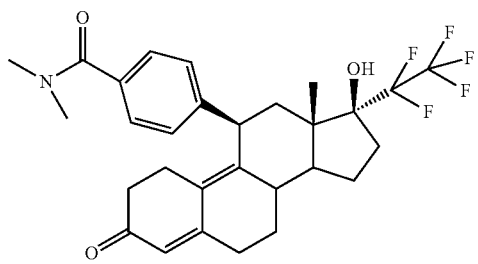 [SMILES: CN(C)C(=O)c1ccc([C@H]2C[C@@]3(C)C(CC[C@@]3(O)C(F)(F)C(F)(F)F)C3CCC4=CC(=O)CCC4=C32)cc1]

h) 4-[(11β,17β)-17-hydroxy-3-oxo-17-(pentafluoroethyl)estra-4,9-dien-11-yl]benzamide a) (5R,8S,11R,13S,14S,17S)-11-[4-(dimethoxymethyl)phenyl]-5',5',13-trimethyl-17-(pentafluoroethyl)-1,2,6,7,8,11,12,13,14,15,16,17-dodecahydrospiro[cyclopenta[a]phenanthrene-3,2'-[1,3]dioxane]-5,17(4H)-diol

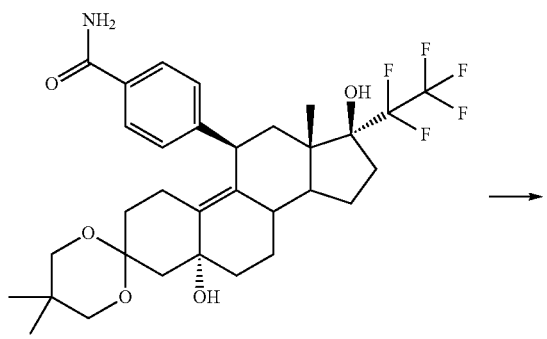

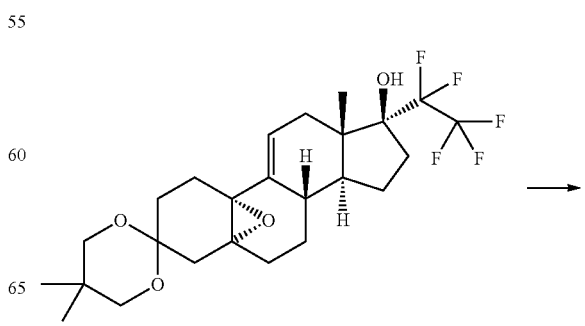

-continued

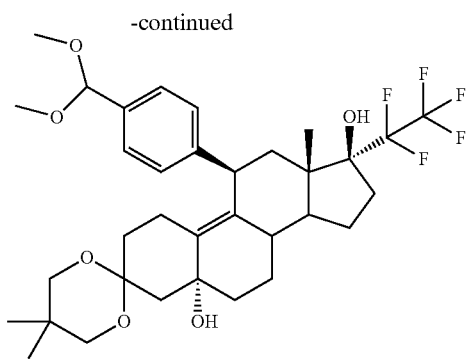

1.48 g of magnesium chips were suspended in 5 ml tetrahydrofuran and 50 μl of dibromoethane was added, with stirring. A solution of 10.18 ml of 1-bromo-4-(dimethoxymethyl)benzene in 70 ml tetrahydrofuran was added to the suspension at 40° C. Then it was stirred for one hour at 50° C. Then the resultant solution was cooled to 0° C. 40 mg of copper(I) chloride was added and it was stirred for a further 15 minutes at 0° C. Then a solution of 5 g of the substance described in example 1a) in 50 ml tetrahydrofuran was added. Then the reaction mixture was allowed to reach 23° C. with stirring for approx. 3 hours and then it was stirred at this temperature for a further 10 hours. Then saturated aqueous ammonium chloride solution was added to the reaction mixture, with external cooling. It was stirred for a further 30 minutes and was then extracted several times with ethyl acetate. The combined organic phases were washed with saturated sodium chloride solution and dried over sodium sulphate. The raw product was purified by silica gel chromatography. 6.4 g of the title compound was obtained.

$^1$H NMR (400 MHz, CDCl$_3$): δ=7.32 d (2H); 7.21 d (2H); 5.36 s (1H); 4.43 s (1H); 4.32 dbr (1H); 3.39-3.58 m (4H); 3.31 s (6H); 1.03 s (3H); 0.86 s (3H); 0.51 s (3H).

b) 4-[(11β,17β-17-hydroxy-3-oxo-17-(pentafluoroethyl)estra-4,9-dien-11-yl]benzaldehyde

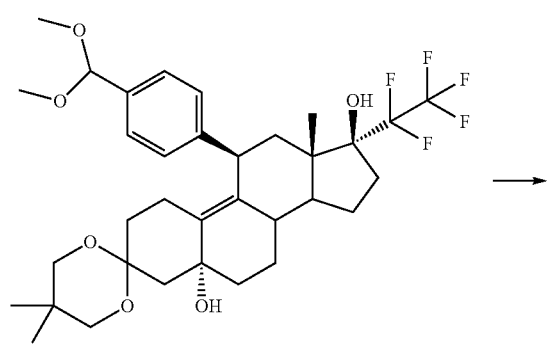

3.5 g of the compound described in 2a) was dissolved in 55 ml of 70% acetic acid. It was stirred for 16 hours at 30° C. Then the reaction mixture was poured into water. It was stirred for a further 5 hours. Then it was filtered. The residue was washed with water, dried and purified by silica gel chromatography. 2.2 g of the title compound was obtained.

$^1$H NMR (300 MHz, CDCl$_3$): δ=9.99 s (1H); 7.80 d (2H); 7.37 d (2H); 5.80 sbr (1H); 4.51 dbr (1H); 0.58 s (3H).

c) 4-[(11β,17β-17-hydroxy-3-oxo-17-(pentafluoroethyl)estra-4,9-dien-11-yl]benzoic acid

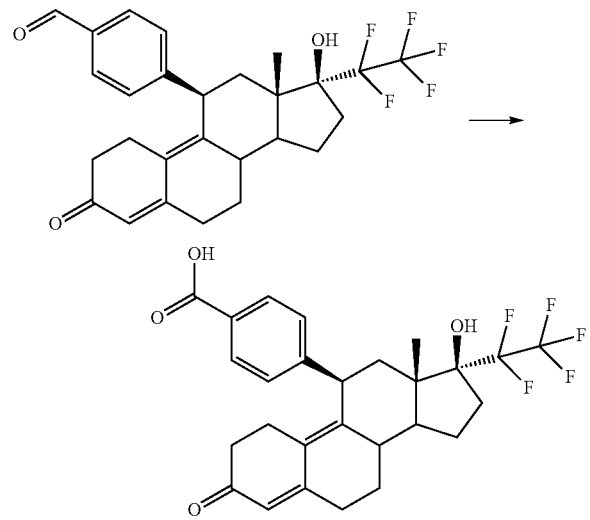

At −15° C., 910 μl of 8N chromosulphuric acid (Jones reagent) was added to a solution of 1.2 g of the compound described in example 2b) in 40 ml acetone. It was stirred for 4.5 hours at 0° C. and then the reaction mixture was poured into 300 ml of ice-cold saturated sodium chloride solution. It was stirred for 12 hours and then the precipitated reaction product was filtered off. The raw product was purified by silica gel chromatography. 989 mg of the title compound was obtained.

$^1$H NMR (400 MHz, CDCl$_3$): δ=8.00 d (2H); 7.30 d (2H); 5.80 sbr (1H); 4.50 dbr (1H); 0.59 s (3H).

d) 4-[(11β,17β)-17-hydroxy-3-oxo-17-(pentafluoroethyl)estra-4,9-dien-11-yl]-N,N-dimethylbenzamide -continued

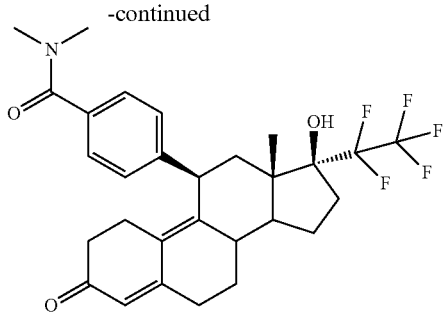

20 µl triethylamine, 6.9 µl dimethylamine and 43 mg of 2-(1H-benzotriazol-1-yl)-1,1,3,3-tetramethyluronium tetrafluoroborate (TBTU) were added to a solution of 60 mg of the compound described in example 2c) in 2 ml of N,N-dimethylformamide. The reaction mixture was stirred for 16 hours at 23° C. and was then diluted with 50 ml ethyl acetate. The solution was washed with saturated sodium hydrogen carbonate solution and saturated sodium chloride solution and dried over sodium sulphate. The raw product was purified by silica gel chromatography. 48 mg of the title compound was obtained.

$^1$H NMR (300 MHz, CDCl$_3$): δ=7.39 d (2H); 7.25 d (2H); 5.83 sbr (1H); 4.51 dbr (1H); 3.12 sbr (3H); 3.03 sbr (3H); 0.60 s (3H).

Examples 3-10 were synthesized similarly to example 2d from the compound described in 2c) and the respective amine:

| Ex. | Structure | Name | $^1$H NMR |
|---|---|---|---|
| 3 | 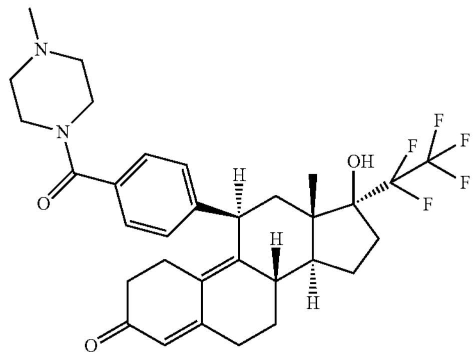 | (11β,17β)-17-hydroxy-11-{4-[(4-methylpiperazin-1-yl)carbonyl]phenyl}-17-(pentafluoroethyl)estra-4,9-dien-3-one | $^1$H NMR (300 MHz, CDCl$_3$): δ = 7.32 d (2H); 7.21 d (2H); 5.79 sbr (1H); 4.46 dbr (1H); 3.78 m (2H); 3.43 m (2H); 2.30 s (3H); 0.56 s (3H). |
| 4 | 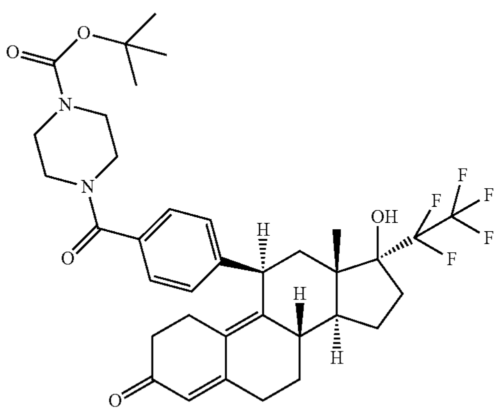 | tert-butyl-4-{4-[(11β,17β)-17-hydroxy-3-oxo-17-(pentafluoroethyl)estra-4,9-dien-11-yl]benzoyl}piperazine-1-carboxylate | $^1$H NMR (300 MHz, CDCl$_3$): δ = 7.38 d (2H); 7.26 d (2H); 5.84 sbr (1H); 4.50 dbr (1H); 3.35-3.85 m (8H); 1.52 s (9H); 0.61 s (3H). |
| 5 | 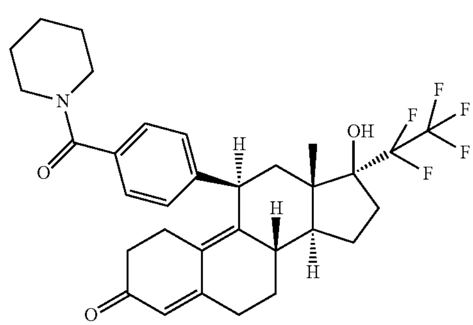 | (11β,17β)-17-hydroxy-17-(pentafluoroethyl)-11-[4-(piperidin-1-ylcarbonyl)phenyl]estra-4,9-dien-3-one | $^1$H NMR (300 MHz, CDCl$_3$): δ = 7.35 d (2H); 7.25 d (2H); 5.84 sbr (1H); 4.50 dbr (1H); 3.73 m (2H); 3.39 m (2H); 0.61 s (3H). |

| Ex. | Structure | Name | ¹H NMR |
|---|---|---|---|
| 6 | 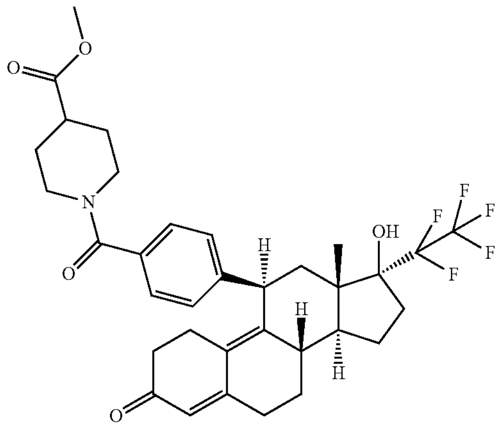 | methyl-1-{4-[(11β,17β)-17-hydroxy-3-oxo-17-(pentafluoroethyl)estra-4,9-dien-11-yl]benzoyl}piperidine-4-carboxylate | ¹H NMR (300 MHz, CDCl₃): δ = 7.31 d (2H); 7.21 d (2H); 5.79 sbr (1H); 4.46 dbr (1H); 3.70 s (3H); 0.58 s (3H). |
| 7 | 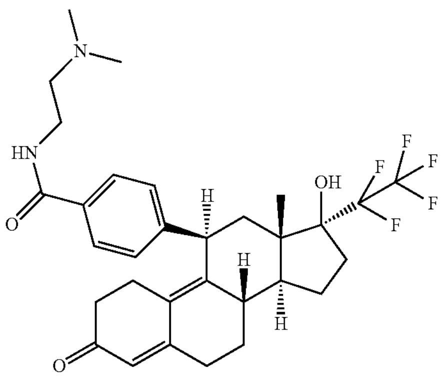 | N-[2-(dimethylamino)ethyl]-4-[(11β,17β)-17-hydroxy-3-oxo-17-(pentafluoroethyl)estra-4,9-dien-11-yl]benzamide | ¹H NMR (400 MHz, CDCl₃): δ = 7.74 d (2H); 7.28 d (2H); 7.09 t (1H); 5.79 sbr (1H); 4.48 dbr (1H); 3.51 m (2H); 2.29 s (6H); 0.59 s (3H). |
| 8 | 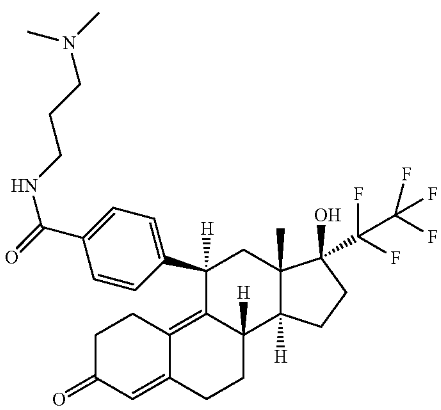 | N-[3-(dimethylamino)propyl]-4-[(11β,17β)-17-hydroxy-3-oxo-17-(pentafluoroethyl)estra-4,9-dien-11-yl]benzamide | ¹H NMR (300 MHz, CDCl₃): δ = 8.36 t (1H); 7.70 d (2H); 7.27 d (2H); 5.79 sbr (1H); 4.48 dbr (1H); 3.54 m (2H); 2.33 s (6H); 0.58 s (3H). |
| 9 | 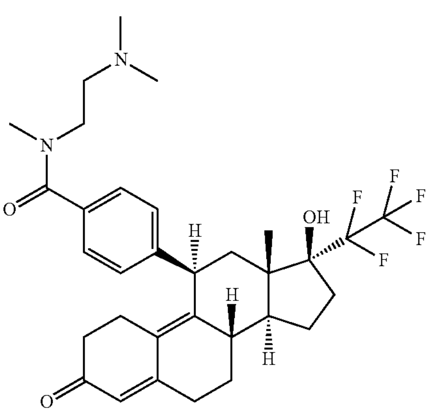 | N-[2-(dimethylamino)ethyl]-4-[(11β,17β)-17-hydroxy-3-oxo-17-(pentafluoroethyl)estra-4,9-dien-11-yl]-N-methylbenzamide | ¹H NMR (300 MHz, CDCl₃): δ = 7.34 d (2H); 7.20 d (2H); 5.79 sbr (1H); 4.45 dbr (1H); 3.05 m (3H); 2.30 m (6H); 0.55 s (3H). |

| Ex. | Structure | Name | ¹H NMR |
|---|---|---|---|
| 10 | 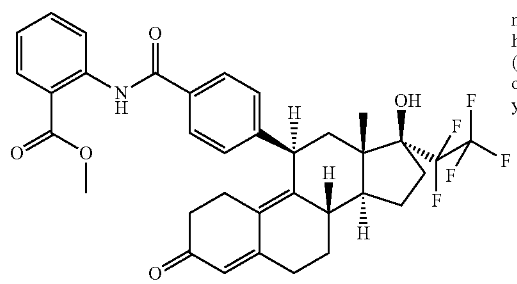 | methyl-2-({4-[(11β,17β)-17-hydroxy-3-oxo-17-(pentafluoroethyl)estra-4,9-dien-11-yl]benzoyl}amino)benzoate | ¹H NMR (400 MHz, CDCl₃): δ = 8.92 d (1H); 8.09 d (1H); 7.99 d (2H); 7.61 tbr (1H); 7.33 d (2H); 7.12 tbr (1H); 5.80 sbr (1H); 4.52 dbr (1H); 3.97 s (3H); 0.60 s (3H). |

Examples 11-72 were produced according to the following specification by parallel synthesis:

The carboxylic acid (0.4 mL of a 0.5 M suspension in DMF, 0.2 mmol, 1 eq.) was placed under protective gas at 20° C., the amine (0.5 mL of a 0.5 M solution in DMF, 0.25 mmol, 1.25 eq.) and diisopropylethylamine (0.175 mL, 1 mmol, 5 eq.) were added in succession, with stirring, it was cooled to 0° C. and finally 2-propanephosphonic acid anhydride (0.23 mL of a 50% solution in DMF, 0.39 mmol, 1.95 eq.) was added. After a further 10 min at 0° C., it was heated to 20° C. and stirred for 10 h at 20° C. For working-up, the reaction mixture was diluted with methanol (3 mL), transferred and concentrated. The residue was dissolved in 1 mL DMSO and 1 mL acetonitrile/water 9:1, any precipitate was filtered off, the solution was purified by HPLC and analysed by HPLC-MS (Waters HPLC 1525µ Binary HPLC, Micromass ZQ, MUX UV 2488, wavelength 210-350 nm, column Waters XBridge C18 3.5 µM, 4.6×50 mm, gradient: 1-99% acetonitrile in 0.1% trifluoroacetic acid/water, flow rate 2 mL/min, run time 8 min).

| Ex. | Structure | Name | HPLC-MS (MH⁺, RT) |
|---|---|---|---|
| 11 | 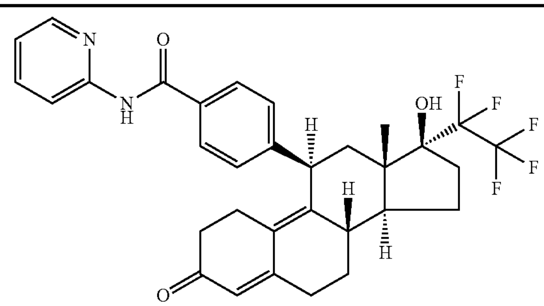 | 4-[(11β,17β)-17-hydroxy-3-oxo-17-(pentafluoroethyl)estra-4,9-dien-11-yl]-N-(pyridin-2-yl)benzamide | 587, 4.25 min. |
| 12 | 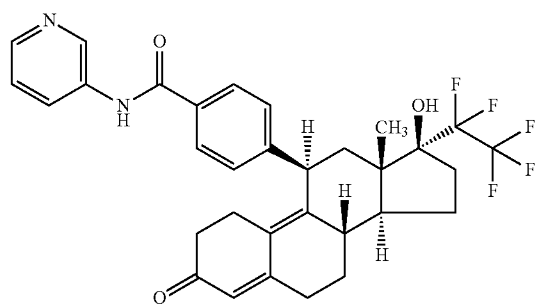 | 4-[(11β,17β)-17-hydroxy-3-oxo-17-(pentafluoroethyl)estra-4,9-dien-11-yl]-N-(pyridin-3-yl)benzamide | 587, 3.71 min. |
| 13 | 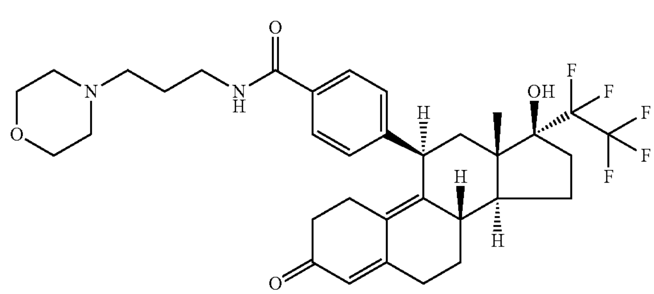 | 4-[(11β,17β)-17-hydroxy-3-oxo-17-(pentafluoroethyl)estra-4,9-dien-11-yl]-N-[3-(morpholin-4-yl)propyl]benzamide | 637, 3.15 min. |

-continued

| Ex. | Structure | Name | HPLC-MS (MH+, RT) |
|---|---|---|---|
| 14 | 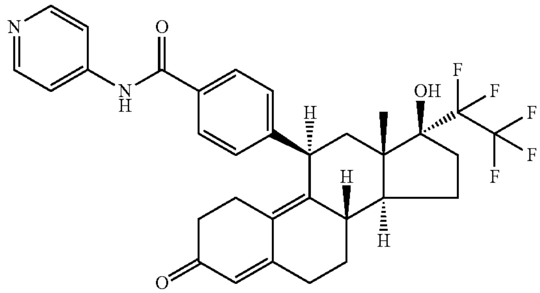 | 4-[(11β,17β)-17-hydroxy-3-oxo-17-(pentafluoroethyl)estra-4,9-dien-11-yl]-N-(pyridin-4-yl)benzamide | 587, 3.31 min. |
| 15 | 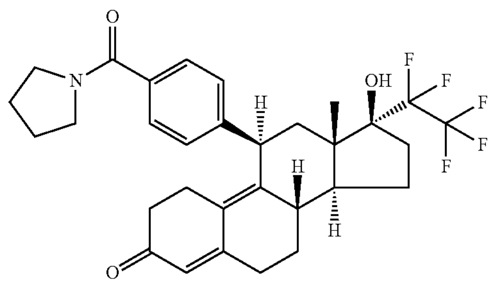 | (11β,17β)-17-hydroxy-17-(pentafluoroethyl)-11-[4-(pyrrolidin-1-ylcarbonyl)phenyl]estra-4,9-dien-3-one | 564, 4.20 min. |
| 16 | 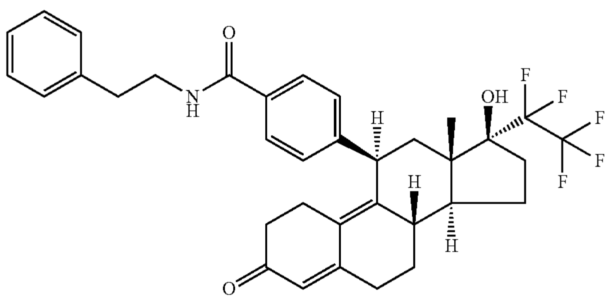 | 4-[(11β,17β)-17-hydroxy-3-oxo-17-(pentafluoroethyl)estra-4,9-dien-11-yl]-N-(2-phenylethyl)benzamide | 614, 4.56 min. |
| 17 | 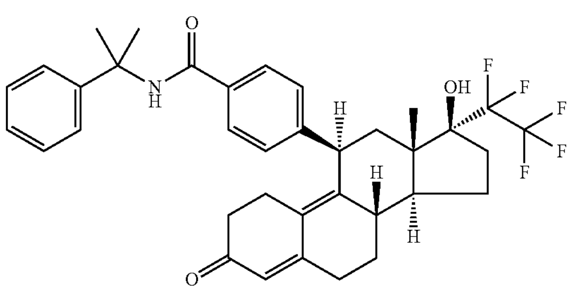 | 4-[(11β,17β)-17-hydroxy-3-oxo-17-(pentafluoroethyl)estra-4,9-dien-11-yl]-N-(2-phenylpropan-2-yl)benzamide | 628, 4.75 min. |
| 18 | 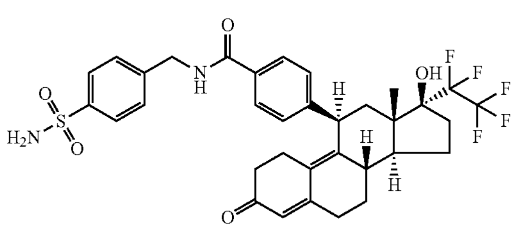 | 4-[(11β,17β)-17-hydroxy-3-oxo-17-(pentafluoroethyl)estra-4,9-dien-11-yl]-N-(4-sulphamoylbenzyl)benzamide | 679, 4.07 min. |

-continued

| Ex. | Structure | Name | HPLC-MS (MH+, RT) |
|---|---|---|---|
| 19 | 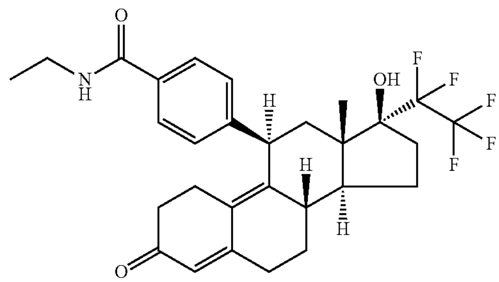 | N-ethyl-4-[(11β,17β)-17-hydroxy-3-oxo-17-(pentafluoroethyl)estra-4,9-dien-11-yl]benzamide | 538, 4.08 min. |
| 20 | 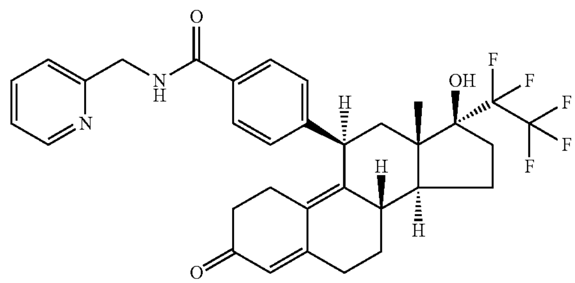 | 4-[(11β,17β)-17-hydroxy-3-oxo-17-(pentafluoroethyl)estra-4,9-dien-11-yl]-N-(pyridin-2-ylmethyl)benzamide | 601, 3.68 min. |
| 21 | 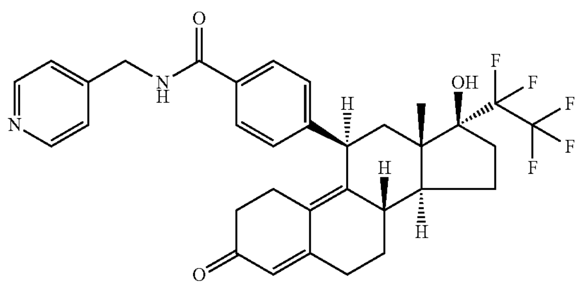 | 4-[(11β,17β)-17-hydroxy-3-oxo-17-(pentafluoroethyl)estra-4,9-dien-11-yl]-N-(pyridin-4-ylmethyl)benzamide | 601, 3.30 min. |
| 22 | 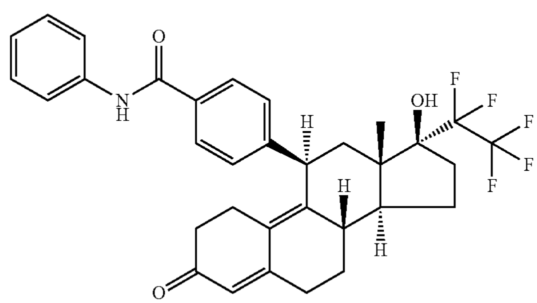 | 4-[(11β,17β)-17-hydroxy-3-oxo-17-(pentafluoroethyl)estra-4,9-dien-11-yl]-N-phenylbenzamide | 586, 4.57 min. |
| 23 | 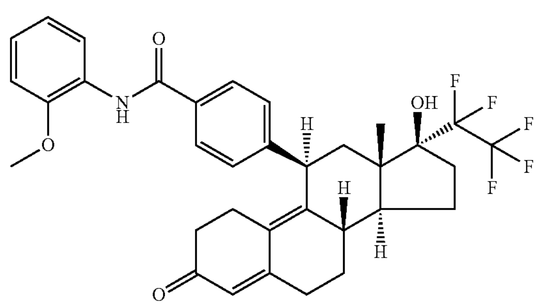 | 4-[(11β,17β)-17-hydroxy-3-oxo-17-(pentafluoroethyl)estra-4,9-dien-11-yl]-N-(2-methoxyphenyl)benzamide | 616, 4.70 min. |

-continued

| Ex. | Structure | Name | HPLC-MS (MH+, RT) |
|---|---|---|---|
| 24 | 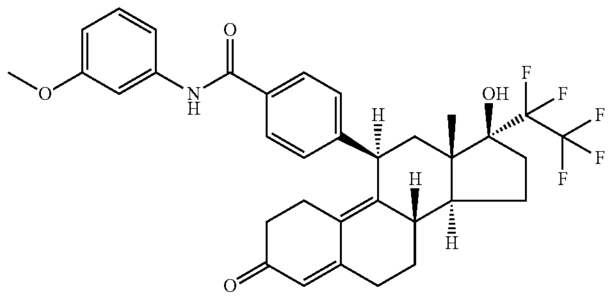 | 4-[(11β,17β)-17-hydroxy-3-oxo-17-(pentafluoroethyl)estra-4,9-dien-11-yl]-N-(3-methoxyphenyl)benzamide | 616, 4.58 min. |
| 25 | 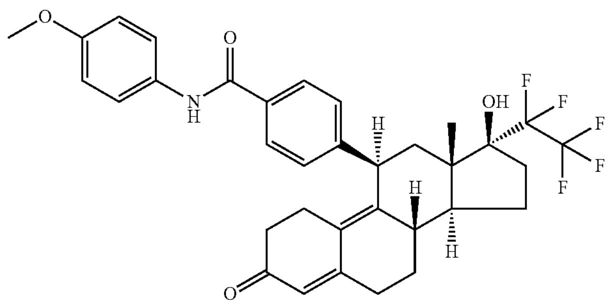 | 4-[(11β,17β)-17-hydroxy-3-oxo-17-(pentafluoroethyl)estra-4,9-dien-11-yl]-N-(4-methoxyphenyl)benzamide | 616, 4.53 min. |
| 26 | 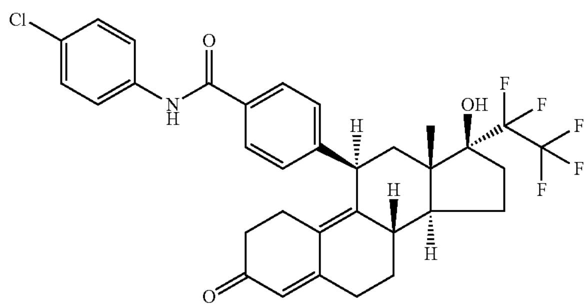 | N-(4-chlorophenyl)-4-[(11β,17β)-17-hydroxy-3-oxo-17-(pentafluoroethyl)estra-4,9-dien-11-yl]benzamide | 620, 4.78 min. |
| 27 | 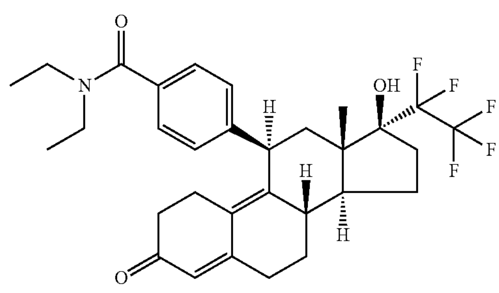 | N,N-diethyl-4-[(11β,17β)-17-hydroxy-3-oxo-17-(pentafluoroethyl)estra-4,9-dien-11-yl]benzamide | 566, 4.38 min. |
| 28 | 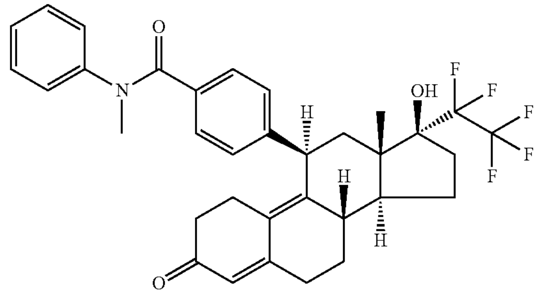 | 4-[(11β,17β)-17-hydroxy-3-oxo-17-(pentafluoroethyl)estra-4,9-dien-11-yl]-N-methyl-N-phenylbenzamide | 600, 4.62 min. |

| Ex. | Structure | Name | HPLC-MS (MH+, RT) |
|---|---|---|---|
| 29 | 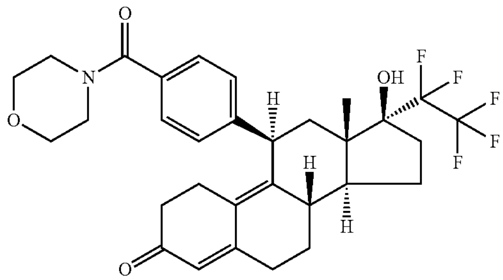 | (11β,17β)-17-hydroxy-11-[4-(morpholin-4-ylcarbonyl)phenyl]-17-(pentafluoroethyl)estra-4,9-dien-3-one | 580, 4.03 min. |
| 30 | 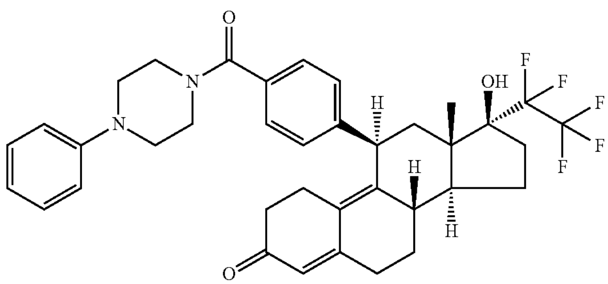 | (11β,17β)-17-hydroxy-17-(pentafluoroethyl)-11-{4-[(4-phenylpiperazin-1-yl)carbonyl]phenyl}estra-4,9-dien-3-one | 655, 4.71 min. |
| 31 | 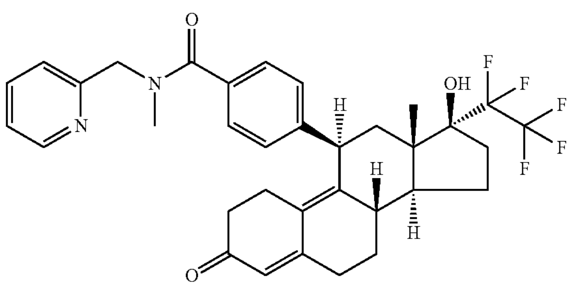 | 4-[(11β,17β)-17-hydroxy-3-oxo-17-(pentafluoroethyl)estra-4,9-dien-11-yl]-N-methyl-N-(pyridin-2-ylmethyl)benzamide | 615, 4.00 min. |
| 32 | 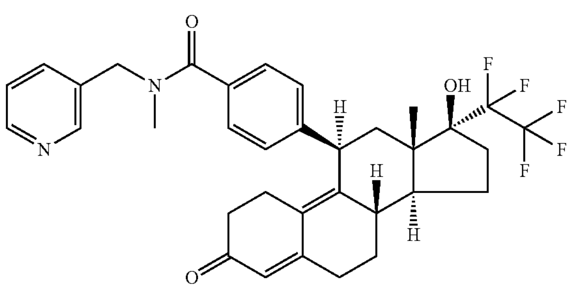 | 4-[(11β,17β)-17-hydroxy-3-oxo-17-(pentafluoroethyl)estra-4,9-dien-11-yl]-N-methyl-N-(pyridin-3-ylmethyl)benzamide | 615, 3.57 min. |
| 33 | 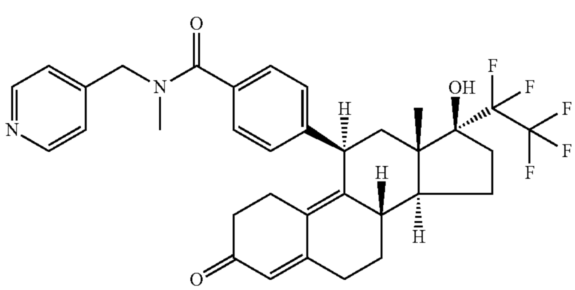 | 4-[(11β,17β)-17-hydroxy-3-oxo-17-(pentafluoroethyl)estra-4,9-dien-11-yl]-N-methyl-N-(pyridin-4-ylmethyl)benzamide | 615, 3.35 min. |

-continued

| Ex. | Structure | Name | HPLC-MS (MH+, RT) |
|---|---|---|---|
| 34 | 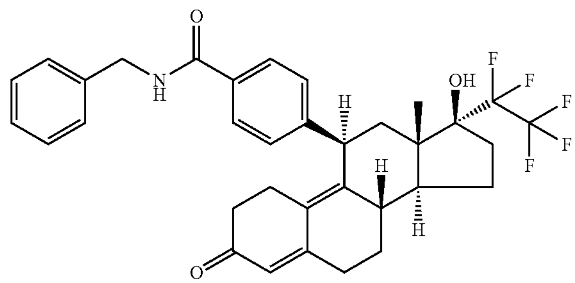 | N-benzyl-4-[(11β,17β)-17-hydroxy-3-oxo-17-(pentafluoroethyl)estra-4,9-dien-11-yl]benzamide | 600, 4.49 min. |
| 35 | 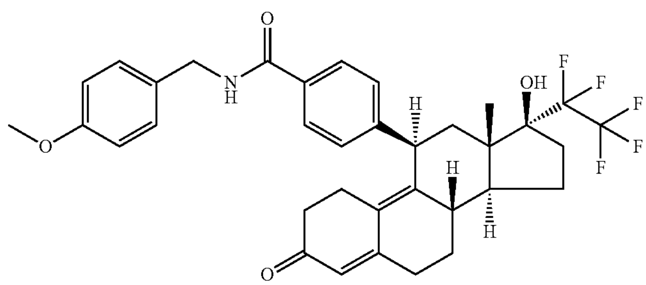 | 4-[(11β,17β)-17-hydroxy-3-oxo-17-(pentafluoroethyl)estra-4,9-dien-11-yl]-N-(4-methoxybenzyl)benzamide | 630, 4.45 min. |
| 36 | 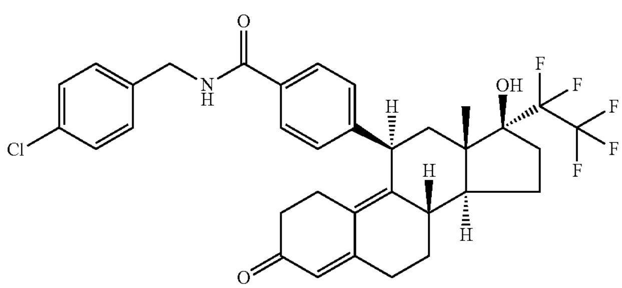 | N-(4-chlorobenzyl)-4-[(11β,17β)-17-hydroxy-3-oxo-17-(pentafluoroethyl)estra-4,9-dien-11-yl]benzamide | 634, 4.63 min. |
| 37 | 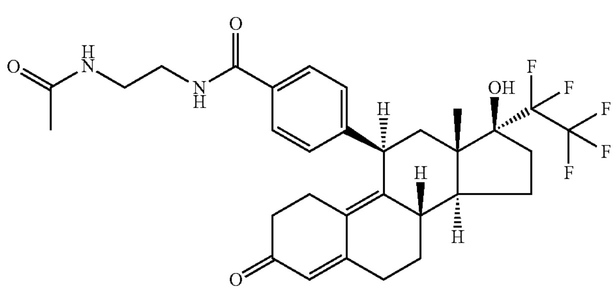 | N-(2-acetamidoethyl)-4-[(11β,17β)-17-hydroxy-3-oxo-17-(pentafluoroethyl)estra-4,9-dien-11-yl]benzamide | 595, 3.77 min. |
| 38 | 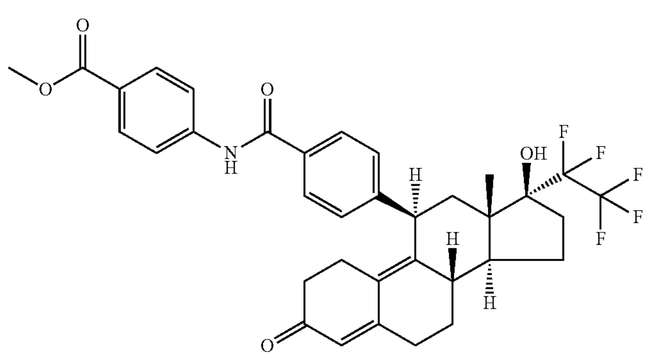 | methyl-4-({4-[(11β,17β)-17-hydroxy-3-oxo-17-(pentafluoroethyl)estra-4,9-dien-11-yl]benzoyl}amino)benzoate | 644, 4.58 min. |

| Ex. | Structure | Name | HPLC-MS (MH+, RT) |
|---|---|---|---|
| 39 | 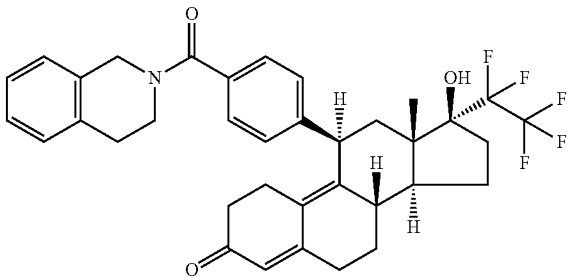 | (11β,17β)-11-[4-(3,4-dihydroisoquinolin-2(1H)-ylcarbonyl)phenyl]-17-hydroxy-17-(pentafluoroethyl)estra-4,9-dien-3-one | 626, 4.71 min. |
| 40 | 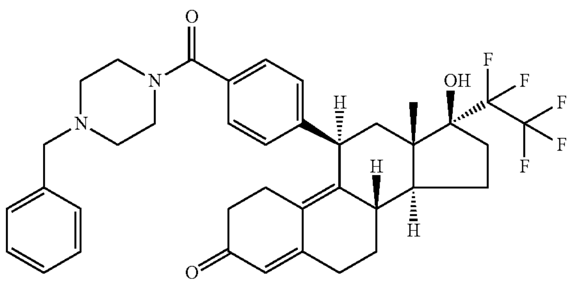 | (11β,17β)-11-{4-[(4-benzylpiperazin-1-yl)carbonyl]phenyl}-17-hydroxy-17-(pentafluoroethyl)estra-4,9-dien-3-one | 669, 3.38 min. |
| 41 | 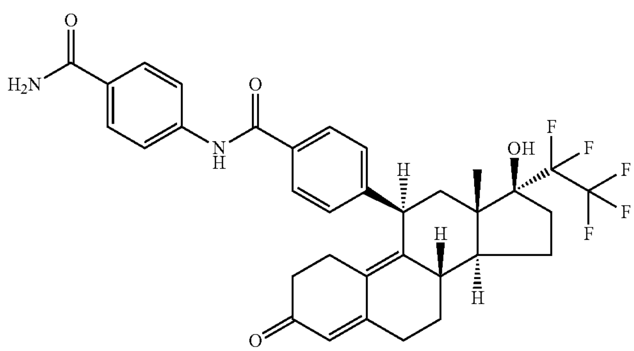 | N-(4-carbamoylphenyl)-4-[(11β,17β)-17-hydroxy-3-oxo-17-(pentafluoroethyl)estra-4,9-dien-11-yl]benzamide | 629, 4.05 min. |
| 42 | 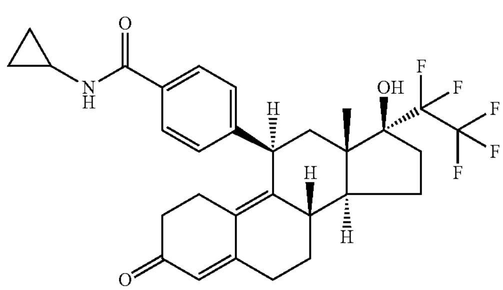 | N-cyclopropyl-4-[(11β,17β)-17-hydroxy-3-oxo-17-(pentafluoroethyl)estra-4,9-dien-11-yl]benzamide | 550, 4.13 min. |
| 43 | 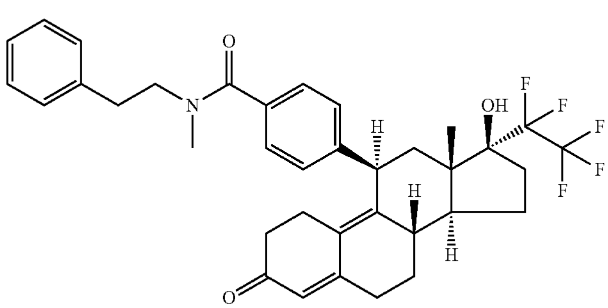 | 4-[(11β,17β)-17-hydroxy-3-oxo-17-(pentafluoroethyl)estra-4,9-dien-11-yl]-N-methyl-N-(2-phenylethyl)benzamide | 628, 4.70 min. |

-continued

| Ex. | Structure | Name | HPLC-MS (MH+, RT) |
|---|---|---|---|
| 44 | 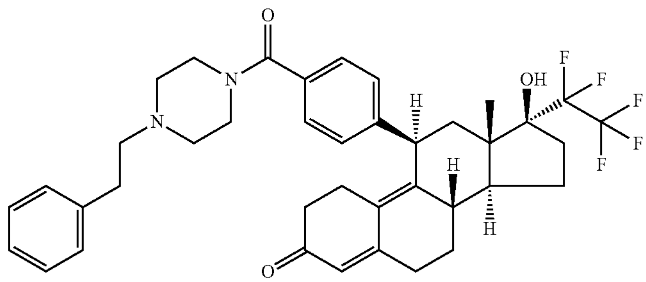 | (11β,17β)-17-hydroxy-17-(pentafluoroethyl)-11-(4-{[4-(2-phenylethyl)piperazin-1-yl]carbonyl}phenyl)estra-4,9-dien-3-one | 683, 3.40 min. |
| 45 | 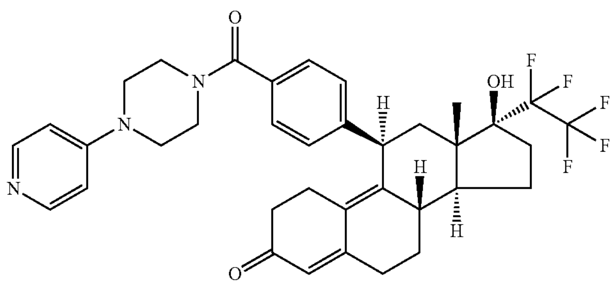 | (11β,17β)-17-hydroxy-17-(pentafluoroethyl)-11-(4-{[4-(pyridin-4-yl)piperazin-1-yl]carbonyl}phenyl)estra-4,9-dien-3-one | 656, 3.25 min. |
| 46 | 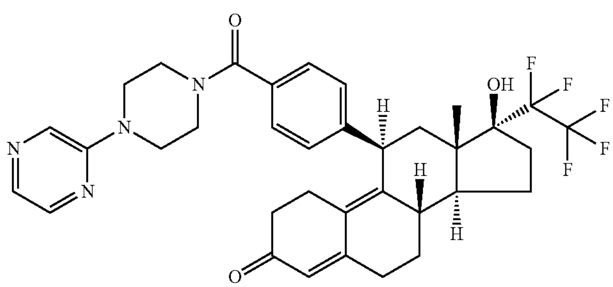 | (11β,17β)-17-hydroxy-17-(pentafluoroethyl)-11-(4-{[4-(pyrazin-2-yl)piperazin-1-yl]carbonyl}phenyl)estra-4,9-dien-3-one | 657, 4.12 min. |
| 47 | 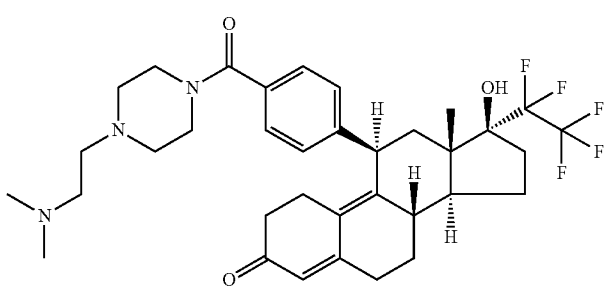 | (11β,17β)-11-[4-({4-[2-(dimethylamino)ethyl]piperazin-1-yl}carbonyl)phenyl]-17-hydroxy-17-(pentafluoroethyl)estra-4,9-dien-3-one | 650, 3.11 min. |
| 48 | 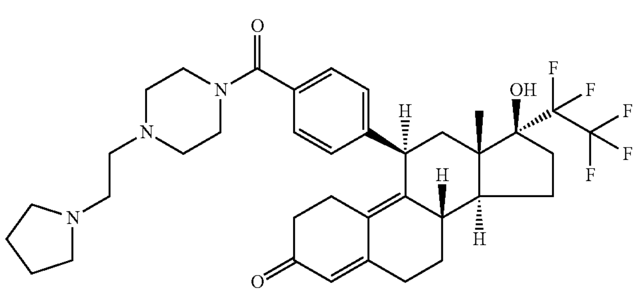 | (11β,17β)-17-hydroxy-17-(pentafluoroethyl)-11-[4-({4-[2-(pyrrolidin-1-yl)ethyl]piperazin-1-yl}carbonyl)phenyl]estra-4,9-dien-3-one | 676, 3.17 min. |

-continued

| Ex. | Structure | Name | HPLC-MS (MH+, RT) |
|---|---|---|---|
| 49 | 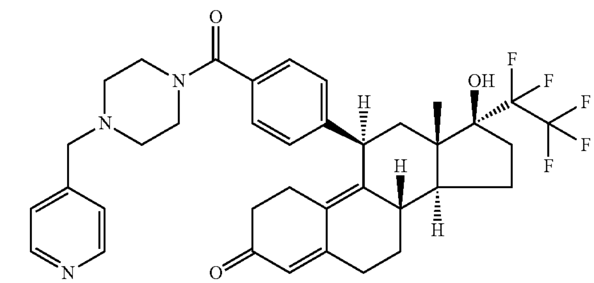 | (11β,17β)-17-hydroxy-17-(pentafluoroethyl)-11-(4-{[4-(pyridin-4-ylmethyl)piperazin-1-yl]carbonyl}phenyl)estra-4,9-dien-3-one | 670, 3.21 min. |
| 50 | 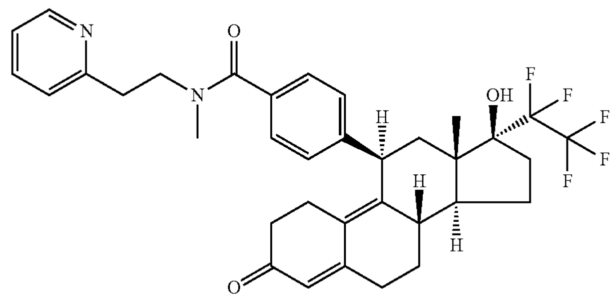 | 4-[(11β,17β)-17-hydroxy-3-oxo-17-(pentafluoroethyl)estra-4,9-dien-11-yl]-N-methyl-N-[2-(pyridin-2-yl)ethyl]benzamide | 629, 3.45 min. |
| 51 | 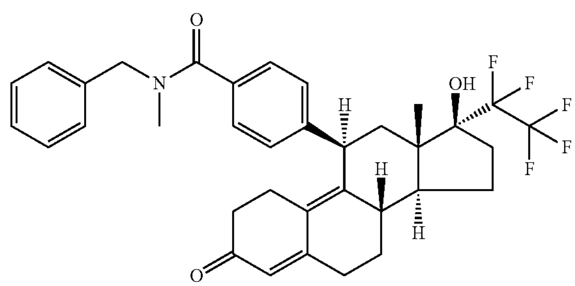 | N-benzyl-4-[(11β,17β)-17-hydroxy-3-oxo-17-(pentafluoroethyl)estra-4,9-dien-11-yl]-N-methylbenzamide | 614, 4.65 min. |
| 52 | 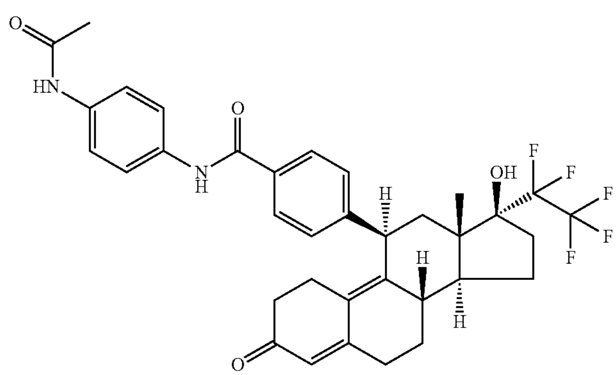 | N-(4-acetamidophenyl)-4-[(11β,17β)-17-hydroxy-3-oxo-17-(pentafluoroethyl)estra-4,9-dien-11-yl]benzamide | 643, 4.15 min. |
| 53 | 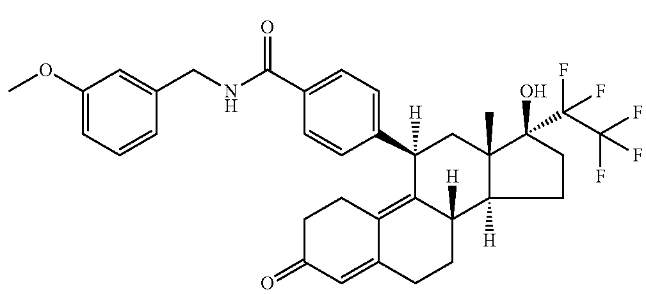 | 4-[(11β,17β)-17-hydroxy-3-oxo-17-(pentafluoroethyl)estra-4,9-dien-11-yl]-N-(3-methoxybenzyl)benzamide | 630, 4.47 min. |

-continued

| Ex. | Structure | Name | HPLC-MS (MH+, RT) |
|---|---|---|---|
| 54 | 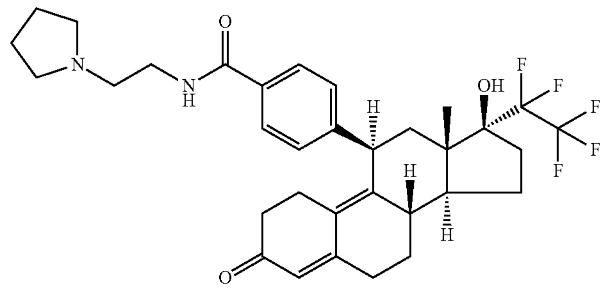 | 4-[(11β,17β)-17-hydroxy-3-oxo-17-(pentafluoroethyl)estra-4,9-dien-11-yl]-N-[2-(pyrrolidin-1-yl)ethyl]benzamide | 607, 4.75 min. |
| 55 | 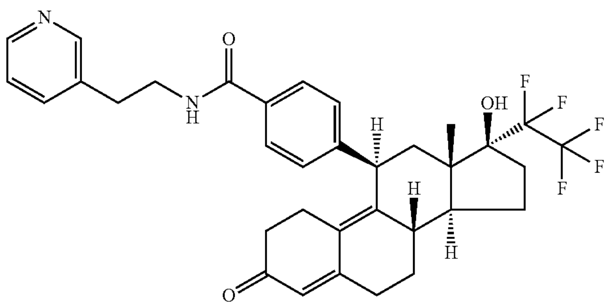 | 4-[(11β,17β)-17-hydroxy-3-oxo-17-(pentafluoroethyl)estra-4,9-dien-11-yl]-N-[2-(pyridin-3-yl)ethyl]benzamide | 615, 3.30 min. |
| 56 | 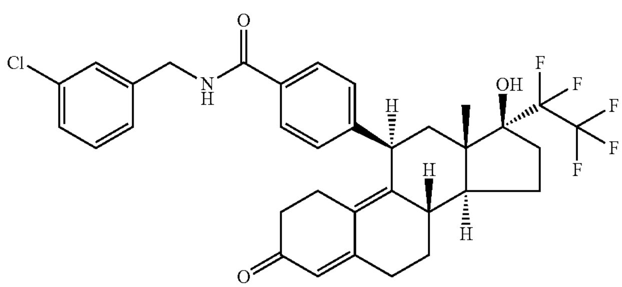 | N-(3-chlorobenzyl)-4-[(11β,17β)-17-hydroxy-3-oxo-17-(pentafluoroethyl)estra-4,9-dien-11-yl]benzamide | 634, 4.70 min. |
| 57 | 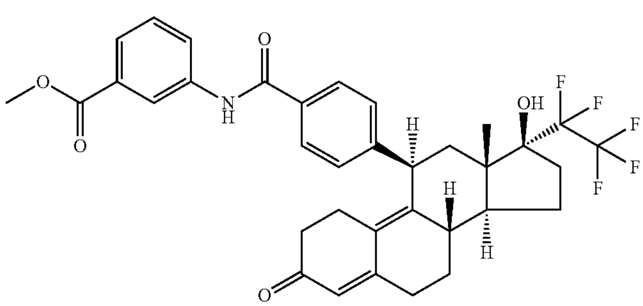 | methyl-3-({4-[(11β,17β)-17-hydroxy-3-oxo-17-(pentafluoroethyl)estra-4,9-dien-11-yl]benzoyl}amino)benzoate | 644, 4.60 min. |
| 58 | 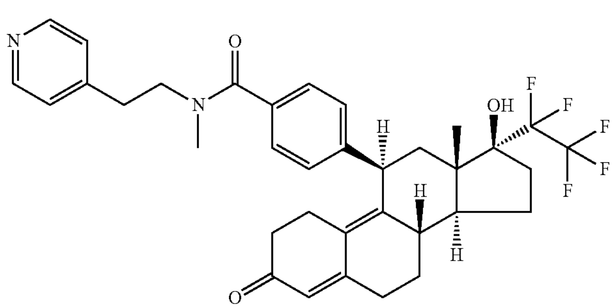 | 4-[(11β,17β)-17-hydroxy-3-oxo-17-(pentafluoroethyl)estra-4,9-dien-11-yl]-N-methyl-N-[2-(pyridin-4-yl)ethyl]benzamide | 629, 3.28 min. |

-continued

| Ex. | Structure | Name | HPLC-MS (MH+, RT) |
|---|---|---|---|
| 59 | 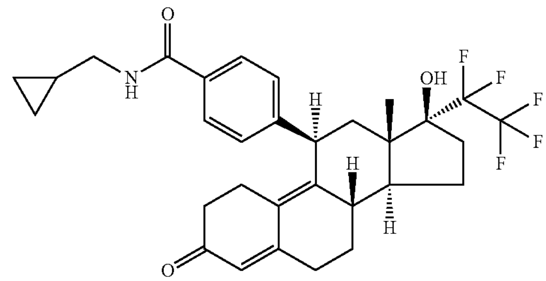 | N-(cyclopropylmethyl)-4-[(11β,17β)-17-hydroxy-3-oxo-17-(pentafluoroethyl)estra-4,9-dien-11-yl]benzamide | 564, 4.35 min. |
| 60 | 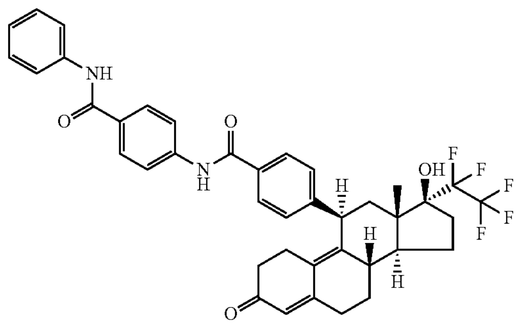 | 4-[(11β,17β)-17-hydroxy-3-oxo-17-(pentafluoroethyl)estra-4,9-dien-11-yl]-N-[4-(phenylcarbamoyl)phenyl]benzamide | 705, 4.50 min. |
| 61 | 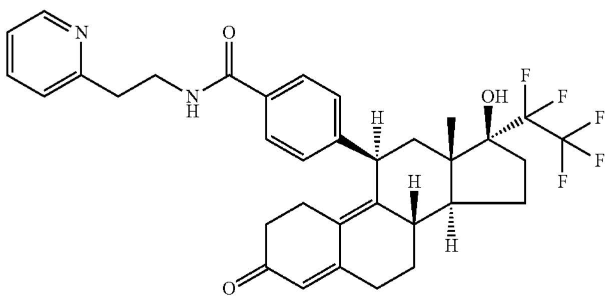 | 4-[(11β,17β)-17-hydroxy-3-oxo-17-(pentafluoroethyl)estra-4,9-dien-11-yl]-N-[2-(pyridin-2-yl)ethyl]benzamide | 615, 3.37 min. |
| 62 | 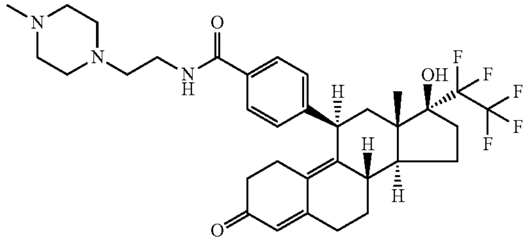 | 4-[(11β,17β)-17-hydroxy-3-oxo-17-(pentafluoroethyl)estra-4,9-dien-11-yl]-N-[2-(4-methylpiperazin-1-yl)ethyl]benzamide | 636, 3.08 min. |
| 63 | 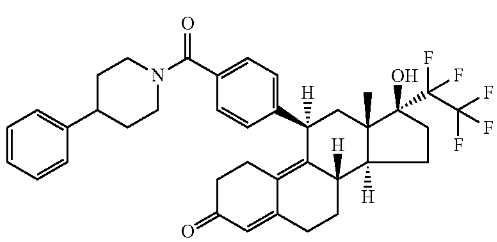 | (11β,17β)-17-hydroxy-17-(pentafluoroethyl)-11-{4-[(4-phenylpiperidin-1-yl)carbonyl]phenyl}estra-4,9-dien-3-one | 654, 4.87 min. |

-continued

| Ex. | Structure | Name | HPLC-MS (MH+, RT) |
|---|---|---|---|
| 64 | 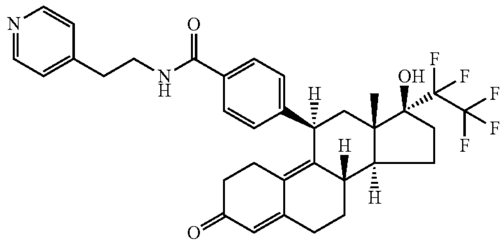 | 4-[(11β,17β)-17-hydroxy-3-oxo-17-(pentafluoroethyl)estra-4,9-dien-11-yl]-N-[2-(pyridin-4-yl)ethyl]benzamide | 615, 3.23 min. |
| 65 | 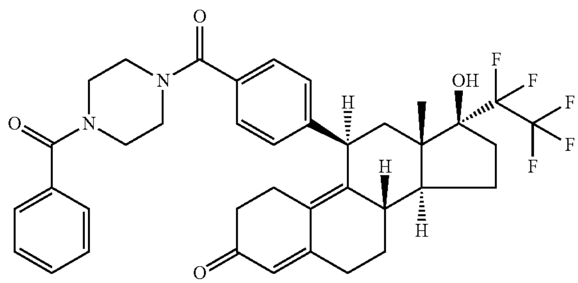 | (11β,17β)-11-{4-[(4-benzoylpiperazin-1-yl)carbonyl]phenyl}-17-hydroxy-17-(pentafluoroethyl)estra-4,9-dien-3-one | 683, 4.28 min. |
| 66 | 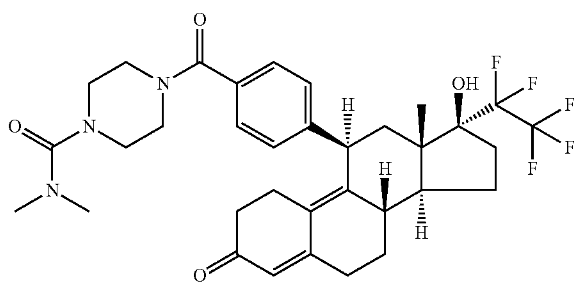 | 4-{4-[(11β,17β)-17-hydroxy-3-oxo-17-(pentafluoroethyl)estra-4,9-dien-11-yl]benzoyl}-N,N-dimethylpiperazine-1-carboxamide | 650, 3.93 min. |
| 67 | 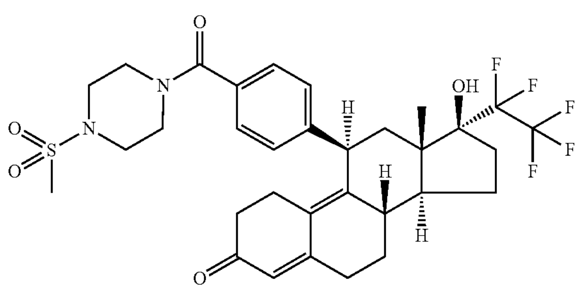 | (11β,17β)-17-hydroxy-11-(4-{[4-(methylsulphonyl)piperazin-1-yl]carbonyl}phenyl)-17-(pentafluoroethyl)estra-4,9-dien-3-one | 657, 4.10 min. |
| 68 | 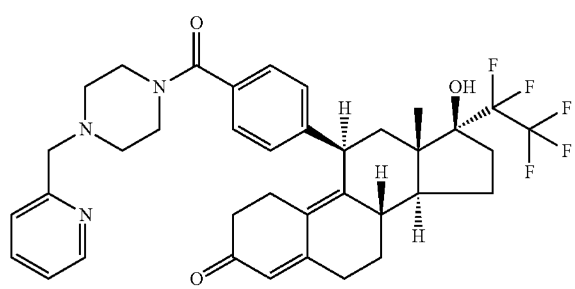 | (11β,17β)-17-hydroxy-17-(pentafluoroethyl)-11-(4-{[4-(pyridin-2-ylmethyl)piperazin-1-yl]carbonyl}phenyl)estra-4,9-dien-3-one | 670, 3.20 min. |

| Ex. | Structure | Name | HPLC-MS (MH+, RT) |
|---|---|---|---|
| 69 | 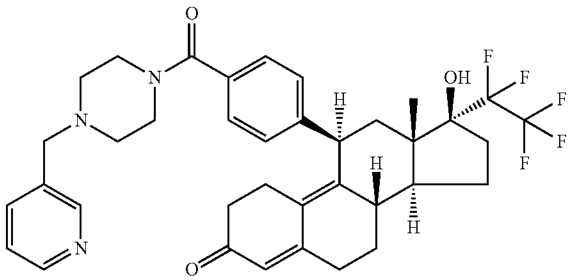 | (11β,17β)-17-hydroxy-17-(pentafluoroethyl)-11-(4-{[4-(pyridin-3-ylmethyl)piperazin-1-yl]carbonyl}phenyl)estra-4,9-dien-3-one | 670, 3.17 min. |
| 70 | 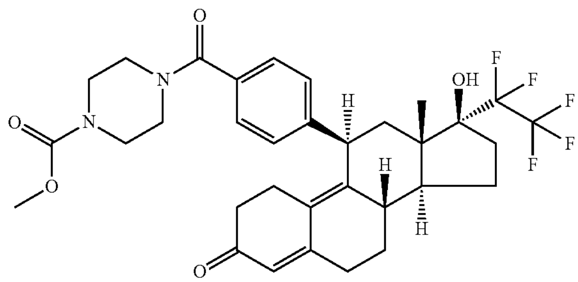 | methyl-4-{4-[(11β,17β)-17-hydroxy-3-oxo-17-(pentafluoroethyl)estra-4,9-dien-11-yl]benzoyl}piperazine-1-carboxylate | 637, 4.08 min. |
| 71 | 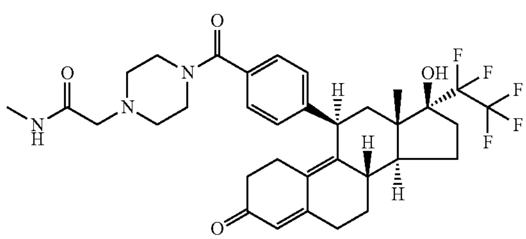 | 2-(4-{4-[(11β,17β)-17-hydroxy-3-oxo-17-(pentafluoroethyl)estra-4,9-dien-11-yl]benzoyl}piperazin-1-yl)-N-methyl acetamide | 650, 3.23 min. |
| 72 | 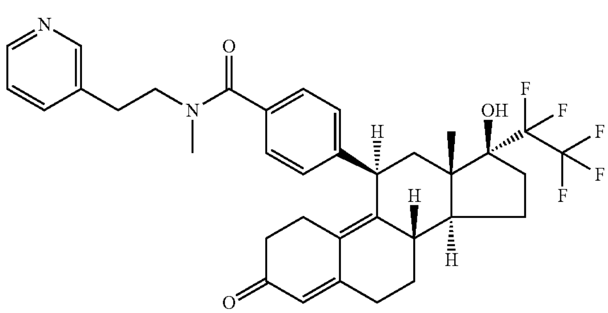 | 4-[(11β,17β)-17-hydroxy-3-oxo-17-(pentafluoroethyl)estra-4,9-dien-11-yl]-N-methyl-N-[2-(pyridin-3-yl)ethyl]benzamide | 629, 3.48 min. |

EXAMPLE 73

(11β,17β)-17-Hydroxy-17-(pentafluoroethyl)-11-[4-(piperazin-1-ylcarbonyl)phenyl]estra-4,9-dien-3-one

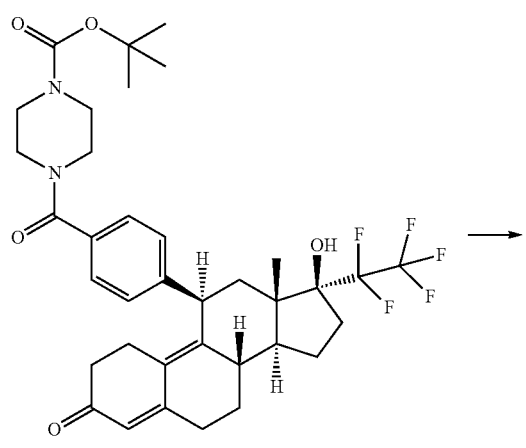

0.47 ml trifluoroacetic acid was added to a solution of 166 mg of the compound described in example 4) in 5 ml dichloromethane. It was stirred for 90 minutes at 23° C. and then the reaction mixture was poured into ice-cold saturated sodium hydrogen carbonate solution. Then it was extracted with dichloromethane several times. The combined organic phases were washed with saturated sodium chloride solution and dried over sodium sulphate. The raw product was purified by silica gel chromatography. 56 mg of the title compound was obtained.

$^1$H NMR (300 MHz, CDCl$_3$): δ=7.37 d (2H); 7.28 d (2H); 5.83 sbr (1H); 4.50 dbr (1H); 3.76 m (2H); 3.49 m (2H); 2.96 m (4H); 0.59 s (3H).

EXAMPLE 74

(11β,17β)-11-{4-[(4-Acetylpiperazin-1-yl)carbonyl]phenyl}-17-hydroxy-17-(pentafluoroethyl)estra-4,9-dien-3-one

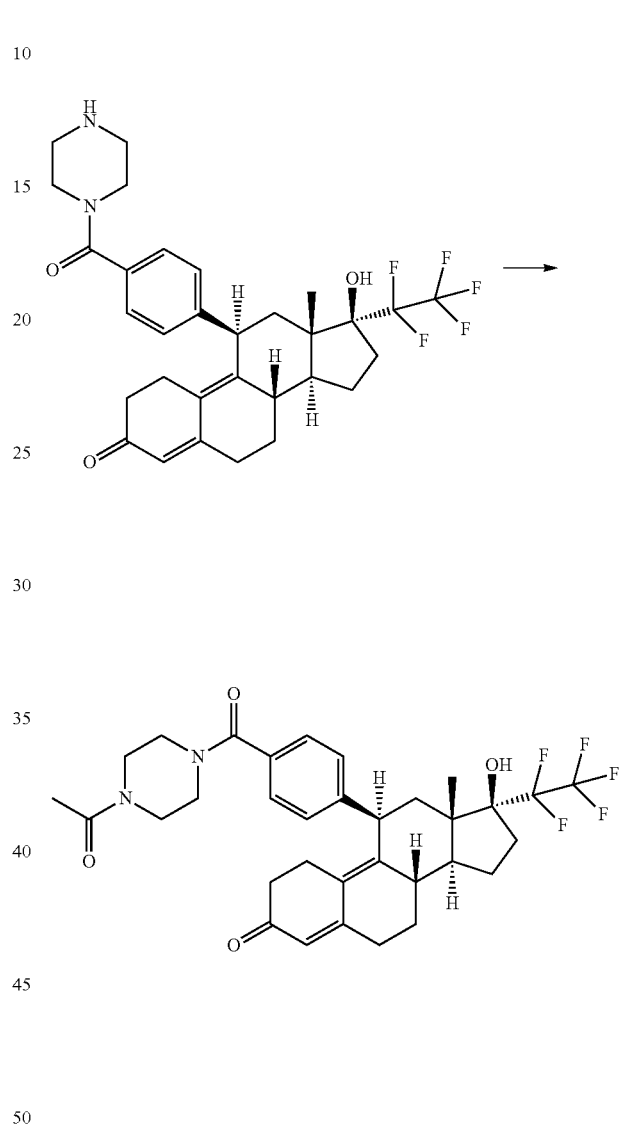

42 µl triethylamine and 14 µl acetic acid anhydride were added to a solution of 70 mg of the compound described in example 73) in 2.5 ml dichloromethane. It was stirred for 90 minutes at 23° C. and then the reaction mixture was poured into ice-cold saturated sodium hydrogen carbonate solution. Then it was extracted with dichloromethane several times. The combined organic phases were washed with saturated sodium chloride solution and dried over sodium sulphate. The raw product was purified by silica gel chromatography. 35 mg of the title compound was obtained.

$^1$H NMR (300 MHz, CDCl$_3$): δ=7.34 d (2H); 7.24 d (2H); 5.79 sbr (1H); 4.46 dbr (1H); 3.35-3.85 m (8H); 2.12 s (3H); 0.58 s (3H).

EXAMPLE 75

1-{4-[(11β,17β)-17-Hydroxy-3-oxo-17-(pentafluoro-ethyl)estra-4,9-dien-11-yl]benzoyl}piperidine-4-carboxylic acid

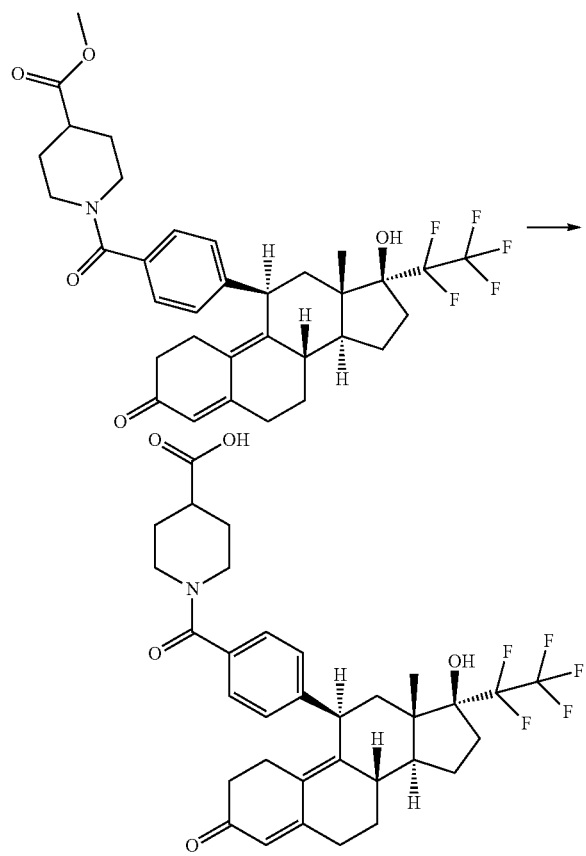

0.53 ml of a 2 N sodium hydroxide solution was added to a solution of 225 mg of the compound described in example 6) in 5 ml methanol. It was stirred for 2.5 hours at 23° C. and then the reaction mixture was poured into 60 ml of ice water. Then it was acidified with 2.5 ml of 2N hydrochloric acid and stirred for a further 16 hours. The resultant precipitate was filtered off with suction and was washed with water. The raw product was purified by silica gel chromatography. 139 mg of the title compound was obtained.

$^1$H NMR (400 MHz, CDCl$_3$): δ=7.28 d (2H); 7.20 d (2H); 5.76 sbr (1H); 4.43 dbr (1H); 0.51 s (3H).

EXAMPLE 76

2-({4-[(11β,17β)-17-Hydroxy-3-oxo-17-(pentafluo-roethyl)estra-4,9-dien-11-yl]benzoyl}amino)benzoic acid

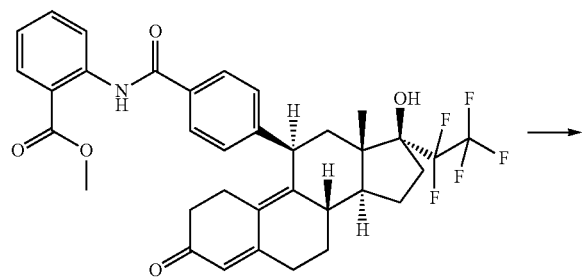

-continued

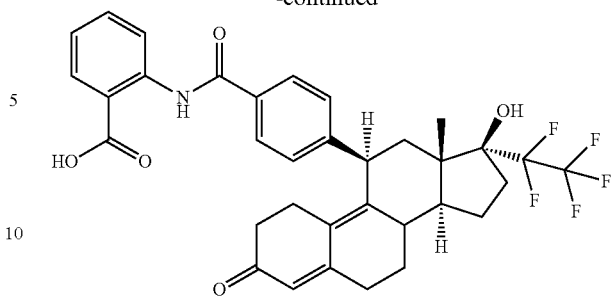

A solution of 16 mg lithium hydroxide in 466 μl water was added to a solution of 43 mg of the compound described in example 10) in 2 ml tetrahydrofuran. It was stirred for 19 hours at 23° C. Then the reaction mixture was diluted with 1 ml water and then acidified with 0.4 ml of 2N hydrochloric acid. It was extracted with ethyl acetate several times. The combined organic phases were washed with saturated sodium chloride solution and dried over sodium sulphate. The raw product was purified by silica gel chromatography. 14 mg of the title compound was obtained.

$^1$H NMR (400 MHz, CDCl$_3$): δ=8.93 d (1H); 8.13 d (1H); 7.92 d (2H); 7.65 tbr (1H); 7.27 d (2H); 7.15 tbr (1H); 5.87 sbr (1H); 4.45 dbr (1H); 0.50 s (3H).

EXAMPLE 77

3-({4-[(11β,17β)-17-Hydroxy-3-oxo-17-(pentafluo-roethyl)estra-4,9-dien-11-yl]benzoyl}amino)benzoic acid

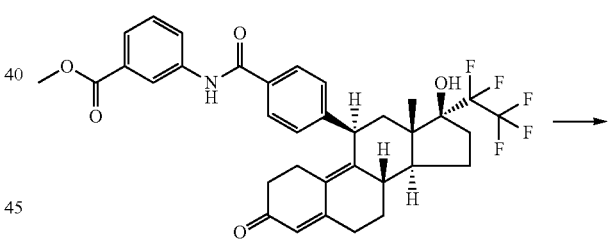

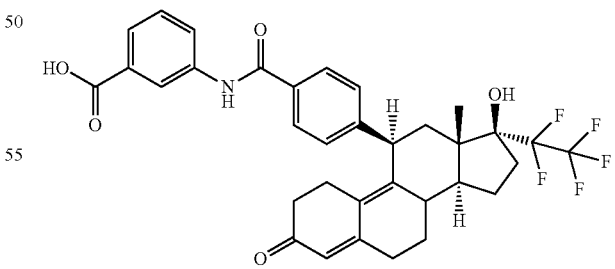

Similarly to example 76, 46 mg of the title compound was obtained from 115 mg of the compound described in example 57 by reaction with lithium hydroxide in a mixture of tetrahydrofuran and water.

¹H NMR (300 MHz, CDCl₃): δ=8.19 m (2H); 7.78-7.90 m (3H); 7.47 tbr (1H); 7.28 m (2H); 5.79 sbr (1H); 4.48 dbr (1H); 0.57 s (3H).

EXAMPLE 78

4-({4-[(11β,17β)-17-Hydroxy-3-oxo-17-(pentafluoroethyl)estra-4,9-dien-11-yl]benzoyl}amino)benzoic acid

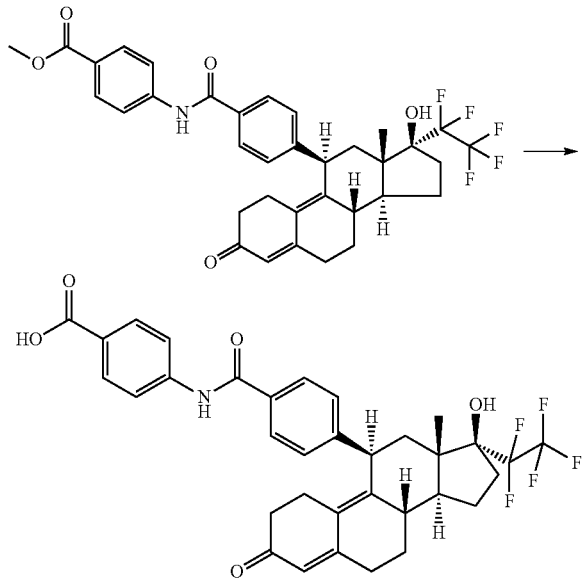

Similarly to example 76, 42 mg of the title compound was obtained from 92 mg of the compound described in example 38 by reaction with lithium hydroxide in a mixture of tetrahydrofuran and water.

¹H NMR (400 MHz, CDCl₃): δ=8.25 s (1H); 8.06 d (2H); 7.80 d (2H); 7.71 d (2H); 7.30 d (2H); 5.79 sbr (1H); 4.50 dbr (1H); 0.57 s (3H).

EXAMPLE 79

4'-[(11β,17β)-17-Hydroxy-3-oxo-17-(pentafluoroethyl)estra-4,9-dien-11-yl]biphenyl-4-carboxamide

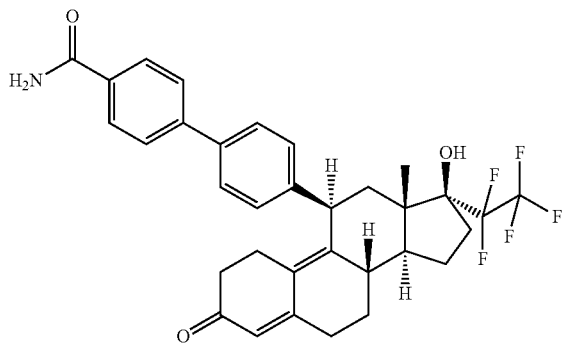

a) (5R,8S,11R,13S,14S,17S)-11-[4-(benzyloxy)phenyl]-5',5',13-trimethyl-17-(pentafluoroethyl)-1,2,6,7,8,11,12,13,14,15,16,17-dodecahydrospiro[cyclopenta[a]phenanthrene-3,2'-[1,3]dioxane]-5,17(4H)-diol

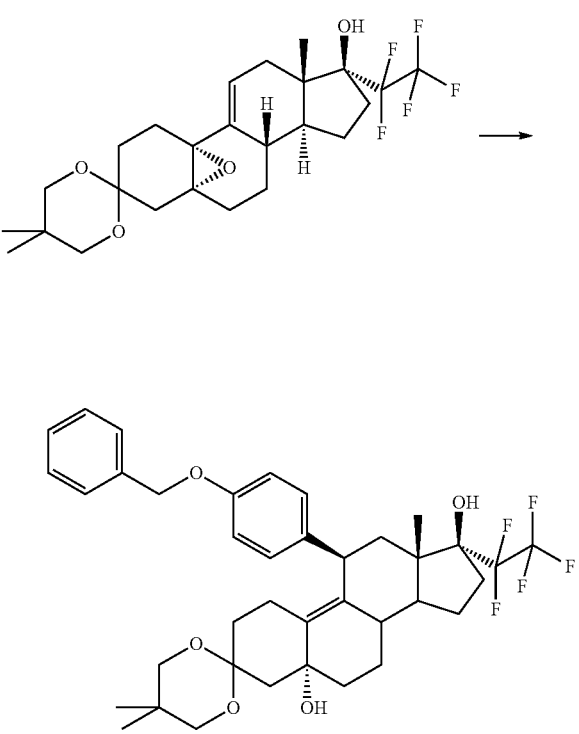

2.47 g of magnesium chips were suspended in 5 ml tetrahydrofuran and 50 μl dibromoethane was added, with stirring. A solution of 26.7 g of 1-bromo-4-(phenylmethoxy)benzene in 115 ml tetrahydrofuran was slowly added at 65° C. to the suspension. The resultant solution was cooled to 0° C. 301 mg of copper(I) chloride was added. It was stirred for a further 10 minutes at 0° C. and a solution of 10 g of the substance described in example 1a) in 70 ml tetrahydrofuran was then added slowly. The reaction mixture was allowed to reach 23° C. with stirring for approx. 3 hours and then it was stirred at this temperature for a further 10 hours. Then saturated aqueous ammonium chloride solution was added to the reaction mixture, with external cooling. It was stirred for a further 30 minutes and was then extracted several times with ethyl acetate. The combined organic phases were washed with saturated sodium chloride solution and dried over sodium sulphate. The raw product was purified by silica gel chromatography followed by crystallization from a mixture of dichloromethane and diisopropyl ether. 9.7 g of the title compound was obtained.

¹H NMR (400 MHz, CDCl₃): δ=7.30-7.50 m (5H); 7.12 d (2H); 6.88 d (2H); 5.02 s (2H); 4.43 s (1H); 4.28 dbr (1H); 3.50-3.60 m (3H); 3.42 d (1H); 1.06 s (3H); 0.87 s (3H); 0.56 s (3H).

b) (5R,8S,11R,13S,14S,17S)-11-[4-(benzyloxy)phenyl]-5',5',13-trimethyl-17-(pentafluoroethyl)-1,2,6,7,8,11,12,13,14,15,16,17-dodecahydrospiro[cyclopenta[a]phenanthrene-3,2'-[1,3]dioxane]-5,17(4H)-diol

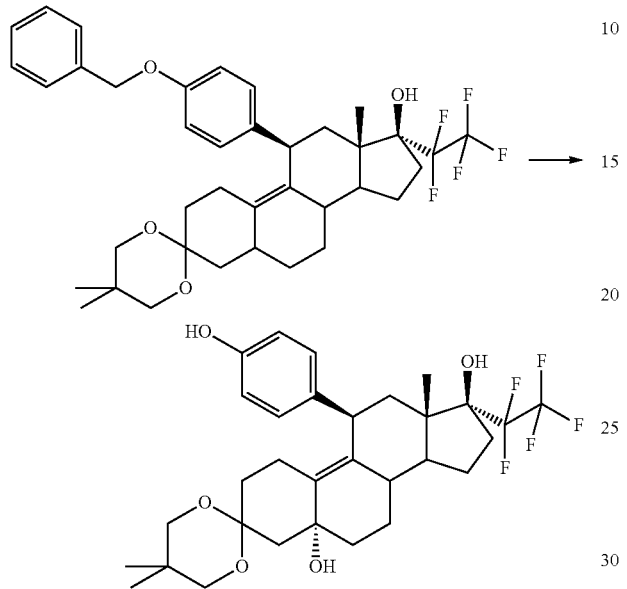

5.53 g ammonium formate and 972 mg palladium on activated charcoal (10%) were added to a solution of 9.72 g of the compound described in 79a) in 100 ml methanol. It was stirred for a further 2 hours at 23° C. and then filtered on Celite®. The filtrate was concentrated under vacuum. 8.5 g of raw product was obtained and, without purification, was used in the next step.

$^1$H NMR (300 MHz, CDCl$_3$): δ=7.05 d (2H); 6.70 d (2H); 4.43 sbr (1H); 4.27 dbr (1H); 3.50-3.58 m (3H); 3.41 sbr (1H); 1.94 s (3H); 0.86 s (3H); 0.54 s (3H).

c) 4-[(5R,8S,11R,13S,14S,17S)-5,17-dihydroxy-5',5',13-trimethyl-17-(pentafluoroethyl)-1,2,4,5,6,7,8,11,12,13,14,15,16,17-tetradecahydrospiro[cyclopenta[a]phenanthrene-3,2'-[1,3]dioxan]-11-yl]phenyl-1,1,2,2,3,3,4,4,4-nonafluorobutane-1-sulphonate

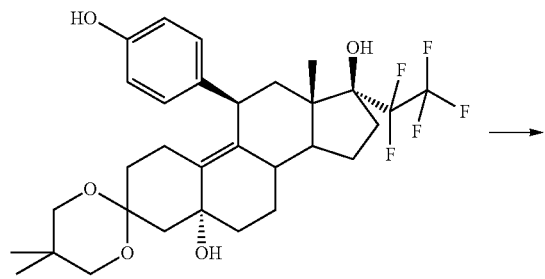

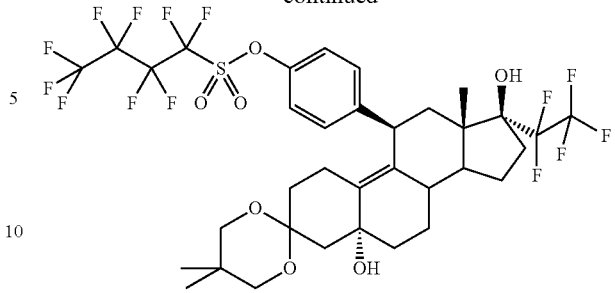

At 0° C., 14.64 ml of a 1.6-molar solution of n-butyllithium in hexane was added to a solution of 9.16 g of the compound described in 79b) in 100 ml absolute tetrahydrofuran. It was stirred for 30 minutes at 0° C. and then 5.62 ml of perfluorobutane-1-sulphonic acid fluoride was added slowly. Then it was stirred for a further 1.5 hours at 0° C. Then the reaction mixture was poured into a mixture of 300 ml of saturated sodium hydrogen carbonate solution and 90 ml of 2 N sodium hydroxide solution. It was stirred for 45 minutes and was then extracted with ethyl acetate several times. The combined organic phases were washed with saturated sodium chloride solution and dried over sodium sulphate. The raw product obtained was purified by silica gel chromatography. 10.1 g of the title compound was obtained.

$^1$H NMR (400 MHz, CDCl$_3$): δ=7.28 d (2H); 7.18 d (2H); 4.42 s (1H); 4.34 dbr (1H); 3.50-3.58 m (3H); 3.42 d (1H); 1.05 s (3H); 0.86 s (3H); 0.50 s (3H).

d) methyl-4'-[(5R,8S,13S,14S,17S)-5,17-dihydroxy-5,5,13-trimethyl-17-(pentafluoroethyl)-1,2,4,5,6,7,8,11,12,13,14,15,16,17-tetradecahydrospiro[cyclopenta[a]phenanthrene-3,2'-[1,3]dioxan]-11-yl]biphenyl-4-carboxylate

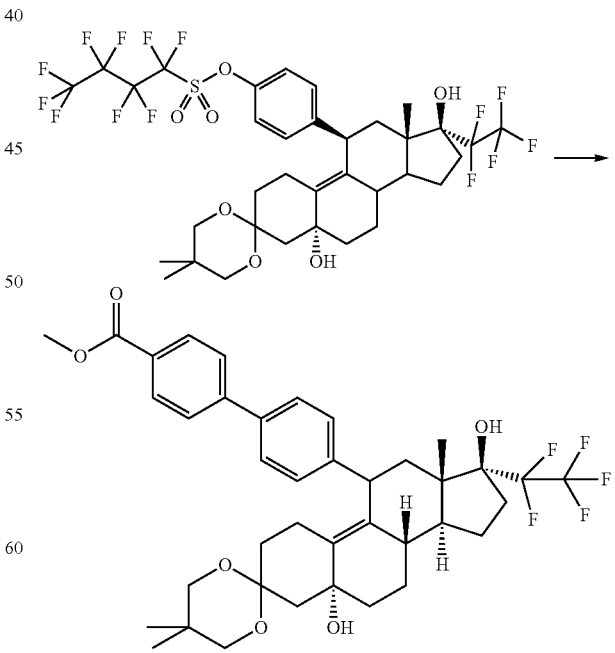

16.7 ml of 2 N aqueous sodium carbonate solution, 1.09 g of lithium chloride, 2.12 g of 4-methoxycarbonylphenyl-boronic acid and 1.6 g of tetrakis(triphenylphosphine)palladium (0) were added to a solution of 10 g of the compound described in 79c) in a mixture of 100 ml toluene and 50 ml ethanol. It was boiled for 2 hours under reflux, then it was allowed to cool to room temperature, and water and ethyl acetate were added to the reaction mixture. Next, the phases were separated and the aqueous phase was extracted with ethyl acetate. The combined organic phases were washed with saturated sodium chloride solution and dried over sodium sulphate. The raw product obtained was purified by silica gel chromatography followed by precipitation in diisopropyl ether. 5.8 g of the title compound was obtained.

$^1$H NMR (300 MHz, CDCl$_3$): δ=8.08 d (2H); 7.66 d (2H); 7.53 d (2H); 7.30 d (2H); 4.45 s (1H); 4.38 dbr (1H); 3.95 s (3H); 3.40-3.60 m (4H); 1.04 s (3H); 0.85 s (3H); 0.57 s (3H).

e) 4'-[(5R,8S,13S,14S,17S)-5,17-dihydroxy-5',5',13-trimethyl-17-(pentafluoroethyl)-1,2,4,5,6,7,8,11,12,13,14,15,16,17-tetradecahydrospiro[cyclopenta[a]phenanthrene-3,2'-[1,3]dioxan]-11-yl]biphenyl-4-carboxamide

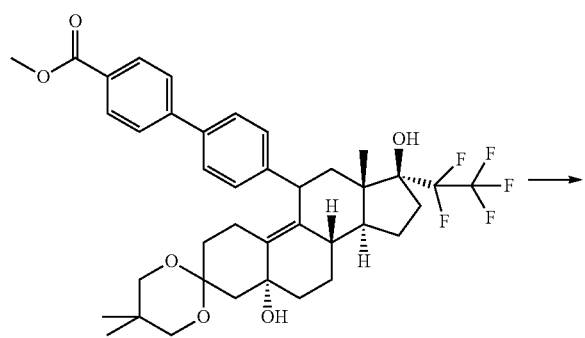

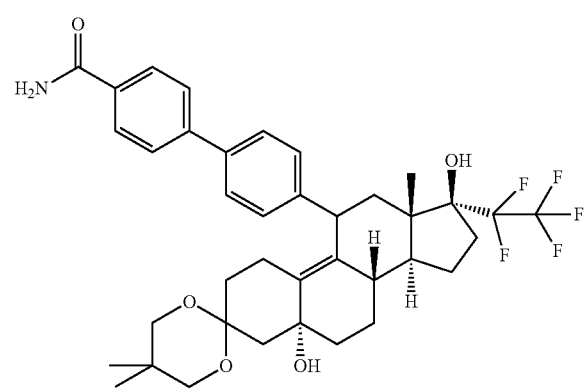

Similarly to example 1 g), 395 mg of the title compound was obtained from 755 mg of the compound described in 79e) by reaction with 11 ml of a 7-molar methanolic ammonia solution in a bomb tube at 85° C. for 4 days.

$^1$H NMR (400 MHz, CDCl$_3$): δ=7.87 d (2H); 7.64 d (2H); 7.50 d (2H); 7.31 d (2H); 6.12 sbr (1H); 5.68 sbr (1H); 4.45 s (1H); 4.39 dbr (1H); 3.40-3.60 m (4H); 1.07 s (3H); 0.87 s (3H); 0.58 s (3H).

f) 4'-[(11β,17β)-17-hydroxy-3-oxo-17-(pentafluoroethyl)estra-4,9-dien-11-yl]biphenyl-4-carboxamide

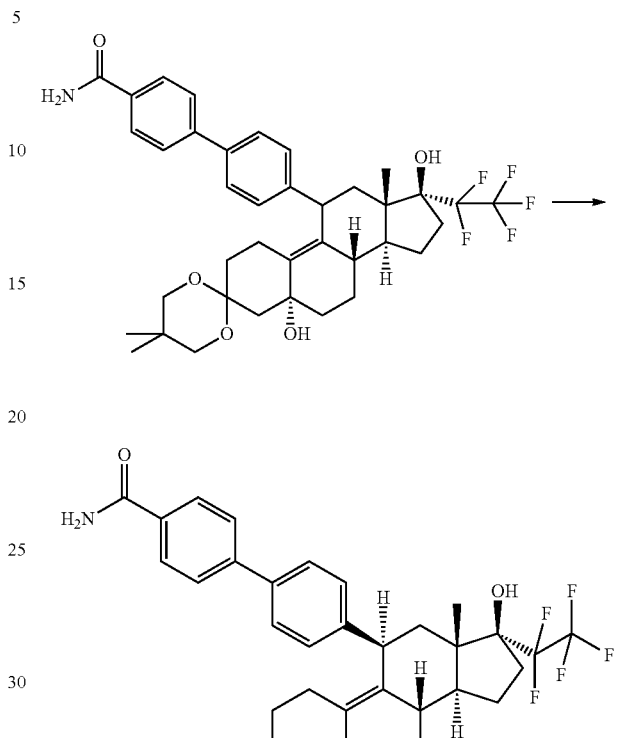

Similarly to example 2b), 301 mg of the title compound was obtained from 390 mg of the compound described in 79e) with 9 ml of 70% acetic acid at 35° C. for 16 hours.

$^1$H NMR (300 MHz, CDCl$_3$): δ=7.88 d (2H); 7.64 d (2H); 7.52 d (2H); 7.30 d (2H); 6.17 sbr (1H); 6.01 sbr (1H); 5.80 sbr (1H); 4.50 dbr (1H); 0.67 s (3H).

Progesterone-Receptor-Antagonistic Action in Stable Transfectants of Human Neuroblastoma Cells (SK-N-MC Cells) with the Human Progesterone A or Progesterone B Receptor and an MTV-LUC Reporter Construct SK-N-MC cells (human neuroblastoma cells) that have been stably transfected with plasmids that express the human progesterone receptor B (pRChPR-B-neo) or the human progesterone receptor A (pRChPR-A-neo) and a reporter construct (pMMTV-LUC), were incubated for 24 hours either in the absence (negative control) or in the presence of increasing amounts of the particular test compound (0.01 nmol/l, 0.1 nmol/l, 1 nmol/l, 10 nmol/l, 100 nmol/l and 1 μmol/l), to determine the agonistic efficacy. As positive control of reporter gene induction, the cells were treated with the synthetic gestagen promegestone (0.01 nmol/l, 0.1 nmol/l, 1 nmol/l, 10 nmol/l, 100 nmol/l and 1 μmol/l). For determination of the antagonistic activity, the cells were treated with 0.1 nmol/l promegestone and additionally with increasing amounts of the particular test compound (0.01 nmol/l, 0.1 nmol/l, 1 nmol/l, 10 nmol/l, 100 nmol/l and 1 μmol/l). The activity of the reporter gene LUC (LUC=luciferase) was determined in the cell lysates and was measured as RLU (relative light units). All measured values are given as % efficacy and as EC$_{50}$ or IC$_{50}$ concentrations.

a) agonistic activity:

None of the stated test compounds displays agonistic activity.

b) antagonistic activity:

All the stated compounds display 100% antagonistic efficacy.

The antagonistic potency of the compounds is presented in Table 1.

TABLE 1

Antagonistic potency of the compounds

| Ex. | PR-A IC$_{50}$ [nM] | PR-B IC$_{50}$ [nM] |
|---|---|---|
| 1 | 0.9 | 0.9 |
| 2 | 2.3 | 1.2 |
| 3 | 24 | 44 |
| 4 | 0.62 | 1.6 |
| 5 | 4.7 | 5 |
| 6 | 9.1 | 11 |
| 7 | 54 | 30 |
| 8 | 47 | 33 |
| 9 | 23 | 18 |
| 10 | 0.7 | 1.0 |
| 11 | 10 | n.d. |
| 12 | 1.32 | n.d. |
| 13 | 24 | n.d. |
| 14 | 0.42 | n.d. |
| 15 | 38 | n.d. |
| 16 | 0.67 | n.d. |
| 17 | 0.21 | n.d. |
| 18 | 4.7 | n.d. |
| 19 | 1.4 | n.d. |
| 20 | 3.8 | n.d. |
| 21 | 51 | n.d. |
| 22 | 39 | n.d. |
| 23 | 86 | n.d. |
| 24 | 3.7 | n.d. |
| 25 | 11.4 | n.d. |
| 26 | 28 | n.d. |
| 27 | 133 | n.d. |
| 28 | 63 | n.d. |
| 29 | 39 | n.d. |
| 30 | 7.2 | n.d. |
| 31 | 10.8 | n.d. |
| 32 | 375 | n.d. |
| 33 | 6.98 | n.d. |
| 34 | 14.4 | n.d. |
| 35 | 34 | n.d. |
| 36 | 20 | n.d. |
| 37 | 385 | n.d. |
| 38 | 1.88 | n.d. |
| 39 | 9.5 | n.d. |
| 40 | 117 | n.d. |
| 41 | 4.7 | n.d. |
| 42 | 7.3 | n.d. |
| 43 | 10.8 | n.d. |
| 44 | 25 | n.d. |
| 45 | 26 | n.d. |
| 46 | 4.3 | n.d. |
| 47 | 346 | n.d. |
| 48 | 667 | n.d. |
| 49 | 7.6 | n.d. |
| 50 | 15.7 | n.d. |
| 51 | 9.0 | n.d. |
| 52 | 0.71 | n.d. |
| 53 | 29 | n.d. |
| 54 | 21 | n.d. |
| 55 | 2.5 | n.d. |
| 56 | 2.3 | n.d. |
| 57 | 0.8 | n.d. |
| 58 | 5.7 | n.d. |
| 59 | 6.9 | n.d. |
| 60 | 0.39 | n.d. |
| 61 | 1.6 | n.d. |
| 62 | 94 | n.d. |
| 63 | 4.1 | n.d. |
| 64 | 1.1 | n.d. |
| 65 | 2.7 | n.d. |
| 66 | 35 | n.d. |
| 67 | 6.3 | n.d. |
| 68 | 16 | n.d. |
| 69 | 7.3 | n.d. |
| 70 | 1.7 | n.d. |
| 71 | 38 | n.d. |
| 72 | 1.4 | n.d. |
| 73 | 47 | 120 |
| 74 | 6.7 | 12.0 |
| 75 | 23 | 10 |
| 76 | 0.5 | n.d. |
| 77 | 140 | n.d. |
| 78 | 9.6 | n.d. |
| 79 | 0.01 | 0.07 | n.d.: not determined

Test as Abortifacient in Female Rats

The antagonistic action of the compounds according to the invention was tested on pregnant rats (6 rats per group) on day 5 to 7 post coitum in conventional conditions of husbandry and feeding.

After successful mating, the pregnant animals (presence of sperm in the vaginal smear on day 1 of pregnancy=d1 p.c.) were randomized and were divided into the treatment group and the control group. The animals then received, subcutaneously or orally, in each case 0.15; 0.5; 1.5 or 5 mg/kg of the test compound or 1.0 ml/kg of vehicle (benzyl benzoate/castor oil: 1+4 [v/v]) daily from day 5 to day 7 (d5-d7 p.c.).

Autopsy was carried out on day 9 (d9 p.c.). For characterization of progesterone-receptor-antagonistic action, the uterus was investigated for the presence of nidation sites. Complete absence, but also the presence of pathological, haemorrhagic or otherwise abnormal nidation sites on day 9 (d9 p.c.) was assessed as abortion. The results of the tests are shown in Table 3. The test compound displays a full effect at all doses.

TABLE 2

Results in the rat (termination of early pregnancy)

| Test compound according to | Daily dose [mg/kg] p.o. | Abortion rate [%] |
|---|---|---|
| Vehicle | | 0 |
| Example 1 | 0.5 | 0 |
| 4-[(11β,17β)-17-hydroxy-3-oxo-17-(pentafluoro-ethyl)estra-4,9-dien-11-yl]benzamide | 1.5 | 50 |
| | 5.0 | 100 |
| Example 79 | 0.5 | 100 |
| 4'-[(11β,17β)-17-hydroxy-3-oxo-17-(pentafluoro-ethyl)estra-4,9-dien-11-yl]biphenyl-4-carboxamide | 1.5 | 100 |
| | 5.0 | 100 |

Metabolic stability of 4-[(11β,17β)-17-hydroxy-3-oxo-17-(pentafluoro-ethyl)estra-4,9-dien-11-yl]benzamide and 4'-[(11β,17β)-17-hydroxy-3-oxo-17-(pentafluoro-ethyl)estra-4,9-dien-11-yl]biphenyl-4-carboxamide in human liver microsomes (HLM)

Isolated human liver microsomes (HLM) were used for assessing the metabolic stability of compounds of general formula I.

The incubations were carried out with 2.4 ml HLM solution (0.5 mg/ml protein content), 30 μl of the test compound (final concentration 1 μM) and 0.6 ml of the cofactor mixture (=NADPH-generating system of 3 IU glucose-6-phosphate dehydrogenase, 14.6 mg glucose-6-phosphate, 1.2 mg NADP) at 37° C. in 100 mM phosphate buffer at pH 7.4. Samples are taken at 6 time points (2-60 min), precipitated with an equal volume of methanol, and the recovery of the test substances used in the supernatant is determined by LC-MS/MS analysis. The intrinsic clearance of the substance in the liver microsome assay can be calculated from the value found for the half-life of substance breakdown. Using this, on the basis of various physiological characteristics according to the well-stirred model it is possible to predict a (metabolic) in-vivo clearance with respect to phase I reactions. The (metabolic) in-vivo clearance in humans predicted correspondingly for the test compounds 4-[(11β,17β)-17-hydroxy-3-oxo-17-(pentafluoro-ethyl)estra-4,9-dien-11-yl]benzamide and 4'-[(11β,17β)-17-hydroxy-3-oxo-17-(pentafluoro-ethyl)estra-4,9-dien-11-yl]biphenyl-4-carboxamide was very low, at 0.33 L/h/kg and 0.21 L/h/kg respectively.

Determination of Clearance and Half-Life after Intravenous Application in Rats

The in-vivo clearance and half-life of the test substances were determined in female rats with a body weight of approx. 200-250 g. For this, the test substances (in cassette testing, up to 3 different substances per animal) were applied in dissolved form at a dose of 0.3-0.5 mg/kg as a bolus with a volume of 2 ml/kg intravenously (i.v.) in the caudal vein, using compatible solubilizers such as PEG400 and/or ethanol in a compatible amount. Blood samples of approx. 0.2 mL were taken from a polyurethane catheter in the vena jugularis at the time points 2 min, 8 min, 15 min, 30 min, 45 min, 1 h, 2 h, 4 h, 6 h, 8 h, 24 h. The blood samples were kept in lithium-heparin tubes (Monovetten® from Sarstedt) without shaking, and were centrifuged for 15 min at 3000 rpm. A 100 μL aliquot was taken from the supernatant (plasma) and was precipitated by adding 400 μL of cold methanol. The precipitated samples were frozen out overnight at −20° C., then centrifuged once again for 15 min at 3000 rpm before 150 μL of the clear supernatant was taken for the determination of concentration. Analysis was carried out with an Agilent 1200 HPLC system connected to LCMS/MS detection.

Calculation of the pK Parameters (Via Non-Linear Regression by pK Calculation Software):

CLplasma: total plasma clearance of the test substance (in L*kg/h), where CLplasma=dose/AUCinf;

AUCinf: extrapolated area under the plasma concentration-time curve (in μg*h/L);

CLblood: total blood clearance of the test substance (in L*kg/h), where (CLblood=CLplasma*Cp/Cb);

Cb/Cp: ratio of blood to plasma concentration distribution of the test substance;

t½: terminal half-life of the test substance (in h).

TABLE 3

| Example | $CL_{blood}$ [L/h/kg] | t½ [h] |
|---|---|---|
| 79 | 0.4 | 9 |

The invention claimed is:
1. A compound of formula I

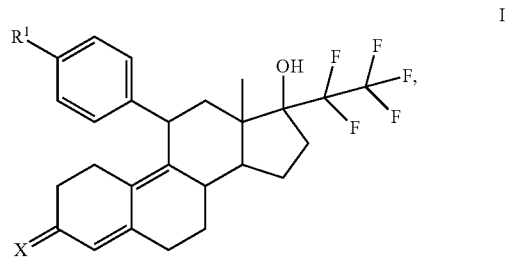

in which $R^1$ stands either for a residue Y or for a phenyl ring substituted with Y,
Y stands for a group

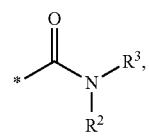

$R^2$ and $R^3$ are identical or different and stand for hydrogen, an optionally —N(CH$_3$)$_2$,

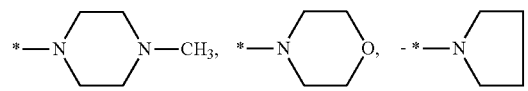

or —NHC(O)CH$_3$ substituted $C_1$-$C_6$-alkyl residue, a

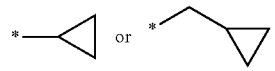

residue
a 6-10-membered aryl residue optionally substituted one, two or more times with halogen, —OH, —Oalkyl, —C(O)OH, —C(O)O-alkyl, —C(O)NH$_2$, —C(O)NH-alkyl, —C(O)N-dialkyl, —C(O)NH-aryl, —C(O)NH-heteroaryl, —NH$_2$, —NH($C_1$-$C_6$-alkyl), —N($C_1$-$C_6$-alkyl)$_2$, —NHC(O)alkyl, —NO$_2$, —N$_3$, —CN, —$C_1$-$C_6$-alkyl, —$C_1$-$C_6$-perfluoroalkyl, —$C_1$-$C_6$-acyl, —$C_1$-$C_6$-acyloxy, —SO$_2$NH$_2$, —SO$_2$NH-alkyl or —SO$_2$N-dialkyl,
a 5-10-membered heteroaryl residue optionally substituted one, two or more times with the aforementioned substituents of the 6-10-membered aryl residue,
a $C_1$-$C_6$-aralkyl residue optionally substituted on the aryl ring one, two or more times with the aforementioned substituents of the 6-10-membered aryl residue or
a $C_1$-$C_6$-heteroarylalkyl residue optionally substituted on the heteroaryl ring one, two or more times with the aforementioned substituents of the 6-10-membered aryl residue or else,
$R^2$ and $R^3$
are together a constituent of a 3-10-membered ring optionally substituted with alkyl-, carboxyl-, alkoxycarbonyl-, alkylcarbonyl-, aminocarbonyl-, aryl-, aralkyl-, heteroaryl-, heteroarylalkyl-, aminoalkyl- or dimethylaminoalkyl-substituted on the carbon or alkyl-, alkanoyl-, carboxyl-, alkoxycarbonyl-, aryl-, pyridinyl-, pyrimidinyl-, pyrazinyl-, sulphonyl-, benzoyl-, alkylsulphonyl-, arylsulphonyl-, aminocarbonyl-, dimethylaminocarbonyl-, aminocarbonylalkyl-, alkylaminocarbonylalkyl-, aralkyl-, heterocyclylalkyl-heteroarylalkyl-, aminoalkyl- or

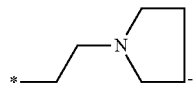

substituted on the nitrogen, which optionally contains nitrogen, oxygen or sulphur atoms, which is optionally oxidized to the sulphoxide or sulphone, wherein optionally an aromatic is condensed onto the 3-10-membered ring, X denotes an oxygen atom, $NOR^4$ or $NNHSO_2R^4$ and
$R^4$ is selected from the group comprising hydrogen, $C_1$-$C_6$-alkyl and aryl or a salt thereof.

2. Compound according to claim 1 of general formula V:

Formula V

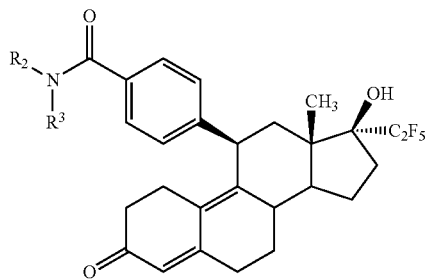

in which
$R^2$ denotes hydrogen, $C_1$-$C_4$-alkyl, $-(CH_2)_k-N(CH_3)_2$ with k=2 or 3, $-CH_2-CH_2-NH-CO-CH_3$ and $-(CH_2)_k-R^5$ with k=2 or 3 and $R^5$=

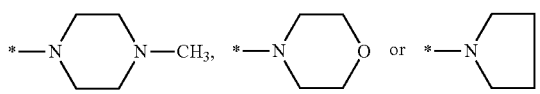

and
$R^3$ denotes hydrogen or $C_1$-$C_4$-alkyl
or a salt thereof.

3. Compound according to claim 1 of general formula VI

Formula VI

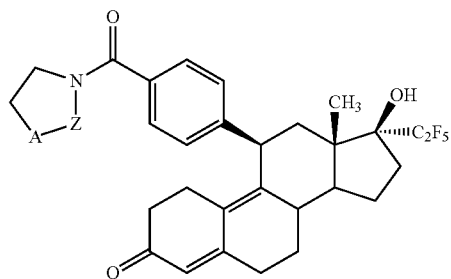

in which
Z denotes $-CH_2-$ or $-CH_2-CH_2-$,
A denotes oxygen, $-CHR^6-$ or $-NR^7-$ and
$R^6$, $R^7$ denote hydrogen, $C_1$-$C_4$-alkyl,
a $-(CH_2)_l$-aryl residue with l=0, 1 or 2, optionally substituted one, two or more times with halogen $-OH$, $-O$-alkyl, $-CO_2H$, $-CO_2$-alkyl, $-C(O)NH_2$, $-C(O)NH$-alkyl, $-C(O)N$-dialkyl, $-C(O)NH$-aryl, $-C(O)NH$-heteroaryl, $-NH_2$, $(C_1$-$C_6$-alkyl), $-N(C_1$-$C_6$-alkyl)$_2$, $-NHC(O)$alkyl, $-NO_2$, $-N_3$, $-CN$,
$-C_1$-$C_6$-alkyl, $-C_1$-$C_6$-perfluoro-alkyl, $-C_1$-$C_6$-acyl, $-C_1$-$C_6$-acyloxy, $-SO_2NH_2$, $-SO_2NH$-alkyl or $-SO_2N$-dialkyl,
a $-(CH_2)_l$-heteroaryl residue with up to two heteroatoms and l=0, 1 or 2, optionally substituted one, two or more times with halogen, $-OH$, $-O$-alkyl, $-CO_2H$, $-CO_2$-alkyl, $-C(O)NH_2$, $-C(O)NH$-alkyl, $-C(O)N$-dialkyl, $-C(O)NH$-aryl, $-C(O)NH$-heteroaryl, $-NH_2$, $-NH(C_1$-$C_6$-alkyl), $-N(C_1$-$C_6$-alkyl)$_2$, $-NHC(O)$alkyl, $-NO_2$, $-N_3$, $-CN$, $-C_1$-$C_6$-alkyl, $-C_1$-$C_6$-perfluoro-alkyl, $-C_1$-$C_6$-acyl, $-C_1$-$C_6$-acyloxy, $-SO_2NH_2$, $-SO_2NR$-alkyl or $-SO_2N$-dialkyl or $-COR^8$ and
$R^8$ denotes $-OH$, $-(C_1$-$C_4$-alkyl), -aryl, $-O$-$C_1$-$C_4$-alkyl, $-NH-(C_1$-$C_4$-alkyl), $-N(CH_3)_2$, or $-SO_2-(C_1$-$C_4$-alkyl)
or a salt thereof.

4. Compound according to claim 3 in which
$R^6$ denotes hydrogen, phenyl, $-CO_2H$, $-CO_2CH_3$ and
$R^7$ denotes hydrogen, $-CH_3$, $-(CH_2)_l$-phenyl with l=0, 1 or 2,

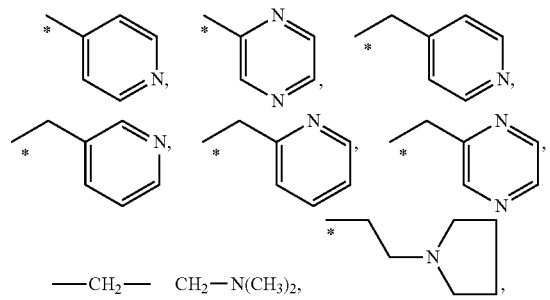

$-CO-CH_3$, $-CO$-phenyl, $-CO_2CH_3$, $-CO_2C(CH_3)_3$, $-CO-NH-CH_3$, $-CO-N(CH_3)_2$; $-SO_2-CH_3$, or $-CH_2CO-NH-CH_3$
or a salt thereof.

5. Compound according to claim 1 of general formula VII:

Formula VII

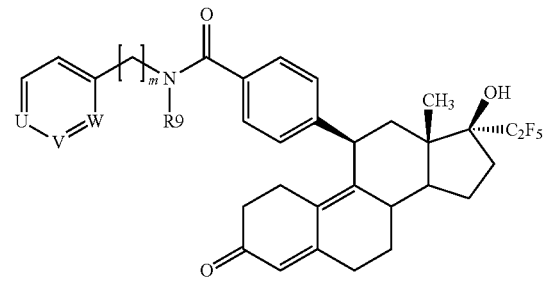

in which
m denotes 0, 1 or 2,
$R^9$ denotes hydrogen or $-C_1$-$C_4$-alkyl,

U, V and W independently of one another denote —CH═, —CR$^{10}$═ or —N═, and —CR$^{10}$═ or —N═, regardless of the position in the aromatic ring, are present at most once and R$^{10}$ denotes —O—(C$_1$-C$_4$-alkyl), halogen, —COR$^{11}$ with R$^{11}$═—OH, —NH$_2$ or —O—(C$_1$-C$_4$-alkyl), —SO$_2$—NH$_2$; —NH—CO—(C$_1$-C$_4$-alkyl), or —CO—NH-aryl or a salt thereof.

6. Compound according to claim 5 in which

R$^9$ denotes hydrogen, methyl or ethyl and

R$^{10}$ denotes —O—CH$_3$, —Cl, —CO$_2$H, —CO$_2$CH$_3$, —CO—NH$_2$, —SO$_2$—NH$_2$; —NH—CO—CH$_3$ or —CO—NH-phenyl or a salt thereof.

7. A compound selected from

4-[(11β,17β)-17-hydroxy-3-oxo-17-(pentafluoroethyl)estra-4,9-dien-11-yl]benzamide;

4-[(11β,17β)-17-hydroxy-3-oxo-17-(pentafluoroethyl)estra-4,9-dien-11-yl]-N,N-dimethylbenzamide;

(11β,17β)-17-hydroxy-11-{4-[(4-methylpiperazin-1-yl)carbonyl]phenyl}-17-(pentafluoroethyl)estra-4,9-dien-3-one;

tert-butyl-4-{4-[(11β,17β)-17-hydroxy-3-oxo-17-(pentafluoroethyl)estra-4,9-dien-11-yl]benzoyl}piperazine-1-carboxylate;

(11β,17β)-17-hydroxy-17-(pentafluoroethyl)-11-[4-(piperidin-1-ylcarbonyl)phenyl]estra-4,9-dien-3-one;

methyl-1-{4-[(11β,17β)-17-hydroxy-3-oxo-17-(pentafluoroethyl)estra-4,9-dien-11-yl]benzoyl}piperidine-4-carboxylate;

N-[2-(dimethylamino)ethyl]-4-[(11β,17β)-17-hydroxy-3-oxo-17-(pentafluoroethyl)estra-4,9-dien-11-yl]benzamide;

N-[3-(dimethylamino)propyl]-4-[(11β,17β)-17-hydroxy-3-oxo-17-(pentafluoroethyl)estra-4,9-dien-11-yl]benzamide;

N-[2-(dimethylamino)ethyl]-4-[(11β,17β)-17-hydroxy-3-oxo-17-(pentafluoroethyl)estra-4,9-dien-11-yl]-N-methylbenzamide;

methyl-2-({4-[(11β,17β)-17-hydroxy-3-oxo-17-(pentafluoroethyl)estra-4,9-dien-11-yl]benzoyl}amino)benzoate;

4-[(11β,17β)-17-hydroxy-3-oxo-17-(pentafluoroethyl)estra-4,9-dien-11-yl]-N-(pyridin-2-yl)benzamide;

4-[(11β,17β)-17-hydroxy-3-oxo-17-(pentafluoroethyl)estra-4,9-dien-11-yl]-N-(pyridin-3-yl)benzamide;

4-[(11β,17β)-17-hydroxy-3-oxo-17-(pentafluoroethyl)estra-4,9-dien-11-yl]-N-[3-(morpholin-4-yl)propyl]benzamide;

4-[(11β,17β)-17-hydroxy-3-oxo-17-(pentafluoroethyl)estra-4,9-dien-11-yl]-N-(pyridin-4-yl)benzamide;

(11β,17β)-17-hydroxy-17-(pentafluoroethyl)-11-[4-(pyrrolidin-1-ylcarbonyl)phenyl]estra-4,9-dien-3-one;

4-[(11β,17β)-17-hydroxy-3-oxo-17-(pentafluoroethyl)estra-4,9-dien-11-yl]-N-(2-phenylethyl)benzamide;

4-[(11β,17β)-17-hydroxy-3-oxo-17-(pentafluoroethyl)estra-4,9-dien-11-yl]-N-(2-phenylpropan-2-yl)benzamide;

4-[(11β,17β)-17-hydroxy-3-oxo-17-(pentafluoroethyl)estra-4,9-dien-11-yl]-N-(4-sulphamoylbenzyl)benzamide;

N-ethyl-4-[(11β,17β)-17-hydroxy-3-oxo-17-(pentafluoroethyl)estra-4,9-dien-11-yl]benzamide;

4-[(11β,17β)-17-hydroxy-3-oxo-17-(pentafluoroethyl)estra-4,9-dien-11-yl]-N-(pyridin-2-ylmethyl)benzamide;

4-[(11β,17β)-17-hydroxy-3-oxo-17-(pentafluoroethyl)estra-4,9-dien-11-yl]-N-(pyridin-4-ylmethyl)benzamide;

4-[(11β,17β)-17-hydroxy-3-oxo-17-(pentafluoroethyl)estra-4,9-dien-11-yl]-N-phenylbenzamide;

4-[(11β,17β)-17-hydroxy-3-oxo-17-(pentafluoroethyl)estra-4,9-dien-11-yl]-N-(2-methoxyphenyl)benzamide;

4-[(11β,17β)-17-hydroxy-3-oxo-17-(pentafluoroethyl)estra-4,9-dien-11-yl]-N-(3-methoxyphenyl)benzamide;

4-[(11β,17β)-17-hydroxy-3-oxo-17-(pentafluoroethyl)estra-4,9-dien-11-yl]-N-(4-methoxyphenyl)benzamide;

N-(4-chlorophenyl)-4-[(11β,17β)-17-hydroxy-3-oxo-17-(pentafluoroethyl)estra-4,9-dien-11-yl]benzamide;

N,N-diethyl-4-[(11β,17β)-17-hydroxy-3-oxo-17-(pentafluoroethyl)estra-4,9-dien-11-yl]benzamide;

4-[(11β,17β)-17-hydroxy-3-oxo-17-(pentafluoroethyl)estra-4,9-dien-11-yl]-N-methyl-N-phenylbenzamide;

(11β,17β)-17-hydroxy-11-[4-(morpholin-4-ylcarbonyl)phenyl]-17-(pentafluoroethyl)estra-4,9-dien-3-one;

(11β,17β)-17-hydroxy-17-(pentafluoroethyl)-11-{4-[(4-phenylpiperazin-1-yl)carbonyl]phenyl}estra-4,9-dien-3-one;

4-[(11β,17β)-17-hydroxy-3-oxo-17-(pentafluoroethyl)estra-4,9-dien-11-yl]-N-methyl-N-(pyridin-2-ylmethyl)benzamide;

4-[(11β,17β)-17-hydroxy-3-oxo-17-(pentafluoroethyl)estra-4,9-dien-11-yl]-N-methyl-N-(pyridin-3-ylmethyl)benzamide;

4-[(11β,17β)-17-hydroxy-3-oxo-17-(pentafluoroethyl)estra-4,9-dien-11-yl]-N-methyl-N-(pyridin-4-ylmethyl)benzamide;

N-benzyl-4-[(11β,17β)-17-hydroxy-3-oxo-17-(pentafluoroethyl)estra-4,9-dien-11-yl]benzamide;

4-[(11β,17β)-17-hydroxy-3-oxo-17-(pentafluoroethyl)estra-4,9-dien-11-yl]-N-(4-methoxybenzyl)benzamide;

N-(4-chlorobenzyl)-4-[(11β,17β)-17-hydroxy-3-oxo-17-(pentafluoroethyl)estra-4,9-dien-11-yl]benzamide;

N-(2-acetamidoethyl)-4-[(11β,17β)-17-hydroxy-3-oxo-17-(pentafluoroethyl)estra-4,9-dien-11-yl]benzamide;

methyl-4-({4-[(11β,17β)-17-hydroxy-3-oxo-17-(pentafluoroethyl)estra-4,9-dien-11-yl]benzoyl}amino)benzoate;

(11β,17β)-11-[4-(3,4-dihydroisoquinolin-2(1H)-ylcarbonyl)phenyl]-17-hydroxy-17-(pentafluoroethyl)estra-4,9-dien-3-one;

(11β,17β)-11-{4-[(4-benzylpiperazin-1-yl)carbonyl]phenyl}-17-hydroxy-17-(pentafluoroethyl)estra-4,9-dien-3-one;

N-(4-carbamoylphenyl)-4-[(11β,17β)-17-hydroxy-3-oxo-17-(pentafluoroethyl)estra-4,9-dien-11-yl]benzamide;

N-cyclopropyl-4-[(11β,17β)-17-hydroxy-3-oxo-17-(pentafluoroethyl)estra-4,9-dien-11-yl]benzamide;

4-[(11β,17β)-17-hydroxy-3-oxo-17-(pentafluoroethyl)estra-4,9-dien-11-yl]-N-methyl-N-(2-phenylethyl)benzamide;

(11β,17β)-17-hydroxy-17-(pentafluoroethyl)-11-(4-{[4-(2-phenylethyl)piperazin-1-yl]carbonyl}phenyl)estra-4,9-dien-3-one;

(11β,17β)-17-hydroxy-17-(pentafluoroethyl)-11-(4-{[4-(pyridin-4-yl)piperazin-1-yl]carbonyl}phenyl)estra-4,9-dien-3-one;

(11β,17β)-17-hydroxy-17-(pentafluoroethyl)-11-(4-{[4-(pyrazin-2-yl)piperazin-1-yl]carbonyl}phenyl)estra-4,9-dien-3-one;

(11β,17β)-11-[4-({4-[2-(dimethylamino)ethyl]piperazin-1-yl}carbonyl)phenyl]-17-hydroxy-17-(pentafluoroethyl)estra-4,9-dien-3-one;

(11β,17β)-17-hydroxy-17-(pentafluoroethyl)-11-[4-({4-[2-(pyrrolidin-1-yl)ethyl]piperazin-1-yl}carbonyl)phenyl]estra-4,9-dien-3-one;

(11β,17β)-17-hydroxy-17-(pentafluoroethyl)-11(4-{[4-(pyridin-4-ylmethyl)piperazin-1-yl]carbonyl}phenyl)estra-4,9-dien-3-one;

4-[(11β,17(3)-17-hydroxy-3-oxo-17-(pentafluoroethyl)estra-4,9-dien-11-yl]-N-methyl-N-[2-(pyridin-2-yl)ethyl]benzamide;

N-benzyl-4-[(11β,17(3)-17-hydroxy-3-oxo-17-(pentafluoroethyl)estra-4,9-dien-11-yl)-N-methylbenzamide;

N-(4-acetamidophenyl)-4-[(11β, 17(3)-17-hydroxy-3-oxo-17-(pentafluoroethyl)estra-4,9-dien-11-yl]benzamide;

4-[(11β,17(3)-17-hydroxy-3-oxo-17-(pentafluoroethyl)estra-4,9-dien-11-yl]-N-(3-methoxybenzyl)benzamide;

4-[(11β,17(3)-17-hydroxy-3-oxo-17-(pentafluoroethyl)estra-4,9-dien-11-yl]-N-[2-(pyrrolidin-1-yl)ethyl]benzamide;

4-[(11β,17(3)-17-hydroxy-3-oxo-17-(pentafluoroethyl)estra-4,9-dien-11-yl]-N-[2-(pyridin-3-yl)ethyl]benzamide;

N-(3-chlorobenzyl)-4-[(11β,17β)-17-hydroxy-3-oxo-17-(pentafluoroethyl)estra-4,9-dien-11-yl]benzamide;

methyl-3-({4-[(11β,17β)-17-hydroxy-3-oxo-17-(pentafluoroethyl)estra-4,9-dien-11-yl]benzoyl}amino)benzoate;

4-[(11β,17β)-17-hydroxy-3-oxo-17-(pentafluoroethyl)estra-4,9-dien-11-yl]-N-methyl-N-[2-(pyridin-4-yl)ethyl]benzamide;

N-(cyclopropylmethyl)-4-[(11β,17β)-17-hydroxy-3-oxo-17-(pentafluoroethyl)estra-4,9-dien-11-yl]benzamide;

4-[(11β,17β)-17-hydroxy-3-oxo-17-(pentafluoroethyl)estra-4,9-dien-11-yl]-N-[4-(phenylcarbamoyl)phenyl]benzamide;

4-[(11β,17β)-17-hydroxy-3-oxo-17-(pentafluoroethyl)estra-4,9-dien-11-yl]-N-[2-(pyridin-2-yl)ethyl]benzamide;

4-[(11β,17β)-17-hydroxy-3-oxo-17-(pentafluoroethyl)estra-4,9-dien-11-yl]-N-[2-(4-methylpiperazin-1-yl)ethyl]benzamide;

(11β,17β)-17-hydroxy-17-(pentafluoroethyl)-11-{4-[(4-phenylpiperidin-1-yl)carbonyl]phenyl}estra-4,9-dien-3-one;

4-[(11β,17β)-17-hydroxy-3-oxo-17-(pentafluoroethyl)estra-4,9-dien-11-yl]-N-[2-(pyridin-4-yl)ethyl]benzamide;

(11β,17β)-11-{4-[(4-benzoylpiperazin-1-yl)carbonyl]phenyl}-17-hydroxy-17-(pentafluoroethyl)estra-4,9-dien-3-one;

4-{4-[(11β,17β)-17-hydroxy-3-oxo-17-(pentafluoroethyl)estra-4,9-dien-11-yl]benzoyl}-N,N-dimethylpiperazine-1-carboxamide;

(11β,17β)-17-hydroxy-11-(4-{[4-(methylsulphonyl)piperazin-1-yl]carbonyl}phenyl)-17-(pentafluoroethyl)estra-4,9-dien-3-one;

(11β,17β)-17-hydroxy-17-(pentafluoroethyl)-11-(4-{[4-(pyridin-2-ylmethyl)piperazin-1-yl]carbonyl}phenyl)estra-4,9-dien-3-one;

(11β,17β)-17-hydroxy-17-(pentafluoroethyl)-11-(4-{[4-(pyridin-3-ylmethyl)piperazin-1-yl]carbonyl}phenyl)estra-4,9-dien-3-one;

methyl-4-{4-[(11β,17β)-17-hydroxy-3-oxo-17-(pentafluoroethyl)estra-4,9-dien-11-yl]benzoyl}piperazine-1-carboxylate;

2-(4-{4-[(11β,17β)-17-hydroxy-3-oxo-17-(pentafluoroethyl)estra-4,9-dien-11-yl]benzoyl}piperazin-1-yl)-N-methylacetamide;

4-[(11β,17β)-17-hydroxy-3-oxo-17-(pentafluoroethyl)estra-4,9-dien-11-yl]-N-methyl-N-[2-(pyridin-3-yl)ethyl]benzamide;

(11β,17β)-17-hydroxy-17-(pentafluoroethyl)-11-[4-(piperazin-1-ylcarbonyl)phenyl]estra-4,9-dien-3-one;

(11β,17β)-11-{4-[(4-acetylpiperazin-1-yl)carbonyl]phenyl}-17-hydroxy-17-(pentafluoroethyl)estra-4,9-dien-3-one;

1-{4-[(11β,17β)-17-hydroxy-3-oxo-17-(pentafluoroethyl)estra-4,9-dien-11-yl]benzoyl}piperidine-4-carboxylic acid;

2-({4-[(11β,17β)-17-hydroxy-3-oxo-17-(pentafluoroethyl)estra-4,9-dien-11-yl]benzoyl}amino)benzoic acid;

3-({4-[(11β,17β)-17-hydroxy-3-oxo-17-(pentafluoroethyl)estra-4,9-dien-11-yl]benzoyl}amino)benzoic acid;

4-({4-[(11β,17β)-17-hydroxy-3-oxo-17-(pentafluoroethyl)estra-4,9-dien-11-yl]benzoyl}amino)benzoic acid; and 4'-[(11β,17β)-17-hydroxy-3-oxo-17-(pentafluoroethyl)estra-4,9-dien-11-yl]biphenyl-4-carboxamide;

or a salt thereof.

8. Medicinal product comprising a compound as defined in claim 1 in combination with a pharmaceutically suitable excipient.

9. A method of treating uterine fibroids, endometriosis, heavy menstrual bleeding, meningiomata, or breast cancer comprising the step of administering to a patient in need thereof of a compound according to claim 1.

10. A method of contraception comprising the step of administering to a patient in need thereof of a compound according to claim 1.

* * * * *